United States Patent
French et al.

(10) Patent No.: US 9,518,260 B2
(45) Date of Patent: Dec. 13, 2016

(54) PAIN TREATMENT

(71) Applicant: BENITEC BIOPHARMA LIMITED, Balmain, New South Wales (AU)

(72) Inventors: Peter William French, Balmain (AU); Michael Wayne Graham, Jindalee (AU)

(73) Assignee: Benitec Biopharma Limited, Balmain, New South Wales (AU)

( * ) Notice: Subject to any disclaimer, the term of this patent is extended or adjusted under 35 U.S.C. 154(b) by 0 days.

(21) Appl. No.: 14/382,206

(22) PCT Filed: Feb. 28, 2013

(86) PCT No.: PCT/AU2013/000190
§ 371 (c)(1),
(2) Date: Aug. 29, 2014

(87) PCT Pub. No.: WO2013/126963
PCT Pub. Date: Sep. 6, 2013

(65) Prior Publication Data
US 2015/0045411 A1 Feb. 12, 2015

(30) Foreign Application Priority Data
Feb. 29, 2012 (AU) ............................... 2012900796

(51) Int. Cl.
*C07H 21/04* (2006.01)
*C12N 15/113* (2010.01)

(52) U.S. Cl.
CPC ......... *C12N 15/113* (2013.01); *C12N 15/1137* (2013.01); *C12Y 104/03003* (2013.01); *C12Y 207/11013* (2013.01); *C12N 2310/14* (2013.01); *C12N 2310/141* (2013.01); *C12N 2310/51* (2013.01); *C12N 2310/531* (2013.01)

(58) Field of Classification Search
None
See application file for complete search history.

(56) References Cited

U.S. PATENT DOCUMENTS

2006/0189561 A1* 8/2006 Roelvink ............... C12N 15/111
514/44 R
2007/0081982 A1 4/2007 Evertsz et al.

FOREIGN PATENT DOCUMENTS

| CN | 102604950 A | 7/2012 |
|---|---|---|
| WO | WO 00/53218 A1 | 9/2000 |
| WO | WO 2006/006948 A2 | 1/2006 |

OTHER PUBLICATIONS

Song, Z. et al. 2010 "Gene knockdown with lentiviral vector mediated intrathecal RNA interference of protein kinase C gamma reverses chronic morphine tolerance in rats" J *Gene Medicine* 12: 873-880.

Wang, Y.-X. et al. 2011 "Pain biology of spinal D-amino acids oxidase (DAAO)" *12th International Congress on Amino Acids, Peptides and Proteins*, vol. 41 (Suppl 1), S19 (Abstract).

Zhou, et al. 2011 "Intrathecal lentiviral-mediated RNA interference targeting PKCγ attenuates chronic constriction injury-induced neuropathic pain in rats" *Human Gene Therapy* 22: 465-475.

* cited by examiner

*Primary Examiner* — Kimberly Chong
(74) *Attorney, Agent, or Firm* — Fenwick & West LLP

(57) ABSTRACT

The disclosure relates to an RNA interference (RNAi) agent and the use of that RNAi agent to treat chronic pain in individuals, as well as pharmaceutical compositions containing the RNAi agents of the invention. The DNA-directed RNA interference (ddRNAi) agent for inhibiting expression of one or more target sequences in a pain associated gene comprises, one or more effector sequence sequences and effector complement sequences of at least 17 nucleotides in length, wherein the effector sequence is substantially complementary to the predicted transcript of a target sequence within a pain associated gene.

25 Claims, 11 Drawing Sheets

Figure 2A

Figure 2B

Figure 1A:
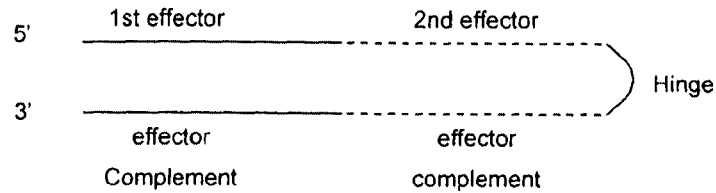

BLTPKC1 - Targeting SEQ ID NO:1 with an effector sequence of SEQ ID NO:19 with a 3'uu (bold underlined)

shRNA1 (SEQ ID NO:49)
```
       G                       CAA
        GCAAGGGGUUCCUGACCAAGC     \
        CGUUCCCCAAGGACUGGUUCG      G
   uuA                           AGA
```

BLTPKC2 - Targeting SEQ ID NO:2 with an effector sequence of SEQ ID NO:20 with a 3'uu (bold underlined)

shRNA2 (SEQ ID NO:50)
```
                                CAA
        GGCCUCUUCUUCCUUCACAACC    \
        CCGGAGAAGAAGGAAGUGUUGG     G
   uu                            AGA
```

BLTPKC3 - Targeting SEQ ID NO:3 with an effector sequence of SEQ ID NO:21 with a 3'uu (bold underlined)

shRNA3 (SEQ ID NO:51)
```
                                CAA
        GGCUUCAGCUUCCUCAUGGUUC    \
        CUGAAGUCGAAGGAGUACCAAG     G
   uu                            AGA
```

BLTPKC4 - Targeting SEQ ID NO:4 with an effector sequence of SEQ ID NO:22 with a 3'uu (bold underlined)

shRNA4 (SEQ ID NO:52)
```
                                CAA
        GGCCUCCUCCAGAAGUUUGAGG    \
        uCGGAGGAGGUCUUCAAACUCC     G
   u                             AGA
```

Figure 2B (continued...)

BLTPKC5 - Targeting SEQ ID NO:5 with an effector sequence of SEQ ID NO:23 with a 3'uu (bold underlined)

shRNA5 (SEQ ID NO:53)

```
                              CAA
    GGUGGCCGAUGCUGACAACUGC      \
    uuACCGGCUACGACUGUUGACG      G
                              AGA
```

BLTPKC6 - Targeting SEQ ID NO:6 with an effector sequence of SEQ ID NO:24 with a 3'uu (bold underlined)

shRNA6 (SEQ ID NO:54)

```
                              CAA
    GGGGAGGGCGAGUAUUACAAUG      \
    uuCCUCCCGCUCAUAAUGUUAC      G
                              AGA
```

BLTPKC7 - Targeting SEQ ID NO:7 with an effector sequence of SEQ ID NO:25 with a 3'uu (bold underlined)

shRNA7 (SEQ ID NO:55)

```
                              CAA
    GGUGCCAUGUCCUUUGGUGUC       \
    CCACGGUACAGGAAACCACAG       G
  uu                          AGA
```

BLTPKC7 - Targeting SEQ ID NO:8 with an effector sequence of SEQ ID NO:26 with a 3'uu (bold underlined)

shRNA8 (SEQ ID NO:56)

```
                              CAA
    GGCAGCCUCCUCCAGAAGUUUG      \
    uCGUCGGAGGAGGUCUUCAAAC      G
   u                          AGA
```

Figure 4A

BLTDAOr9 - Targeting SEQ ID NO:9 with an effector sequence of SEQ ID NO:27 with a 3'uu (bold underlined)

shRNA9 (SEQ ID NO:57)

```
                              CAA
    GGGAACUGGAGCGAGCUAAACA      \
    CCCUUGACCUCGCUCGAUUUGU      G
 uu                           AGA
```

BLTDAOr11 - Targeting SEQ ID NO:11 with an effector sequence of SEQ ID NO:29 with a 3'uu (bold underlined)

shRNA11 (SEQ ID NO:58)

```
                              CAA
    GGCCGGGGCCAGAUCAUCCAGG      \
    CCGGCCCCGGUCUAGUAGGUCC      G
 uu                           AGA
```

BLTDAOr13 - Targeting SEQ ID NO:13 with an effector sequence of SEQ ID NO:31 with a 3'uu (bold underlined)

shRNA13 (SEQ ID NO:59)

```
                              CAA
    GGCGUGGAUGUGAUUAUCAACU      \
    CCGCACCUACACUAAUAGUUGA      G
 uu                           AGA
```

BLTDAOr15 - Targeting SEQ ID NO:15 with an effector sequence of SEQ ID NO:33 with a 3'uu (bold underlined)

shRNA15 (SEQ ID NO:60)

```
                              CAA
    GGCUGACUGAGAGGUUAACUGA      \
    CCGACUGACUCUCCAAUUGACU      G
 uu                           AGA
```

Figure 4A (continued...)

BLTDAOr17- Targeting SEQ ID NO:17 with an effector sequence of SEQ ID NO:35 with a 3'uu (bold underlined)

shRNA17 (SEQ ID NO:61)

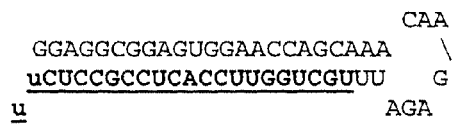

Figure 4B

BLTDAOh10 - Targeting SEQ ID NO:10 with an effector sequence of SEQ ID NO:28 with a 3'uu (bold underlined)

shRNA10 (SEQ ID NO:62)

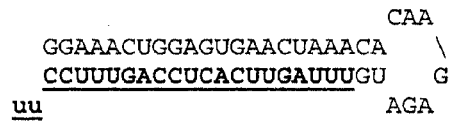

BLTDAOh12 - Targeting SEQ ID NO:12 with an effector sequence of SEQ ID NO:30 with a 3'uu (bold underlined)

shRNA12 (SEQ ID NO:63)

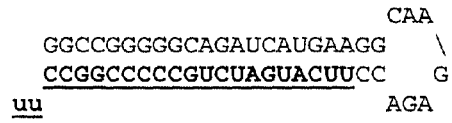

BLTDAOh14 - Targeting SEQ ID NO:14 with an effector sequence of SEQ ID NO:32 with a 3'uu (bold underlined)

shRNA14 (SEQ ID NO:64)

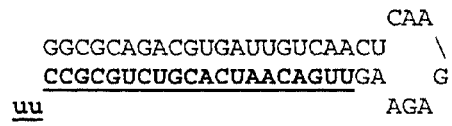

Figure 4B (continued...)
BLTDAOh16 - Targeting SEQ ID NO:16 with an effector sequence of SEQ ID NO:34 with a 3'uu (bold underlined)
shRNA16 (SEQ ID NO:65)
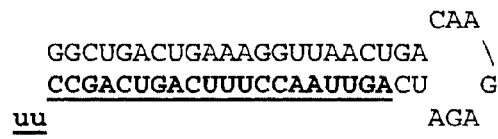
BLTDAOh18 - Targeting SEQ ID NO:18 with an effector sequence of SEQ ID NO:36 with a 3'uu (bold underlined)
shRNA18 (SEQ ID NO:66)
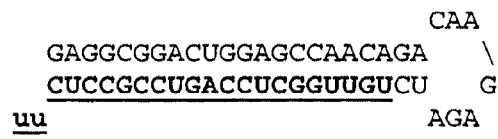

Figure 5A

BOPKC3 construct (SEQ ID NO:45) - Targeting SEQ ID NO:3 with an effector sequence of SEQ ID NO:21 with a 3'uu (bold underlined)

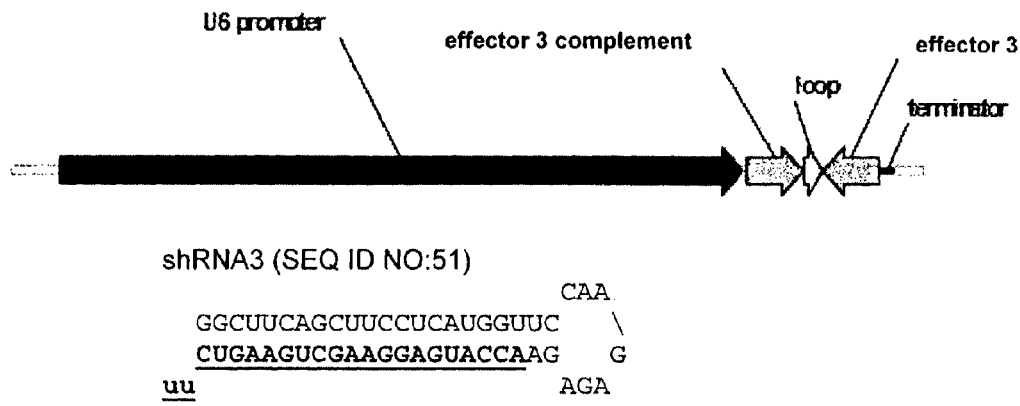

shRNA3 (SEQ ID NO:51)

```
                                  CAA
GGCUUCAGCUUCCUCAUGGUUC    \
CUGAAGUCGAAGGAGUACCAAG    G
uu                                AGA
```

Figure 5B

BOPKC3&4 construct (SEQ ID NO:46) - Targeting SEQ ID NO:3 and 4 with an effector sequence of SEQ ID NO:21 and 22 respectively with a 3'uu (bold underlined)

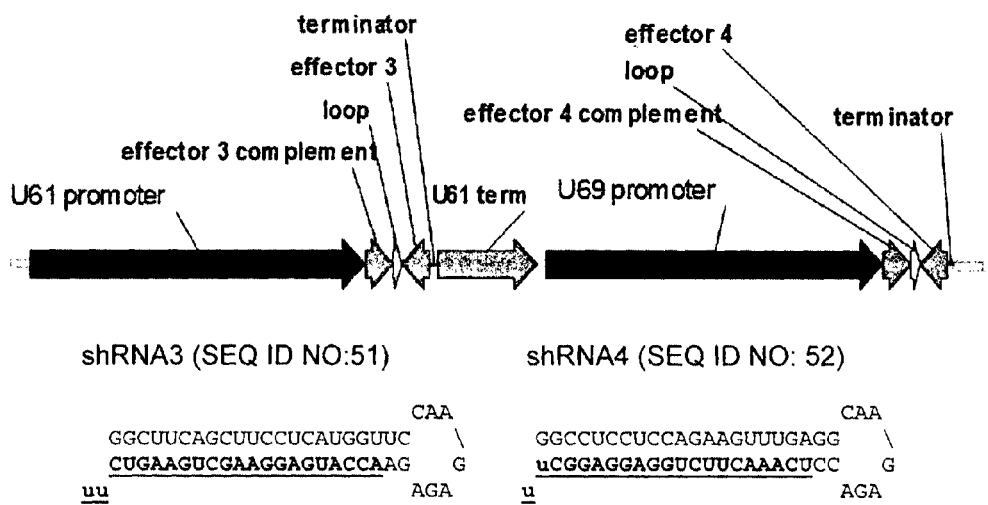

shRNA3 (SEQ ID NO:51)        shRNA4 (SEQ ID NO: 52)

```
         CAA                              CAA
GGCUUCAGCUUCCUCAUGGUUC  \    GGCCUCCUCCAGAAGUUUGAGG  \
CUGAAGUCGAAGGAGUACCAAG  G    uCGGAGGAGGUCUUCAAACUCC  G
uu                 AGA       u                  AGA
```

Figure 5C
BOPKC3cont construct (SEQ ID NO:47) - randomised shRNA based on BOPKC3; effector sequence shown with a 3' uu (bold underlined)
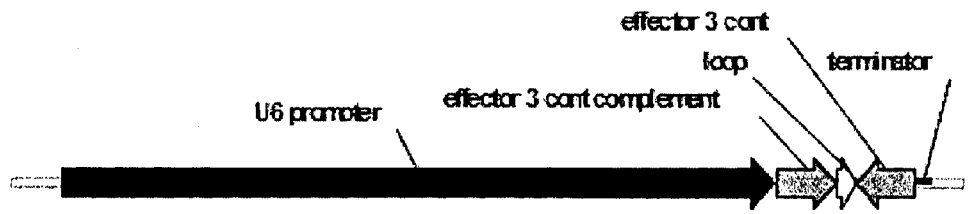
shRNA3cont (SEQ ID NO: 67)
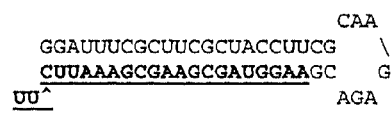
Figure 5D
BOPKC3&4cont construct (SEQ ID NO:48) - randomised shRNAs based on BOPKC3&4; control effector sequences shown with a 3' uu (bold underlined)
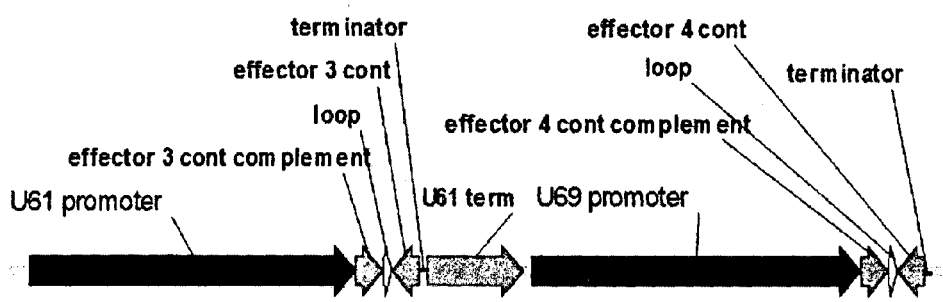
shRNA3cont (SEQ ID NO: 67)   shRNA4cont (SEQ ID NO:68)
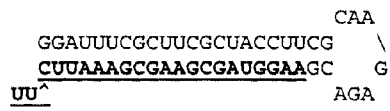 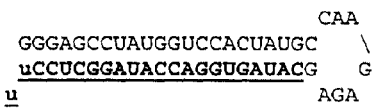

Figure 6A miRNA expressing construct

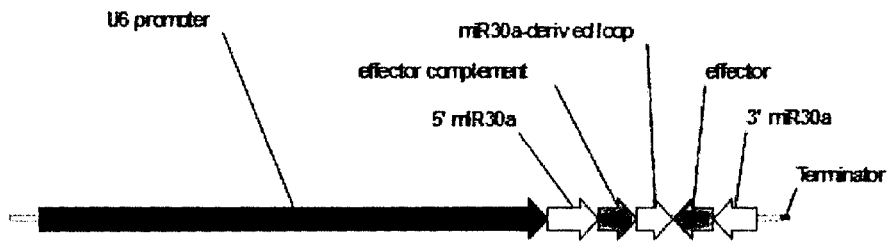

Figure 6B

BLTPKC3miR construct (SEQ ID NO: 69) expresses an RNA (SEQ ID NO:71) targeting SEQ ID NO:3 with an effector sequence of SEQ ID NO:21 gguauauugcuguugacagugagcgaGACUUCAGCUUCCUCAUGGUacugugaagcagaugggu
ACCAUGAGGAAGCUGAAGUCGcgccuacugccucggacuucaagcuagcgguaccuuuuuu Predicted structure of expressed RNA from BLTPKC3miR

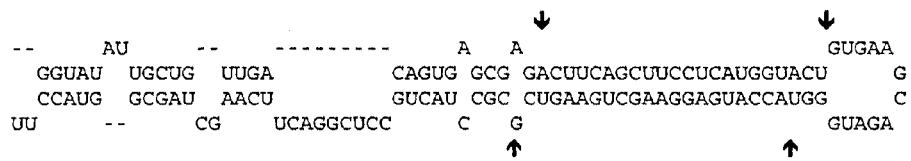

Figure 6C

BLTPKC4miR (SEQ ID NO:70) expresses an RNA (SEQ ID NO:72) targeting SEQ ID NO:4 with an effector sequence of SEQ ID NO:22 gguauauugcuguugacagugagcgaAGCCUCCUCCAGAAGUUUGAacugugaagcagaugggu
UCAAACUUCUGGAGGAGGCUGcgccuacugccucggacuucaagcuagcgguaccuuuuuu Predicted structure of expressed RNA from BLTPKC3miR

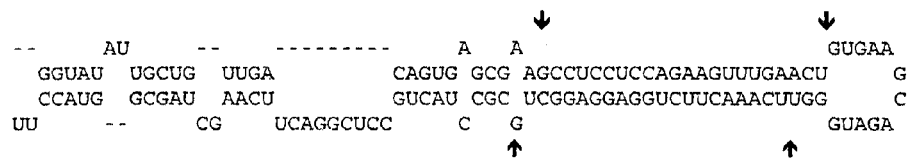

PAIN TREATMENT

FIELD OF THE INVENTION

This invention is directed to an RNA interference (RNAi) agent and the use of that RNAi agent to treat chronic pain in individuals, as well as pharmaceutical compositions containing the RNAi agents of the invention.

REFERENCE TO SEQUENCE LISTING

The present application is filed along with a Sequence Listing in electronic format. The Sequence Listing is provided as a file entitled 18764293_1.TXT, created Aug. 29, 2014, which is approximately 37.3 KB in size. The information in the electronic format of the Sequence Listing is incorporated herein by reference in its entirety.

BACKGROUND OF THE INVENTION

Pain usually falls into one of two categories:

Nociceptive pain is caused by damage to body tissue and usually described as a sharp, aching, or throbbing pain. This kind of pain can be due to benign pathology; or by tumors or cancer cells that are growing larger and crowding other body parts near the cancer site. Nociceptive pain may also be caused by cancer spreading to the bones, muscles, or joints, or that causes the blockage of an organ or blood vessels.

Neuropathic pain occurs when there is actual nerve damage. Nerves connect the spinal cord to the rest of the body and allow the brain to communicate with the skin, muscles and internal organs. Nutritional imbalance, alcoholism, toxins, infections or auto-immunity can all damage this pathway and cause pain. Neuropathic pain can also be caused by a cancer tumor pressing on a nerve or a group of nerves. People often describe this pain as a burning or heavy sensation, or numbness along the path of the affected nerve. The two types of pain are not necessarily mutually exclusive. Cancer pain for example can be nociceptive or neuropathic, or both.

The capacity to experience pain has a protective role: it warns us of imminent or actual tissue damage and elicits coordinated reflex and behavioural responses to keep such damage to a minimum. If tissue damage is unavoidable, a set of excitability changes in the peripheral and central nervous system establish a profound but reversible pain hypersensitivity in the inflamed and surrounding tissue. This process assists wound repair because any contact with the damaged part is avoided until healing has occurred. By contrast, persistent pain syndromes offer no biological advantage and cause suffering and distress. Such maladaptive pain typically results from damage to the nervous system—the peripheral nerve, the dorsal root ganglion or dorsal root, or the central nervous system—and is known as neuropathic pain. Such syndromes comprise a complex combination of negative symptoms or sensory deficits, such as partial or complete loss of sensation, and positive symptoms that include dysaethesia, paraesthesia, and pain.

Apart from trigeminal neuralgia, which responds well to carbamazepine, pharmacotherapy for neuropathic pain has been disappointing. Patients with neuropathic pain for example do not respond to non-steroidal anti-inflammatory drugs and resistance or insensitivity to opiates is common. Patients are usually treated empirically with tricyclic or serotonin and norepinephrine uptake inhibitors, antidepressants, and anticonvulsants that all have limited efficacy and undesirable side-effects. Neurosurgical lesions have a negligible role and functional neurosurgery, including dorsal column or brain stimulation, is controversial, although transcutaneous nerve stimulation may provide some relief. Local anaesthetic blocks targeted at trigger points, peripheral nerves, plexi, dorsal roots, and the sympathetic nervous system have useful but short-lived effects; longer lasting blocks by phenol injection or cryotherapy risk irreversible functional impairment and have not been tested in placebo-controlled trials. Chronic epidural administration of drugs such as clonidine, steroids, opioids, or midazolam is invasive, has side-effects, and the efficacy of these drugs has not been adequately assessed.

Pathological pain is characterized by extensive modification of the systems involved in pain signal transmission and modulation at the spinal level (primary sensory neurons and the spinal cord) and probably in the brain. Chronic pain, particularly of neuropathic origin, may also lead to tissue remodeling (plasticity). This may include, for instance, loss of spinal interneurons, abnormal rearrangement of central afferents of primary sensory neurons and glial cell activation and proliferation. These long-lasting modifications are mediated by, or associated with, changes in the production of key molecules involved in nociceptive processing. Gene-based techniques allow local or even cell-type-specific interventions to be used to correct the abnormal production of some of these proteins, modulate the activity of signal transduction pathways or overproduce various therapeutic secreted proteins. In fact, with these approaches, it may be possible to not 'only' relieve established ongoing pain but to reverse the pathological situation underlying chronic pain (Meunier and Pohl; *Gene Therapy* (2009) 16, 476-482).

There is no treatment to prevent the development of neuropathic or nociceptive pain, nor to adequately, predictably, and specifically control established neuropathic or nociceptive pain. The aim of existing treatment, therefore, is often just to help the patient cope by means of psychological or occupational therapy, rather than to eliminate the pain. Thus, there is an unmet clinical need and a challenge to develop more effective therapy. This invention is directed to an RNA interference (RNAi) agent and the use of that RNAi agent to prevent, manage or treat pain in individuals.

The RNAi pathway is initiated by the enzyme Dicer, which cleaves double-stranded RNA (dsRNA) molecules into short fragments (commonly referred to as siRNAs) of ~20-25 nucleotides. One of the two strands of each fragment, known as the guide strand or active strand, is then incorporated into the RNA-induced silencing complex (RISC) through binding to a member of the argonaute protein family. After integration into the RISC, the guide strand base-pairs with its target mRNA and is thought to either inhibit a target by inhibiting translation (by stalling the translational machinery) and/or inducing cleavage of the mRNA, thereby preventing it from being used as a translation template.

While the fragments produced by Dicer are double-stranded, only the guide strand, directs gene silencing. The other anti-guide strand referred to commonly as a passenger strand, carrier strand or * strand is frequently degraded during RISC activation (Gregory R et al., 2005). RISC assembly is thought to be governed by an enzyme that selects which strand of a dsRNA Dicer product is loaded into RISC. This strand is usually the one whose 5' end is less tightly paired to its complement. There also appears to be a clear bias for A, and to a lesser extent U, at the 5' position to facilitate binding to some argonaute proteins (Schwarz D S et al., 2003; Frank F et al., 2010).

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

It has been discovered by the current inventors that sequences within genes associated with pain ('pain associated genes') may be silenced to ameliorate pain. The present inventors target these pain associated genes in spinal cord neurons to ameliorate pain, particularly chronic pain, and even more particularly, chronic pain of neuropathic origin. Preferably, the pain associated gene is one or both of protein kinase C-γ (PKCγ) and D-amino acid oxidase (DAO).

In one aspect of the invention, there is provided a DNA-directed RNA interference (ddRNAi) agent (being an RNA molecule), and an expression cassette or construct to express that agent in a cell (including in vivo), for inhibiting, preventing or reducing expression of a pain associated gene, where the agent comprising, in a 5' to 3' direction, a first effector sequence (described further below) of at least 17 nucleotides in length, preferably 17 to 30 nucleotides in length, and more preferably 17 to 21 nucleotides in length, a first effector complement sequence, wherein the first effector complement sequence is substantially complementary to the first effector sequence, and wherein the effector sequence complementary to or substantially complementary to a predicted RNA target sequence transcribed from a DNA target sequence.

Within the transcribed sequence is a target region. Typically, a target region is a region of an mRNA of the gene that is intended to be silenced or to have its expression (at the level of transcription or translation) reduced, inhibited or prevented. In the current invention, the target region is transcribed from a target sequence and the target region consists of any 10 or more contiguous nucleotides within any one of SEQ ID NOS: 1-18, and preferably SEQ ID NOS: 3 to 5.

In other words, the effector sequence is directed to a target region of a target RNA sequence, wherein the target RNA sequence is a transcript of a target gene. The effector sequence is 'directed to' a target region by being substantially complementary (as 'substantially complementary' is defined below) in sequence to a transcript from a target gene containing the target region. An RNAi agent, such as a ddRNAi agent, having a double-stranded portion containing the effector sequence, can therefore inhibit expression of a target gene sequence by virtue of the target gene sequence containing the target region. Accordingly, within a cell having a pain associated gene, the RNAi agent is capable of inhibiting expression of a target gene sequence because the sequence of the effector (as 'effector' is defined below) is substantially complementary to (at least) a region of the predicted mRNA target sequence of the target gene. This can be illustrated by considering the following random, hypothetical short sequence:

5'ATTGCG3'—DNA target sequence of gene
5'AUUGCG3'—mRNA target region/sequence from transcription of the gene
3'UAACGC5'—effector sequence—which is substantially complementary to a region of the predicted mRNA target sequence.

As can be seen in the comparison above, substantial complementarity can be 100% complementarity. However as more particularly explained and defined further below, substantial complementarity can be 85% complementary. So in an effector sequence having a length of, for example, 20 nucleotides, the effector sequence is substantially complementary to the predicted mRNA target sequence if 17 of the 20 nucleotides are complementary ie 85% complementarity.

As would be appreciated, the target sequence will typically be longer than the effector sequence. Accordingly, when considering substantial complementarity between an effector sequence of, for example, 20 nucleotides, the 80-100% complementarity will be across a region of the target sequence of similar length.

The RNAi agent is designed so that it also comprises an effector complement sequence, ie a sequence that is substantially complementary to the effector sequence such that it will tend to anneal so as to form a double stranded RNA segment. The concept of substantial complementarity described in the paragraphs above applies equally to the substantial complementarity between the effector sequence and effector complement sequence where substantial complementarity can be 80% to 100% complementarity. Moreover, usually one end of the double stranded segment will be linked by a loop sequence so as to form a 'hairpin' shaped structure. This is also know as an 'interrupted inverted repeat' structure, as the DNA encoding such an RNA sequence contains an inverted repeat of the region of the target gene that is transcribed to the effector sequence, interrupted by a stuffer or spacer sequence encoding the loop.

In a preferred embodiment of the invention, the double stranded region formed by the effector sequence and its complement is expressed as part of a microRNA (miRNA) structure similar to the structure of endogenous miRNAs which are a natural substrate for endogenous RNAi processing pathways. Processing of double stranded RNAs expressed from ddRNAi constructs can be imprecise, and can result in toxicity. McBride et al. (2008) designed "artificial miRNA" constructs which expressed sequences from the base and loop of endogenous miRNAs, and suggested that more precise processing of expressed shRNAs from the miR-backbone led to reduced toxicity from the constructs. Wu et al. (2011) showed that mismatched duplexes (containing mismatches in the passenger strand) sometimes showed increased silencing activity, due possibly to their greater structural resemblance to endogenous miRNAs.

In one aspect of the invention, there is provided a ddRNAi agent and an expression cassette to express that agent in a cell within and as part of a miRNA structure, for inhibiting, preventing or reducing expression of a pain associated gene, where the agent comprises an effector sequence of at least 17 nucleotides in length complementary to or substantially complementary to a predicted sequence transcribed from a target region, and an effector complement sequence substantially complementary to the effector sequence.

The effector sequence and the effector complement sequence are therefore expressed within and as part of a miRNA structure. The target region may be selected from the group consisting of any 10 or more contiguous nucleotides within a sequence from any one of SEQ ID NOS: 1-18.

In some forms of the invention, the agent has more than one effector sequence. Multiple effectors may target the same region of a pain associated gene (typically variants of the same region), different regions of a pain associated gene, more than one pain associated gene, or a combination of all of the above.

Usually RNAi agents, such as ddRNAi agents, contain 1, 2 or 3 effector sequences. As explained above, the ddRNAi agent comprises an effector complement sequence for each effector sequence, thus forming effector-effector complement pairs (ie a first effector-first effector complement pair, a second effector-second effector complement pair, etc). These pairs may be, but need not be, contiguous to one another, as long as the RNAi agent can fold so as to permit each pair to anneal.

Various other considerations suggest one order or another of the effectors and effector complements along the length of the RNAi agent. In addition, as would be understood by one skilled in the art, and as illustrated in the Figures, any particular effector sequence may be swapped in position with its complement in the agent. The important feature, as exemplified in the various embodiments below, is that each effector sequence is able to anneal with its complement to form a double stranded region. For example:
  ddRNAi agent comprising, in a 5' to 3' direction, a first effector sequence; a second effector sequence; second effector complement sequence; and a first effector complement sequence;
  a ddRNAi agent comprising, in a 5' to 3' direction, a first effector sequence; a second effector sequence; a third effector sequence; a third effector complement sequence; a second effector complement sequence; and a first effector complement sequence;
  a ddRNAi agent comprising, in a 5' to 3' direction, a first effector; a first effector complement sequence; a second effector sequence; and a second effector complement sequence;
  a ddRNAi agent comprising, in a 5' to 3' direction, a first effector sequence; a first effector complement sequence; a second effector sequence; a second effector complement sequence; a third effector sequence; and a third effector complement sequence;
  a ddRNAi agent comprising, in a 5' to 3' direction, a first effector sequence; a second effector sequence; a sequence of 2 to 100 non-self-complementary nucleotides; a second effector complement sequence; and a first effector complement sequence;
  a ddRNAi agent comprising, in a 5' to 3' direction, a first effector sequence; a sequence of 2 to 100 non-self-complementary nucleotides; a first effector complement sequence; a second effector sequence; a sequence of 2 to 100 non-self-complementary nucleotides; and a second effector complement sequence.

In each of these embodiments, the effector complement sequence is substantially complementary to its corresponding effector sequence. Moreover, in each of these embodiments, the effector sequence and its complement, as well as any additional sequence such as a sequence of 2 to 100 non-self-complementary nucleotides, is optionally expressed within or part of a miRNA structure.

In particular forms of each of the embodiments described above, each effector sequence is at least 17 nucleotides in length, preferably 17 to 30 nucleotides in length, and more preferably 17 to 21 nucleotides in length and comprises a nucleotide sequence selected from the group consisting of any 10 or more contiguous nucleotides from a sequence from any one of SEQ ID NOS: 19-36. The effector sequences may all be the same, or may all be different, or may be a combination, e.g. 2 effector sequences of at least 10 contiguous nucleotides of SEQ ID NO:21 and one effector sequence of at least 10 contiguous nucleotides of SEQ ID NO: 22.

Preferably, the effector sequence is selected from the group consisting of any contiguous 11, 12, 13, 14, 15 or 16 nucleotides within any one of SEQ ID NOS: 19-36, and most preferably 17 or more contiguous nucleotides within any one of SEQ ID NOS: 19-36. Typically, the effector complement will be the same length, or about the same length (ie ±15% nucleotide length, or 1 to 3 nucleotides different depending on the overall length) as its corresponding effector sequence.

In particular embodiments the ddRNAi agent "consists of" or "consists essentially of" a nucleotide sequence selected from the group consisting of any one of SEQ ID NOS: 19 to 36 inclusive. In these embodiments, a ddRNAi agent having effector sequences of precisely SEQ ID NOS: 19-36 as well as a couple or a few (ie 1, 2 or 3) additional nucleotides or other chemical modifications would "consist essentially of" SEQ ID NOS: 19-36 as long as it exhibits activity for inhibiting, reducing or preventing the expression of a pain associated gene, as may be determined in accordance with the assays described below. Similarly, an RNAi agent "consists essentially of" one of SEQ ID NOS: 19-36 where it is shorter than the corresponding SEQ ID as long as it exhibits activity for inhibiting, reducing or preventing the expression of a pain associated gene, as may be determined in accordance with the assays described below.

In other embodiments, a ddRNAi agent of the invention comprises a nucleotide sequence that is 60, 70, 80, 90, 91, 92, 93, 94, 95, 96, 97, 98, 99 or 100% identical to a nucleotide sequence selected from the group consisting of SEQ ID NOS: 19-36. In other embodiments, the ddRNAi agent consists essentially of a sequence according to SEQ ID NOS: 1 to 18. In some embodiments, the ddRNAi agent consists of a sequence according to SEQ ID NOS: 19-36.

In alternative embodiments, the dsRNA is comprised of 2 separate RNA strands that are annealed to form a duplex. That duplex may then be embedded in a miRNA backbone.

Each effector sequence in each of the embodiments of the invention is preferably selected from SEQ ID NOS: 19 to 26, and more preferably SEQ ID NOS: 21 to 23. In one embodiment, wherein there are 3 effector sequences, each effector sequence is independently selected from SEQ ID NOS: 21 to 23. A preferred embodiment comprises 3 effector sequences, with one each of SEQ ID NO: 21, 22 and 23.

ddRNAi agents may be expressed from a DNA expression cassette inserted into any suitable vector or ddRNAi construct. Accordingly, in aspects of the invention there is provided a ddRNAi expression cassette comprising:
  one or more promoter sequences
  one or more DNA sequences, preferably being sequences that encode for any 10 or more and preferably any 17 or more contiguous nucleotides within a sequence from any one of SEQ ID NOS: 19-36,
  one or more DNA sequences that encode for one or more effector complement sequences;
and optionally
  one or more DNA sequences that encode for loop sequences; and
  one or more terminator sequences
  one or more enhancer sequences.

In some embodiments, one promoter is operably linked to multiple effector-encoding regions such that it can drive expression of them, whereas in other embodiments, each effector-encoding region is operably linked to its own promoter. In constructs where there are multiple promoters, these may be all the same or different. Preferred promoters are pol III promoters such as U6 and H1; other promoters such as neuronal-specific pol II promoters including Thy1 and H1xb9 (Wang et al, 2011) can also be used to drive expression of ddRNAi constructs.

In embodiments where the effector sequence and its complement, are expressed within a miRNA structure, the ddRNAi expression cassette additionally comprises sequences that encode, for the miRNA structure referred to herein as miRNA encoding (ME) sequences. The ME sequences may also encode for loop sequences or regions of loop sequences.

There is also provided ddRNAi expression constructs, into which the ddRNAi expression cassettes are inserted for expression. In addition, when the vector backbone of the construct is compatible with a delivery system, the ddRNAi expression constructs are also delivery constructs. The expression cassette further comprises ME sequence when the ddRNAi agent is to be expressed as part of or within a miRNA structure.

The invention also provides for siRNA agents that comprise a sequence of at least 17 nucleotides in length, preferably 17 to 30 nucleotides in length, and more preferably 17 to 21 nucleotides in length selected from the group consisting of any 10 or more contiguous nucleotides within a sequence from any one of SEQ ID NOS: 19-36 and a sequence complement with which the sequence forms a duplex, and that are capable of inhibiting expression of a pain associated gene.

In accordance with some embodiments, there is provided a method of inhibiting the expression of an mRNA or polypeptide encoded by a pain associated gene in a subject comprising administering to the subject a composition of the invention comprising a ddRNAi agent as described above. A ddRNAi expression cassette or ddRNAi expression construct of the invention for expressing the ddRNAi agent may also be administered.

In another embodiment the invention provides a composition for the treatment or prevention of pain in a subject (and/or the other conditions identified above as suitable for treatment) comprising as an active ingredient a ddRNAi agent, ddRNAi expression cassette or ddRNAi expression construct of the invention.

In another embodiment the invention provides a pharmaceutical composition comprising an effective amount of a ddRNAi agent, ddRNAi expression cassette or ddRNAi expression construct of the invention as a main ingredient. The composition may be used for example for the treatment or prevention of pain in a subject and/or the other conditions identified throughout as suitable for treatment. In some embodiments, the composition further comprises a pharmaceutically acceptable carrier or diluent.

In another embodiment the invention provides a ddRNAi agent, ddRNAi expression cassette or ddRNAi expression construct of the invention for use in the treatment or prevention of pain in a subject and/or the other conditions identified herein as suitable for treatment.

In another embodiment the invention provides a composition comprising a ddRNAi agent, ddRNAi expression cassette or ddRNAi expression construct of the invention for use in the treatment or prevention of pain in a subject. In some embodiments, the composition further comprises a pharmaceutically acceptable carrier or diluent.

In another embodiment, the invention provides a ddRNAi agent, ddRNAi expression cassette or ddRNAi expression construct in the preparation of a medicament for the treatment or prevention of pain in a subject.

In a further aspect, the present invention provides a kit of parts including (a) a ddRNAi agent, ddRNAi expression cassette or ddRNAi expression construct or composition of the invention; (b) a pharmaceutically acceptable carrier or diluent; and (c) a label or package insert with instructions for use in the methods of the invention described herein.

Another aspect of the invention provides a method for treating or preventing pain in a subject having or suspected of being at risk for having pain, such as the pain resulting from pain disorders as described herein, comprising administering to the subject a ddRNAi agent, ddRNAi expression cassette or ddRNAi expression construct or composition of the invention thereby treating or preventing pain.

Yet a further aspect of the invention provides a method for reducing the severity of pain in a subject, comprising administering to the subject a ddRNAi agent, ddRNAi expression cassette or ddRNAi expression construct or composition of the invention thereby reducing the severity of pain.

In this regard, the present invention contemplates the use of a ddRNAi agent, ddRNAi expression cassette or ddRNAi expression construct or composition in the context of pain resulting from pain disorders, including, but not limited to, primary erythermalgia (PE), paroxysmal extreme pain disorder (PEPD), acute or chronic pain, inflammatory diseases, nociceptive pain, neuropathic pain, inflammatory pain, non-inflammatory pain, painful hemorrhagic cystitis, pain associated with the herpes virus, pain associated with diabetes, peripheral neuropathic pain, central pain, deafferentiation pain, chronic nociceptive pain, stimulus of nociceptive receptors, phantom and transient acute pain, peri-operative pain, cancer pain, pain and spasticity associated with multiple sclerosis, central pain, deafferentiation pain, arachnoiditis, radiculopathies, neuralgias, somatic pain, deep somatic pain, surface pain, visceral pain, acute pain, chronic pain, breakthrough pain, chronic back pain, failed back surgery syndrome, fibromyalgia, post-stroke pain, trigeminal neuralgia, sciatica, pain from radiation therapy, complex regional pain syndromes, causalgia, reflex sympathetic dystrophy, phantom limb pain, myofascial pain, pain associated with burns and phantom and transient acute pain and/or other disease states, conditions, or traits associated with pain associated gene expression or activity in a subject or organism.

A subject in need of treatment by a method of the invention is suffering from or likely to suffer from any one or more of the pain disorders described herein. The invention is particularly useful in providing a method of treating or preventing pain in a cancer patient, including in a cancer patient also receiving treatment for the cancer itself.

In another embodiment, the invention provides a method for increasing the sensitivity of a subject in need of pain relief, or rendering a subject in need of pain relief sensitive to, treatment with other pain relievers, such as opiates including morphine. The method involves administering a ddRNAi agent, ddRNAi expression cassette or ddRNAi expression construct or composition of the invention to a subject who is no longer responsive to other pain relief due to resistance or tolerance of the analgesic effects.

Although the invention finds application in humans, the invention is also useful for veterinary purposes. The invention is useful for the treatment or prevention of pain or a symptom of pain, as described herein, in domestic animals such as cattle, sheep, horses and poultry; companion animals such as cats and dogs; and zoo animals.

BRIEF DESCRIPTION OF THE DRAWINGS/FIGURES

FIG. 1A-G illustrates some of the ddRNAi agent structures of the invention.

FIG. 2: A. Diagrammatic representation of ddRNAi expression cassette. Expression of shRNAs was driven by the U6 promoter (black arrow); the shRNAs were in the form effector complement (grey arrow), loop (white arrow) then effector sequence (grey arrow). Transcripts were terminated using the pol III terminator sequences TTTTTT. B. Predicted shRNAs expressed by the indicated constructs are shown, SEQ ID NOS refer to target sequence and effector sequences listed in Table 2. RNA sequences of the predicted effector sequences are shown in bold and underline in the shRNA. Sequences predicted to be specified by pol III termination are shown as uu.

Figure 3:
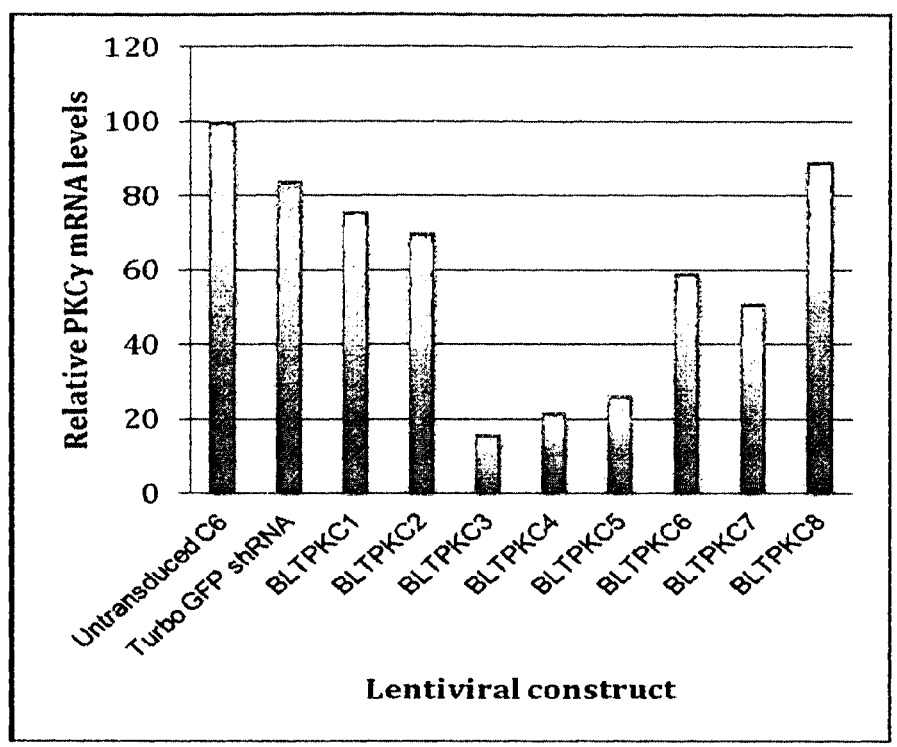

FIG. 3: Relative expression levels of PKCγ mRNA in rat C6 cells transduced with the indicated lentiviral constructs.

FIG. 4: Predicted shRNAs expressed by the indicated constructs targeting rat (A) and human (B) DAO mRNAs are shown. SEQ ID NOS refer to target sequence and effector sequences listed in Table 2. RNA sequences of the predicted effector sequences are shown in bold and underline in the shRNA. Sequences predicted to be specified by pol III termination are shown as uu.

FIG. 5: Diagrammatic representations for constructs BOPKC3 (A) and BOPKC3&4 (B), BOPKC3cont (C) and BOPKC3&4cont (D), together with predicted sequences of shRNAs. RNA sequences of the predicted effector sequences are shown in bold and underline in the shRNA. Sequences predicted to be specified by pol III termination are shown as uu. BOPKC3 and BOPKC3cont contain an additional sequence (U61 term) derived from sequences downstream of the human U61 terminator region. BOPKC3 (SEQ ID NO: 45) targets SEQ ID NO:3 with an effector sequence of SEQ ID NO:21, and BOPKC3&4 (SEQ ID NO: 46) targets SEQ ID NOS:3 and 4 with an effector sequence of SEQ ID NO:21 and 22. The two control constructs were designed to express randomised shRNAs based on BOPKC3 and BOPKC3&4 and are designated BOPKC3cont (SEQ ID NO:47) and BOPKC3&4cont (SEQ ID NO:48).

FIG. 6: A. Diagrammatic representation of ddRNAi expression cassette expressing an RNAi agent embedded in a miRNA structure. The black arrow denotes a U6 promoter; grey arrows denote effector complement and effector sequences and white arrows denote sequences derived from miRNA sequences; terminator sequences are also indicated. B. Predicted sequence of RNA expressed from BLTPKRC3miR. The underlined sequences are derived from the base of human miR30a pre-cursor RNA (both 5' and 3'); sequences in italics are derived from the loop sequences of miR30a. The upper case sequences indicate the predicted passenger strand sequence; the bold uppercase sequences denote the predicted effector sequence. Predicted secondary structure of this RNA, determined using the M-fold programme (http://mfold.rna.albany.edu) is shown below this; predicted Dicer and Drosha processing sites are indicated by arrows, processed RNAs from this are predicted to express the effector sequence SEQ ID NO: 21 targeting a SEQ ID NO: 3 in PKC$_\gamma$ mRNA. C. Predicted sequence of RNA expressed from BLTPKRC4miR shown as in 6B, The predicted secondary structure and processing sites of this RNA are also shown, processed RNAs from this are predicted to express the effector sequence SEQ ID NO: 22 targeting a SEQ ID NO: 4 in PKC$_\gamma$ mRNA.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, the following definitions will apply and whenever appropriate, terms used in the singular will also include the plural and vice versa. In the event that any definition set forth conflicts with any document incorporated herein by reference, the definition set forth below shall prevail.

DEFINITIONS

As used herein, except where the context requires otherwise, the term "comprise" and variations of the term, such as "comprising", "comprises" and "comprised", are not intended to exclude further additives, components, integers or steps.

The term "RNA interference" or "RNAi" refers generally to a RNA dependent gene silencing process that is initiated by double stranded RNA (dsRNA) molecules in a cell's cytoplasm. The dsRNA reduces the expression of a target nucleic acid sequence, which may be a DNA whose RNA expression products are reduced, or an RNA, with which the dsRNA molecule shares substantial or total homology.

By "double stranded RNA" or "dsRNA" it is meant a double stranded RNA molecule that is capable of inhibiting expression of a target nucleic acid sequence with which it shares homology. In some embodiments the dsRNA is a hairpin or stem loop structure, with a duplex region optionally linked by at least 1 nucleotide, and is referred to as a "hairpin RNA" or "short hairpin RNAi agent" or "shRNA". The duplex is formed between an effector sequence and a sequence complementary to the effector sequence herein referred to as an "effector complement". Typically, the effector complement will be the same length as its corresponding effector sequence. As will be explained below, the effector sequence is complementary to the target nucleic acid sequence.

An "effector sequence" is the nucleotide sequence that, when part of the RISC complex, binds to the pain associated gene target nucleotide sequence, thereby targeting that sequence for destruction by the cell. It is analogous to the "guide" strand discussed in the background section. The effector sequence is 'directed to' a target region by being complementary or substantially complementary in sequence to the transcript from the target region such that an RNA agent having a double stranded portion containing the effector sequence inhibits expression of the target gene sequence.

The "effector complement", which is analogous to the passenger strand discussed in the background is of sufficient complementary to the effector such that is anneals to the effector sequence. It is likely that the effector complement will be of a similar sequence to the target gene sequence, but does not necessarily have to be.

The sequences of the ddRNAi agents of the invention have to have a sufficient identity to the pain-associated gene such as the PKCγ or DAO gene in order to mediate target specific RNAi. By "substantially complementary" it is meant that the sequences are hybridisable or annealable (as further defined below), and either:

the sequence of the first effector sequence is at least about 80, 81, 82, 83, 84, 85, 86, 87, 88, 89 or 90% complementary to at least 17 or more contiguous nucleotides of the target sequence, more preferably at least about 90, 91, 92, 92, 94 or 95% complementary and even more preferably at least about 95, 96, 97, 98 or 99% complementary or absolutely complementary (ie 100%) to 17 or more contiguous nucleotides of the target sequence. For example, if the target region within a target sequence is 20 nucleotides long, and the effector sequence is 20 nucleotides long, then the effector sequence may have, for example, 16, 17, 18 or 20 nucleotides that are complementary with the target, equating to 80%, 85%, 90% and 100% complementarity respectively; or the effector sequence has at least 10 or more contiguous nucleotides that are 100% complementary with the target and preferably less than 6 nucleotides that cannot base pair with the target sequence. The first effector sequence can therefore have 1, 2, 3, 4 or 5 nucleotides that will not G-C/A-U base pair with the target sequence. It is believed that this level of difference will not negatively impact on the ability of the ddRNAi agent to be able to inhibit expression of the target sequence. When the first effector sequence does have 1, 2, 3, 4 or 5 nucleotides that will not G-C/A-U base pair with the target sequence, it is preferred that the differences are in the first or last 5 nucleotides of the first effector sequence, with only 1 or 2 nucleotide changes in the centre portion of the effector sequence.

Substantially complementary is preferably about 85% complementary to a portion of the target gene. More preferably, it is at least 85-90% complementary, and most preferably at least 95, 96, 97, 98 99 or 100% complementary. Substantial complementarity therefore includes 100% complementarity, but 100% complementarity may also be referred to throughout the specification as "complementary", or "being complementary".

As noted earlier in the specification, the concept of substantial complementarity described in the paragraphs above applies equally to the substantial complementarity between the effector sequence and effector complement sequence where substantial complementarity can be 80% to 100% complementarity.

Whether in the context of substantial complementarity between the effector and target, or effector and its complement, one will appreciate that substantial complementarity may not equate to a whole number. For example, at least 85% complementarity to a sequence of 22 nucleotides would be 18.7 nucleotides, so is effectively a requirement for 19 of 22 to be complementary.

Alternatively, substantial complementarity of 80 to 100% complementarity (again, both in the context of substantial complementarity between the effector and target, and effector and its complement) can be described with reference to the number of nucleotides that will not G-C/A-U base pair (except for wobble pairs as described below). For example, in an effector sequence of 20 nucleotides, there may be 2, 3, 4 or 5 nucleotides within the complementary region between the 2 RNAs that are not themselves complementary with a nucleotide in the effector sequence when considering at least 80% complementarity across a nucleotide sequence (whether due to mismatched or unmatched nucleotides). As to whether there can be 1, 2, 3, 4 or 5 nucleotides that do not base pair is dependent on the length of the relevant sequence. For example, if the effector sequence is 17 nucleotides long, it cannot have 5 nucleotides that will not base pair, as this would equate to only 71% complementarity. In a 17 nucleotide sequence, there must be complementarity between 14 of the 17 nucleotides for at least 80% complementarity.

Substantial complementarity therefore, in summary, may be described in terms of:

percentage identity (being 80 to 100%) between an effector and its complement, or between an effector and target sequence; or number of nucleotides that are not complementary provided that number is consistent with the percentage identity requirement of 80 to 100%.

As noted above, substantial complementarity is intended to mean that the sequences are hybridisable or annealable. The terms "hybridising" and "annealing" (and grammatical equivalents) are used interchangeably in this specification in respect of nucleotide sequences and refer to nucleotide sequences that are capable of forming Watson-Crick base pairs due to their complementarity. Preferably the substantially complementary sequences are able to hybridise under conditions of medium or high stringency:

high stringency conditions: 0.1×SSPE (or 0.1×SSC), 0.1% SDS, 65° C.

medium stringency conditions: 0.2×SSPE (or 1.0×SSC), 0.1% SDS, 50° C.

"Wobble pairs" can form between guanosine and uracil residues in RNA, and are non-Watson-Crick base-pairing. "Complementary" is used herein in its usual way to indicate Watson-Crick base pairing, and "non-complementary" is used to mean non-Watson-Crick base pairing, even though such non-complementary sequences may form wobble pairs or other interactions. In the context of the present invention, reference to "non-pairing" sequences relates specifically to sequences between which Watson-Crick base pairs do not form.

The term "RNAi agent" refers to a dsRNA sequence that elicits RNAi. This term may be used interchangeably with "small interfering RNAs" (siRNA agents) and small hairpin RNA (shRNAi or hpRNAi agents).

The "loop" of a hairpin structure is an additional sequence wherein at least some of the nucleotides are non-complementary to either itself, the target sequence, the effector sequence or the effector complement. The loop can be a sequence of 2 to 100 nucleotides which are capable of forming a loop. Not all of the nucleotides of the loop sequence need be non-annealed. For example, in a loop sequence of ACUGUGAAGCAGAUGAGU, nucleotides ACU may be annealed with AGU, while the intervening GUGAAGCAGAUG sequence remains non-annealed.

In embodiments in which the ddRNAi agent is expressed as part of a miRNA structure, the loop sequence may be derived or partially derived from the miRNA, and is encoded by the ME sequence.

A "microRNA" or "miRNA" is a small non-coding RNA molecule which may occur naturally in organisms and function in the post-transcriptional regulation of gene expression. miRNA transcripts are capable of forming hairpin-like structures; typically contain mismatches and bulges within or adjacent to the double stranded RNA regions. The miRNA structure in which the ddRNAi agents of the invention are preferably expressed contains mismatches and insertions, as detailed above. Wu et al. (2011) showed that mismatched duplexes (containing mismatches in the passenger strand) sometimes showed increased silencing activity, due possibly to their greater structural resemblance to endogenous miRNAs. Similarly Gu et al. (2012) showed the introduction of bulges adjacent to loop sequences in shRNA molecules can result in increased precision of Dicer processing.

In the double stranded, folded miRNA structure, at least 50% of the nucleotides on one strand are annealed to nucleotides of the other strand. Of the non-annealed (ie unpaired) nucleotides, they may be insertions or deletions ie they lack a complementary nucleotide on the opposing strand, or they may be mismatches such that they do not anneal, for example, a G and an A: The double stranded, folded miRNA structure can contain 2 or more annealed nucleotides, separated by 1 or more non-annealed nucleotides, to give a double stranded RNA structure with "bubbles" or "bulges" where the nucleotides are not annealed. The requirement for at least 50% of the nucleotide to be annealed applies to the entire length of each strand. However, as can be seen in the illustrations of a miRNA structure in, for example, FIGS. 1G, 6A and 6B, most of these unpaired nucleotides within the miRNA structure are outside of the effector-effector complement region. While overall only 50% of nucleotides on one strand must anneal with those on the other strand, the effector/effector complement portion of the miRNA structure must retain at least 80% complementarity, as defined herein.

By "miRNA encoding sequence" or "ME sequence", it is meant the DNA sequence contained within a ddRNAi expression cassette that encodes for RNA which is capable of folding in to a miRNA structure. The effector sequence and the effector complement of a ddRNAi agent are expressed within and as part of that miRNA structure. The ME sequence has a first and second part. In an expression cassette for expressing a single hairpin (having one or more effector/effector complement pairs), the first part of the ME sequence is located upstream (ie 5') of the 5' most effector or effector complement encoding sequence, and the second part is located downstream (ie 3') to the 3' most effector or effector complement encoding sequence.

In the case of an expression cassette for a multiple hairpin structure, each effector/effector complement pair has a corresponding first and second ME sequence, wherein the first ME sequence is upstream of the effector or effector complement encoding sequence and the second part is downstream of the corresponding effector or effector complement encoding sequence. In an expression cassette having the following exemplary structure, in a 5' to 3' direction:

a promoter
a first ME sequence;
a first effector;
a first effector complement sequence;
a second ME sequence;
a third ME sequence;
a second effector sequence;
a second effector complement sequence; and
a fourth ME sequence It will be appreciated that the second and third ME sequence can either be (using exemplary sequences to illustrate the point) consecutive, can have intervening sequence between them, or can be a single ME sequence that serves the same function as the second and third ME sequence.

```
i) consecutive:
ggtatattgctgttgacagtgagcga
    ME sequence 2
ggtatattgctggggacagtgagccc
    ME sequence 3 ii) intervening:
ggtatattgctgttgacagtgagcgaATTGCCATG
    ME sequence 2        INTERVENING
ggtatattgctggggacagtgagccc
    ME sequence 3 iii) single:
ggtatattgctgttgacagtgagcgaggtatattg
ctggggacagtgagccc
                ME sequence
```

The double stranded or duplex region of the RNAi agent is at least 17 base pairs long, and usually in the range of 17 to 30 base pairs and preferably 17 to 21 base pairs. RNAi agents can be synthesized chemically or enzymatically outside of cells and subsequently delivered to cells or can be expressed in vivo by an appropriate vector in cells (see, e.g., U.S. Pat. No. 6,573,099, WO 2004/106517 and WO99/49029, all of which are incorporated herein by reference).

The term "DNA-directed RNAi agent" or "ddRNAi agent" refers to an RNAi agent that is transcribed from a DNA expression cassette ("ddRNAi expression cassette"). The ddRNAi agent transcribed from the expression cassette may be transcribed as a single RNA that is capable of self-annealing into a hairpin structure with a duplex region linked by at least 2 nucleotides, or as a single RNA with multiple shRNA domains or as multiple transcripts each capable of folding as a single shRNA.

The ddRNAi expression cassette can be ligated into vectors referred to as ddRNAi vectors or ddRNAi constructs. The vectors may provide sequences specifying transcription of the ddRNAi expression cassette in vivo or in vitro. The vector may additionally serve as the delivery vehicle for the ddRNAi expression cassette. Viral based vectors for example will generate a ddRNAi construct that is useful for expression of the ddRNAi expression cassette as well as being compatible with viral delivery.

A cell has been "transformed", "transduced" or "transfected" by an exogenous or heterologous nucleic acid or vector when such nucleic acid has been introduced into the cell. The transforming DNA may or may not be integrated (covalently linked) into the genome of the cell. With respect to eukaryotic cells, a stably transformed cell is one in which the transforming DNA has become integrated into a host cell chromosome or is maintained extra-chromosomally (episomally) so that the transforming DNA is inherited by daughter cells during cell replication. In non-replicating, differentiated cells the transforming DNA may persist as an episome.

"Gene expression" can be a reference to either or both transcription or translation.

"Inhibition of expression" refers to the absence or observable decrease in the level of protein and/or mRNA product from the target gene. The inhibition does not have to be absolute, but may be partial inhibition sufficient for there to a detectable or observable change as a result of the administration of a RNAi or ddRNAi agent or siRNA agent or ddRNAi expression cassette or expression construct of the invention. Inhibition may be measured by determining a decrease in the level of mRNA and/or protein product from a target nucleic acid relative to a cell lacking the ddRNAi agent or construct, and may be as little as 1%, 5% or 10%, or may be absolute ie 100% inhibition. The effects of inhibition may be determined by examination of the outward properties ie quantitative and/or qualitative phenotype of the cell or organism.

"Off-target" effects is a term used to describe unintentional side-effects of treatment with an RNAi reagent. This is frequently thought to involve unintended knockdown of a target sequence as a consequence of chance homology with the passenger or effector sequences and another target gene, although subtler effects arising from metabolic compensation of a knockdown can also occur. Processing of miRNAs by endogenous RNAi pathways frequently results in the loading of only the effector strand into RISC, and degradation of the passenger strand. One potential source of off-target effects is the unanticipated incorporation of the passenger strand into RISC such that passenger sequences can consequently silence genes which they fortuitously share homology with. There is evidence that a step in RISC loading "senses" the predicted thermodynamic stability of an RNA duplex across a potential target site in dsRNA precursors and preferentially loads the strand whose 5' end is from the less stable end of the duplex. One strategy to minimise the potential for off-target effects is to screen ddRNAi molecules for activity of the passenger strand using Dual Luciferase assays. Loading of this strand into RISC is undesirable.

As used herein, a "protein kinase C γ gene" or "PKCγ gene", includes a gene that encodes a protein having protein kinase C γ activity. In one embodiment the PKCγ gene encodes a nucleotide sequence as shown in Genbank with accession number NM_002739 (SEQ ID NO:37) which encodes human PKCγ. In another embodiment, a PKCγ gene is an orthologous or paralogous gene to the PKCγ gene, including but not limited to a nucleotide sequence as shown in Genbank with accession number NM_012628 (rat PKCγ; SEQ ID NO: 38), XM_541432 (dog PKCγ; SEQ ID NO: 39), and AB169802 (macaque PKCγ; SEQ ID NO: 40). In another embodiment, the PKCγ gene encodes a protein that falls within the IUBMB enzyme nomenclature classification of E.C.1.4.3.3. In yet a further embodiment, a PKCγ gene may be a human gene or gene from an animal as described herein and includes allelic variants.

As used herein, a "D-amino-acid oxidase gene", or "a DAO gene" includes a gene that encodes a protein having D-amino acid oxidase activity. In one embodiment the DAO gene encodes a nucleotide sequence as shown in Genbank with accession number NM_001917 (SEQ ID NO: 41) which encodes human DAO. In another embodiment, a DAO gene is an orthologous or paralogous gene to the DAO gene, including but not limited to a nucleotide sequence as shown in Genbank with accession number NM_053626 (rat DAO; SEQ ID NO: 42), XM_543443 (dog DAO; SEQ ID 43) and AK240621 (macaque DAO; SEQ ID 44). In another embodiment, the DAO gene encodes a protein that falls within the IUBMB enzyme nomenclature classification of E.C.1.4.3.3. In yet a further embodiment, a DAO gene may be a human gene or gene from an animal as described herein and includes allelic variants.

Sequences are "paralogous" if they are separated by a gene duplication event: if a gene in an organism is duplicated to occupy two different positions in the same genome, then the two copies are paralogous.

Sequences are "orthologous" if they are separated by a speciation event: when a species diverges into two separate species, the divergent copies of a single gene in the resulting species are said to be orthologous.

As used herein, "a quantitative phenotypic trait" refers to a trait associated with the molecular expression of a nucleic acid in a host cell and may thus include the quantity of RNA molecules transcribed or replicated, the quantity of post-transcriptionally modified RNA molecules, the quantity of translated peptides or proteins, or the activity of such peptides or proteins.

A reduction of phenotypic expression of a nucleic acid where the phenotype is a qualitative trait means that in the presence of the RNAi agent of the invention, the phenotypic trait switches to a different state when compared to a situation in which the RNAi agent is absent. A reduction of phenotypic expression of a nucleic acid may thus be measured as a reduction in steady state levels of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a nucleic acid of interest may be accompanied by or correlated to an observable change in phenotype. The assessment may be by way of biochemical techniques such as Northern hybridisation, quantitative real-time PCR assays, gene expression assays, antibody binding, ELISA, RIA, western blotting and other assays and techniques known in the art.

"Target nucleic acids" may be either RNA or DNA, whose transcription products are targeted, coding or non-coding sequence, endogenous or exogenous.

A "therapeutic composition" or "pharmaceutical composition" or "composition for treating pain" refers to a composition including a ddRNAi agent, ddRNAi expression cassette, ddRNAi construct or siRNA agent.

The words "treat" or "treatment" refer to therapeutic treatment wherein the object is to slow down (lessen) an undesired physiological change or disorder. For purposes of this invention, beneficial or desired clinical results include, but are not limited to, alleviation of symptoms of chronic pain, stabilized (i.e., not worsening) pain management, and delay or slowing of pain onset.

The words "prevent" or "prevention" refer to therapeutic treatment wherein the object is to avoid an undesired physiological change or disorder from occurring. For purposes of this invention, prevention includes, but is not limited to, preventing the symptoms of and onset of chronic pain occurring, and stabilizing (i.e., not worsening) pain symptoms.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The current invention provides a new RNAi agent, and use of the RNAi agent for reducing pain in affected individuals. Treatment of pain is aimed at:

i. long-term knock down molecules in spinal cord neurones and/or glia involved in the transmission of chronic unmanageable pain using a DNA construct containing one or more sequences aimed at silencing specific genes associated with pain (pain associated genes) and ii. limiting the treatment to neurones and/or glia which transmit pain from the affected area in the individual patients.

A number of target genes have been defined in the literature as potential targets for RNAi therapeutics. Examples are listed in Table 1.

TABLE 1

Potential target genes for RNAi therapeutics

| Target | RNAi Method | Type of Pain | Reference |
|---|---|---|---|
| ATP receptor P2X3 | siRNA | neuropathic | Dorn et al, 2004 |
| NMDA receptor NR2B | siRNA | spontaneous | Tan et al, 2005 |
| NMDA receptor NR1 | ddRNAi | mechanical allodynia | Garraway et al, 2007 |
| MMP-2 & MMP-9 | siRNA | mechanical allodynia | Kawasaki et al, 2008 |
| K channel Kir4.1 | siRNA | neuropathic | Vit et al, 2008 |
| Capsaicin receptor TRPV1 | ddRNAi | mechanical allodynia | Christoph et al, 2008 |
| EP receptor EP4 (prostaglandin E2) | ddRNAi | nociceptive | Lin et al, 2006 |
| PKCγ | ddRNAi | neuropathic | Zou et al, 2011 |

Despite the recognition in the art that some pain associated genes may be suitable targets for silencing by RNAi techniques, identifying appropriate target sequences within those target genes, and designing RNAi agents that work based on those sequences, is not routine. As will be demonstrated in the results section, target sequences that look like good candidates on paper, may not necessarily effectively silence the target, or may not do so to an effective level for therapeutic purposes. Some effector sequences work much more effectively than others to silence a target, but it is not predictable which sequences are able to be silenced by mere visual inspection of the sequence itself, let alone to what extent they may be silenced, and if that would be sufficient for the purposes of the invention.

One target pain associated gene is protein kinase Cγ, or PKCγ. Protein kinase C (PKC) is a family of serine- and threonine-specific protein kinases that can be activated by calcium and second messenger diacylglycerol. PKC family members phosphorylate a wide variety of protein targets and are known to be involved in diverse cellular signaling pathways. Each member of the PKC family has a specific expression profile and is believed to play distinct roles in cells. PKCγ is expressed solely in the brain and spinal cord and its localization is restricted to neurons. Knockout studies in mice suggest that this kinase may be involved in pain development (Celerier et al 2004) and intrathecal delivery of lentiviruses targeting PKCγ have been shown to alleviate pain in rat pain models (Zou et al 2011).

An alternative target pain associated gene is the DAO gene. The DAO gene encodes the peroxisomal enzyme D-amino acid oxidase, which catalyses oxidative deamination of neutral and polar d-amino acids and is expressed in the kidneys, liver, and central nervous system (CNS) including the spinal cord. DAO in the spinal cord has been suggested to contribute significantly to the development of central sensitization-mediated pain (central sensitization is an increase in excitability of spinal and brain neurons after persistent nociceptive stimulation), suggesting DAO may be an important molecular target for the treatment of chronic pain of neuropathic origin (Zhao et a/2008, 2010).

RNA interference (RNAi) is an RNA-dependent gene silencing process that is initiated by short double-stranded RNA molecules in a cell's cytoplasm. In mammals, RNAi is mediated by double-stranded RNA molecules referred to as small interfering RNAs (siRNA). The double stranded, or duplex region of the RNAi agent is at least 17 base pairs long, and usually in the range of 17 to 30 base pairs and preferably 17 to 21 base pairs. RNAi agents can be synthesized chemically or enzymatically outside of cells and subsequently delivered to cells or can be expressed in vivo by an appropriate vector in cells (such as MV, lentivirus, or non-viral liposome-based delivery systems).

Pre-clinical testing of RNAi agents as pain therapeutics requires the extensive use of animal models. Rat (*Rattus norvegicus*) models are widely used to test the efficacy of treatments, and other species such as dogs (*Canis familiaris*) and primates (eg macaques, *Macaca fasciularis*) are commonly used as models to determine the clinical safety of therapeutic compounds. For RNAi therapeutics it is advantageous to design reagents that target nucleotide sequences of pain-associated genes that are highly conserved between humans and the various pre-clinical test species. Some target genes (eg PKCγ) are highly conserved between potential test species, whereas others (eg DAO) are poorly conserved. For highly conserved genes a single RNAi reagent can be used at all stages of pre-clinical testing since the reagent would be expected to silence the target gene in all species. For poorly conserved genes multiple RNAi reagents, with sequences that differ slightly between the different test species must be tested in parallel to accurately determine potential toxicity.

Accordingly, the RNAi reagents described in this application, are where possible designed to target sequences absolutely conserved between humans and the potential test species (rats, dogs and primates such as macaques), since this provides significant advantages for a drug development program.

ddRNAi Agent

RNAi agents may be expressed from DNA vectors, referred to as DNA-directed RNAi, or ddRNAi. They can directly target the activity of genes with minimum off-target events. In the case of chronic pain, this offers a unique opportunity to address the unmet clinical treatment needs. Accordingly, in one aspect of the invention, there is provided a DNA-directed RNA interference (ddRNAi) agent for inhibiting expression of one or more target sequences in a pain-associated gene, the ddRNAi agent comprising at least:

a first effector sequence of at least 17 nucleotides in length, preferably 17 to 30 nucleotides in length, and more preferably 17 to 21 nucleotides in length; and a first effector complement sequence, wherein the first effector complement sequence is substantially complementary to the first effector sequence;

and wherein the first effector sequence is substantially complementary to a predicted transcript of a region of the target gene.

Typically, the first effector sequence forms a double stranded region with the first effector complement sequence.

The ddRNAi agent may also comprise a first effector sequence consisting of 17, 18, 19, 20, 21, 22, 23, 24, 25, 26, 27, 28, 29, or 30 nucleotides in length, wherein the effector sequence is substantially complementary to a predicted transcript of a region of the target gene. A ddRNAi agent according to this embodiment of the invention therefore has a maximum length determined by the length and number of effector sequence/s ie each effector sequence is not comprised within a longer sequence.

The first effector sequence is at least 17 nucleotides long, preferably 17 to 30 nucleotides and most preferably 17 to 21 nucleotides. It may be 17, 18, 19, 20, 21, 22, 23, 24, 25, 26, 27, 28, 29 or 30 nucleotides in length. When the first effector sequence is longer than 17 nucleotides, it is preferred that at least 17 contiguous nucleotides of the first effector sequence forms the double stranded region with the complementary strand.

The ddRNAi agents of the invention inhibit expression of pain-associated target genes. Preferably the pain associated gene is one or both of protein kinase C-γ (PKCγ) and D-amino acid oxidase (DAO), and each effector sequence is selected from the group consisting of any 10 or more contiguous nucleotides within a sequence from any one of SEQ ID NOS: 19-36.

When the pain associated gene to be inhibited, prevented or reduced is PKCγ, each effector sequence is selected from SEQ ID NOS: 19-26. When the pain associated gene to be inhibited, prevented or reduced is DAO, each effector sequence is selected from SEQ ID NOS: 27-36.

Accordingly, in one embodiment of the invention, the ddRNAi agent of the invention inhibits expression of one or more target sequences in a PKCγ gene. A target sequence is preferably selected from the ddRNAi PKCγ target sequences listed in Table 2 below (SEQ ID NOS: 1-8); the corresponding effector sequences that would be produced by dicer processing of a ddRNAi agent targeting those sequences is shown in SEQ ID NOS: 19-26 respectively. Note that some of the PKC target (SEQ ID NOS: 3, 4, 6 and 8) and effector sequences (SEQ ID NOS: 21, 22, 24 and 26) have been chosen to show absolute conservation of nucleotide sequences between human and the pre-clinical test species rat, dog and macaque; the remainder are conserved between human, rat and macaque.

In an alternative embodiment of the invention, the ddRNAi agent of the invention inhibits expression of one or more target sequences in a DAO gene. A target sequence is preferably selected from the ddRNAi DAO target sequences listed in Table 2 below (SEQ ID NOS: 9-18); the corresponding effector sequences are therefore selected from SEQ ID NOS: 27-36 respectively as shown in Table 2.

TABLE 2

PKCγ and DAO gene target sequences and their corresponding ddRNAi effector sequences

| SEQ ID NO | Target[a] | Target position[b] | Target sequence in 5' to 3' direction[c] | SEQ ID NO | Corresponding effector sequence in 5' to 3' direction[d] |
|---|---|---|---|---|---|
| 1 | PKCγ | 1974-1993 | TGCAAGGGGTTCCTGACCAA | 19 | UUGGUCAGGAACCCCUUGCA |
| 2 | PKCγ | 1617-1636 | GGCCTCTTCTTCCTTCACAA | 20 | UUGUGAAGGAAGAAGAGGCC |
| 3 | PKCγ | 1266-1285 | GACTTCAGCTTCCTCATGGT | 21 | ACCAUGAGGAAGCUGAAGUC |
| 4 | PKCγ | 1107-1126 | AGCCTCCTCCAGAAGTTTGA | 22 | UCAAACUUCUGGAGGAGGCU |
| 5 | PKCγ | 1087-1106 | TGGCCGATGCTGACAACTGC | 23 | GCAGUUGUCAGCAUCGGCCA |
| 6 | PKCγ | 1061-1080 | GGAGGGCGAGTATTACAATG | 24 | CAUUGUAAUACUCGCCCUCC |
| 7 | PKCγ | 987-1006 | GGTGCCATGTCCTTTGGTGT | 25 | ACACCAAAGGACAUGGCACC |
| 8 | PKCγ | 1105-1124 | GCAGCCTCCTCCAGAAGTTT | 26 | AAACUUCUGGAGGAGGCUGC |
| 9 | DAOr | 826-845 | GGGAACTGGAGCGAGCTAAA | 27 | UUUAGCUCGCUCCAGUUCCC |
| 10 | DAOh | 886-905 | GGAAACTGGAGTGAACTAAA | 28 | UUUAGUUCACUCCAGUUUCC |
| 11 | DAOr | 685-704 | GGCCGGGGCCAGATCATCCA | 29 | UGGAUGAUCUGGCCCCGGCC |
| 12 | DAOh | 745-764 | GGCCGGGGGCAGATCATGAA | 30 | UUCAUGAUCUGCCCCCGGCC |
| 13 | DAOr | 613-632 | GGCGTGGATGTGATTATCAA | 31 | UUGAUAAUCACAUCCACGCC |
| 14 | DAOh | 673-692 | GGCGCAGACGTGATTGTCAA | 32 | UUGACAAUCACGUCUGCGCC |
| 15 | DAOr | 533-552 | GGCTGACTGAGAGGTTAACT | 33 | AGUUAACCUCUCAGUCAGCC |
| 16 | DAOh | 593-612 | GGCTGACTGAAAGGTTAACT | 34 | AGUUAACCUUUCAGUCAGCC |
| 17 | DAOr | 283-302 | GAGGCGGAGTGGAACCAGCA | 35 | UGCUGGUUCCACUCCGCCUC |
| 18 | DAOh | 343-362 | GAGGCGGACTGGAGCCAACA | 36 | UGUUGGCUCCAGUCCGCCUC |

[a]Target genes are PKCγ (rat, human, macaque and in some instances dog) or rat DAO (DAOr) or human (DAOh).
[b]Target positions for PKCγ are shown for rat sequence (NM_012628), positions for rat DAO targets (DAOr) are shown for the rat sequence (NM_053626), positions for human DAO targets (DAOh) are shown for the human sequence (NM_001917). A transcript from these target positions will contain the target region.
[c]Target sequences are the DNA sequences, the transcript of which is recognised by the effector sequence.
[d]Effector sequences are the predicted RNA sequences produced by dicer processing of the ddRNAi agents that target PKCγ or DAO mRNAs. Effector sequences are predicted to terminate with UU (these sequences are not shown).

In accordance with the explanation provided earlier, the relationship between the DNA target sequence and the corresponding effector sequence of the ddRNAi agent can be shown as (using the target SEQ ID NO:1 and its corresponding effector sequence SEQ ID NO:19 from Table 2):

```
                                            (SEQ ID NO: 1)
5' TGCAAGGGGTTCCTGACCAA 3'-DNA target sequence of
PKCγ

5' UGCAAGGGGUUCCUGACCAA 3'-predicted mRNA
transcript of SEQ ID NO: 1

3' ACGUUCCCCAAGGACUGGUU 5'-effector sequence of
ddRNAi agent (SEQ ID NO: 19) to target SEQ ID NO:
1, which when read in the 5' to 3' direction, can
be seen to be substantially complementary to the
predicted mRNA transcript of the target sequence.
```

The ddRNAi agents of the invention are preferably expressed within and as part of a miRNA structure. A diagrammatic representation of a miRNA structure is shown in FIG. 1G.

As explained in the background section, both strands of the ddRNAi agent have the potential to be the effector sequence. However there is evidence that particular features of a sequence can favour one strand to enter the RISC and the other strand to be destroyed. There is evidence that the protein Argonaut 2 (AGO2) of the RISC complex has a preference for sequences with a 5' A, and to a lesser extent a 5' U.

There is evidence that a step in RISC loading "senses" thermodynamic stability of an RNA duplex across a potential target site in dsRNA precursors and preferentially loads the strand whose 5' end is from the less stable end of the duplex. Therefore target site sequences were typically adjusted to maximise the number of AT base pairs at the 3' end of the target site, ie maximising the number of A or U bases in the 5' end of the effector strand.

For example, in one embodiment of this aspect of the invention, there is provided a DNA-directed RNA interference (ddRNAi) agent for inhibiting expression of one or more target sequences in a pain-associated gene, the ddRNAi agent comprising at least:
 a first effector sequence of any 10 or more contiguous nucleotides within 5' ACCAUGAGGAAGCUGAA-GUC 3' (SEQ ID NO:21); and
 a first effector complement sequence, wherein the first effector complement sequence is substantially complementary to the first effector sequence.

The first effector sequence is substantially complementary to a predicted transcript of a region of the target gene.

Preferably the first effector sequence is at least 17 or more contiguous nucleotides within 5' ACCAUGAG-GAAGCUGAAGUC 3' (SEQ ID NO:21).

When the first effector sequence has 1, 2, 3, 4 or 5 nucleotides different to SEQ ID NO:21, the differences are preferably present in the first and/or last 5 nucleotides, and at least the centre 10 nucleotides are 100% complementary to a predicted transcript of a region of the target gene.

In alternative embodiments, the ddRNAi agent comprises a first effector sequence of any 10 or more, preferably any 17 or more, contiguous nucleotides within SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO: 36.

Preferably, the ddRNAi agent comprises a first effector sequence of any 10 or more, preferably any 17 or more, contiguous nucleotides within SEQ ID NO:21, SEQ ID NO:22 or SEQ ID NO:23.

In particularly preferred embodiments, the ddRNAi agent comprises a first effector sequence of any 10 or more, preferably any 17 or more, contiguous nucleotides within sequences able to inhibit the expression of a target gene region by at least 70%. Preferably, in this embodiment, the first effector is selected from SEQ ID NO:21, which targets a sequence of SEQ ID NO:3.

The first effector sequence may comprise a sequence selected from any 10 or more and preferably any 17 or more contiguous nucleotides within a sequence from the group consisting of SEQ ID NOS: 19-36, or alternatively, each effector sequence may be a variant of SEQ ID NOS:19-36, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 19-36.

Multiple Targeting ddRNAi Agents ddRNAi agents with multiple effector sequences have the advantage of being able to target a range of sequences and naturally occurring variants thereof that may exist between individuals, as well as the advantage of the additive or synergistic effects achieved with multiple effector sequences as opposed to single effector sequences.

In one embodiment of the invention, the ddRNAi agent comprises two or more effector sequences to enable targeting of more than one target sequence of the pain-associated gene. The multiple target sequences may be in the same region of the gene. For example, a 17 to 30 nucleotide region that has natural variation in the sequence between individuals. Alternatively, the target sequences may be in different regions of the one target gene. The target sequences may also be in different pain-associated genes. For example, a first effector sequence targets a sequence in PKCγ, whereas a second effector sequence in the same ddRNAi agent targets a sequence in a DAO gene.

To provide greater specificity the ddRNAi agent comprises the following (in no particular order):
 a first effector sequence of at least 17 nucleotides in length;
 a second effector sequence of at least 17 nucleotides in length;
 a first effector complement sequence, wherein the first effector complement sequence is substantially complementary to the first effector sequence; and
 a second effector complement sequence, wherein the second effector complement sequence is substantially complementary to the second effector sequence.

The first and second effector sequences of a multiple targeting ddRNAi agent form a double stranded region with their respective effector complements. Preferably, the first and second effector sequences are 17 to 30 nucleotides in length and more preferably 17 to 21. More preferably, the first and second effector sequence are both selected from any 10 or more and preferably any 17 or more contiguous nucleotides within any one of the sequences of SEQ ID NOS: 19-36 listed in Table 2 above, or are sequences having 1, 2, 3, 4 or 5 nucleotides difference from those sequences listed in Table 2.

In one embodiment, the first effector sequence is selected from any 10 or more and preferably any 17 or more contiguous nucleotides within a sequence from any one of the group consisting of SEQ ID NOS:19-36, and the second effector sequence is selected from any 10 or more and preferably any 17 or more contiguous nucleotides within a sequence from any one of the group consisting of SEQ ID NOS: 19-36. The first and second effector sequence may both be the same sequence or may alternatively be different sequences.

The first and second effector sequence may each comprise a sequence selected from any 10 or more contiguous nucleotides within a sequence from the group consisting of SEQ ID NOS: 19-36, or alternatively, each effector sequence may also be a variant of SEQ ID NOS: 19-36, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 19-36. When there are two or more effector sequences, they may represent a combination of the 3 types described above.

In particularly preferred embodiments, the first and second effector sequence comprise any 10 or more, preferably any 17 or more, contiguous nucleotides within sequences able to inhibit the expression of a target gene region by at least 70%. Preferably in this embodiment, each effector sequence is selected from any 10 or more and preferably any 17 or more contiguous nucleotides within a sequence from any one of the group consisting of SEQ ID NO:21 and SEQ ID NO:22.

Long Hairpin Version

When the ddRNAi agent contains more than one effector sequence, and the ddRNAi agent is expressed as a single strand of RNA, it will fold to form different structures depending on the order of the effector sequences and the sequences complementary to the effector sequences. In one embodiment, there is provided a DNA-directed RNA interference (ddRNAi) agent for inhibiting expression of one or more target sequences in a pain-associated gene, preferably a PKCγ gene and/or a DAO gene, the ddRNAi agent comprising, in a 5' to 3' direction, at least:
 a first effector sequence of at least 17 nucleotides in length;
 a second effector sequence of at least 17 nucleotides in length;
 a second effector complement sequence, wherein the second effector complement sequence is substantially complementary to the second effector sequence; and
 a first effector complement sequence, wherein the first effector complement sequence is substantially complementary to the first effector sequence
and wherein each effector sequence is substantially complementary to a predicted transcript of a region of the target gene. This will result in a ddRNAi agent with a structure as shown in FIG. 1A. See also WO2004/106517, incorporated herein by reference.

Alternatively, at least one effector, and preferably both effector sequences, are 100% complementary to a predicted transcript of a region of the target gene. Preferably the first and second effector sequences are both selected from the group consisting of any 10 or more and preferably any 17 or more contiguous nucleotides within any one of SEQ ID NOS: 19-36. For example, in one embodiment, there is provided a DNA-directed RNA interference (ddRNAi) agent for inhibiting expression of one or more target sequences in a pain-associated gene, the ddRNAi agent comprising, in a 5' to 3' direction, at least:

a first effector sequence of 5' ACCAUGAG-GAAGCUGAAGUC 3' (SEQ ID NO:21);
 a second effector sequence 5' UCAAACUUCUGGAG-GAGGCU 3' (SEQ ID NO:22);
 a second effector complement wherein the second effector complement sequence is substantially complementary to the second effector sequence; and
 a first effector complement wherein the first effector complement sequence is substantially complementary to the first effector sequence
and wherein the pain-associated gene is PKCγ.

Each effector sequence is substantially complementary to a predicted transcript of a region of the target gene.

Alternatively, at least one effector, and preferably both effector sequences, are 100% complementary to a predicted transcript of a region of the target gene.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS: 21-26, more preferably from SEQ ID NOS: 21-23 and most preferably SEQ ID NOS: 21 and 22.

In yet another embodiment, being an embodiment where the ddRNAi agent has 3 effector sequences, there is provided a DNA-directed RNA interference (ddRNAi) agent for inhibiting expression of one or more target sequences in the target gene, the ddRNAi agent comprising, in a 5' to 3' direction, at least:
 a first effector sequence of 5' ACCAUGAG-GAAGCUGAAGUC 3' (SEQ ID NO:21);
 a second effector sequence of 5' UCAAACUUCUGGAG-GAGGCU 3' (SEQ ID NO:22);

```
                                          (SEQ ID NO: 23)
a third effector sequence of 5' GCAGUUGUCAGCAUCG

GCCA 3';
``` a third effector complement sequence wherein the third effector complement sequence is substantially complementary to the third effector sequence;
 a second effector complement sequence wherein the second effector complement sequence is substantially complementary to the second effector sequence; and
 a first effector complement sequence wherein the first effector complement sequence is substantially complementary to the first effector sequence.

Each effector sequence is substantially complementary to a predicted transcript of a region of the target gene.

Alternatively, at least one effector, and optionally 2 out of the 3 or all 3 of the effectors, are 100% complementary to a predicted transcript of a region of the target gene.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS:19-36, more preferably from SEQ ID NOS: 19-26, and most preferably from SEQ ID NOS: 21-23.

It will also be appreciated by the skilled person that the order of effector and effector complements can be altered, provided that a single, long hairpin structure is formed by annealing of the effector sequence with its effector complement to form dsRNA. For example, in a 2-effector sequence ddRNAi agent, the sequences may be arranged in the following exemplary 5' to 3' orders:
first effector-second effector-second effector complement-first effector complement;
second effector-first effector-first effector complement-second effector complement;
first effector-second effector complement-second effector-first effector complement;
first effector complement-second effector complement-second effector-first effector;
first effector complement-second effector-second effector complement-first effector.

In a 3-effector sequence ddRNAi agent, the sequences may be arranged in the following exemplary 5' to 3' orders:
first effector-second effector-third effector-third effector complement-second effector complement-first effector complement
first effector-second effector complement-third effector-third effector complement-second effector-first effector complement;
first effector-second effector-third effector complement-third effector-second effector complement-first effector complement
first effector-third effector-second effector complement-second effector-third effector complement-first effector complement
first effector complement-second effector complement-third effector complement-third effector-second effector-first effector complement
first effector complement-second effector complement-third effector-third effector complement-second effector-first effector.

In yet further embodiments, the first effector sequence may be selected from any 10 or more and preferably any 17 or more contiguous nucleotides within a sequence from the group consisting of SEQ ID NOS:19-36; the second effector sequence may be selected from any 10 or more and preferably any 17 or more contiguous nucleotides within a sequence from the group consisting of SEQ ID NOS:19-36; the third effector sequence may be selected from any 10 or more and preferably any 17 or more contiguous nucleotides within a sequence from the group consisting of SEQ ID NOS:19-36; and any further effector sequences may be selected from any 10 or more and preferably any 17 or more contiguous nucleotides within a sequence from the group consisting of SEQ ID NOS:19-36. Alternatively, each effector sequence may also be a variant of SEQ ID NOS:19-36, having 1, 2, 3, 4 or 5 nucleotide variations. Preferably, the differences are present in the first and/or last 5 nucleotides, and at least the centre 11-12 nucleotides are 100% complementary to a predicted transcript of a region of the target gene. In each of the embodiments, wherein only PKCγ is to be targeted, each effector sequence is selected from SEQ ID NOS: 19-26; wherein only DAO is to be targeted, each effector sequence is selected from SEQ ID NOS: 27-36.

The first, second and third effector sequence may each comprise a sequence selected from any 10 or more contiguous nucleotides within a sequence from the group consisting of SEQ ID NOS: 19-36, or alternatively, each effector sequence may also be a variant of SEQ ID NOS:19-36, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 19-36. When there are multiple effector sequences, they may represent a combination of the 3 types described above.

Multiple Hairpin Version

In an alternative embodiment, there is provided a DNA-directed RNA interference (ddRNAi) agent for inhibiting expression of one or more target sequences in a pain-associated gene, preferably a PKCγ gene and/or a DAO, the ddRNAi agent comprising, in a 5' to 3' direction, at least:
a first effector sequence of at least 17 nucleotides in length;
a first effector complement wherein the first effector complement sequence is substantially complementary to the first effector sequence;
a second effector sequence of at least 17 nucleotides in length; and
a second effector complement wherein the second effector complement sequence is substantially complementary to the second effector sequence and wherein each effector sequence is substantially complementary to a predicted transcript of a region of the target gene.

Alternatively, at least one effector, and preferably both effector sequences, is 100% complementary to a predicted transcript of a region of the target gene.

Figure 1B:
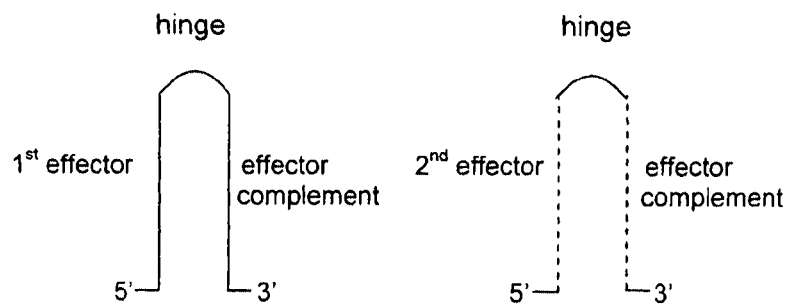
Figure 1C:
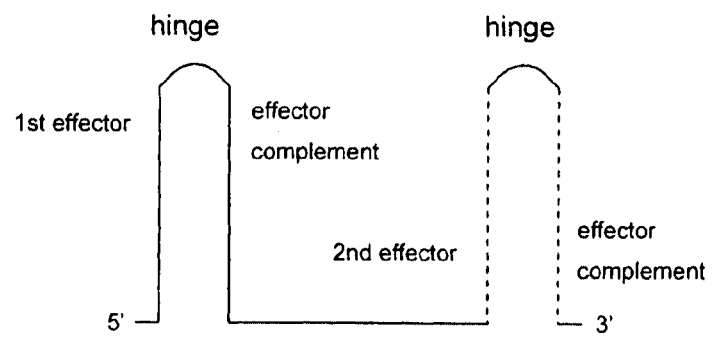
Figure 1D:
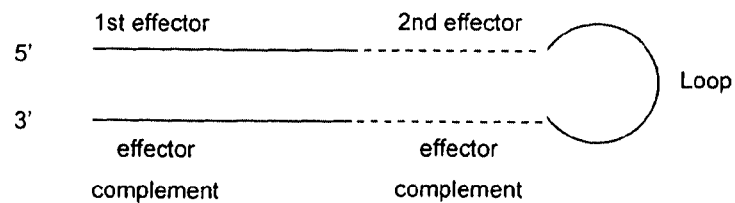

This will result in a ddRNAi agent with a structure as shown in FIG. 1B or C, depending on the type of expression cassette used to express it (see later in the specification). See also WO2005/087926 and WO2006/084209, incorporated herein by reference.

In either embodiment, where there are 2 target sequences, it is preferable that the first and second effector sequences are both substantially identical to a predicted transcript of the target gene containing their respective target sequences.

Preferably the first and second effector sequences are both selected from any 10 or more and preferably any 17 or more contiguous nucleotides within a sequence from the group consisting of SEQ ID NOS: 19-36. For example, in one embodiment, there is provided a DNA-directed RNA interference (ddRNAi) agent for inhibiting expression of one or more target sequences in a pain-associated gene, the ddRNAi agent comprising, in a 5' to 3' direction, at least:
a first effector sequence of any 10 or more contiguous nucleotides within 5' ACCAUGAGGAAGCUGAAGUC 3' (SEQ ID NO:21);
a first effector complement sequence wherein the first effector complement sequence is substantially complementary to the first effector sequence;
a second effector sequence any 10 or more contiguous nucleotides within 5' UCAAACUUCUGGAGGAGGCU 3' (SEQ ID NO:22) or 5' GCAGUUGUCAGCAUCGGCCA 3' (SEQ ID NO:23); and
a second effector complement sequence wherein the second effector complement sequence is substantially complementary to the second effector sequence, and wherein the pain associated gene is PKCγ.

Each effector sequence is substantially complementary to a predicted transcript of a region of the target gene.

Alternatively, at least one effector, and preferably both effector sequences, is 100% complementary to a predicted transcript of a region of the target gene.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS: 19-36, more preferably SEQ ID NOS: 19-26, and most preferably SEQ ID NOS: 21-23.

In yet another embodiment, being an embodiment where the ddRNAi agent has 3 effector sequences, there is provided a DNA-directed RNA interference (ddRNAi) agent for inhibiting expression of one or more target sequences in a pain-associated gene, the ddRNAi agent comprising, in a 5' to 3' direction, at least:
- a first effector sequence of any 10 or more contiguous nucleotides within 5' ACCAUGAGGAAGCUGAA-GUC 3' (SEQ ID NO:21);
- a first effector complement sequence wherein the first effector complement sequence is substantially complementary to the first effector sequence;
- a second effector sequence of any 10 or more contiguous nucleotides within 5' UCAAACUUCUGGAGGAG-GCU 3' (SEQ ID NO:22);
- a second effector complement sequence wherein the second effector complement sequence is substantially complementary to the second effector sequence;
- a third effector sequence of any 10 or more contiguous nucleotides within 5' GCAGUUGUCAGCAUCG-GCCA 3' (SEQ ID NO:23); and
- a third effector complement sequence wherein the third effector complement sequence is substantially complementary to the third effector sequence, and wherein the pain-associated gene is PKCγ.

Each effector sequence is substantially complementary to a predicted transcript of a region of the target gene.

Alternatively, at least one effector, and optionally 2 out of the 3 or all 3 of the effectors, is 100% complementary to a predicted transcript of a region of the target gene.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS: 19-36, more preferably SEQ ID NOS: 19-26, and most preferably SEQ ID NOS: 21-23.

In yet further embodiments, the first effector sequence may be any 10 or more contiguous nucleotides within a sequence selected from the group consisting of SEQ ID NOS:19-36; the second effector sequence may be any 10 or more contiguous nucleotides within a sequence selected from the group consisting of SEQ ID NOS:19-36; the third effector sequence may be any 10 or more contiguous nucleotides within a sequence selected from the group consisting SEQ ID NOS:19-36; and any further effector sequences may be any 10 or more contiguous nucleotides within a sequence selected from the group consisting of SEQ ID NOS:19-36. Preferably, each effector sequence is at least 17 contiguous nucleotides.

Each effector sequence may also be a variant of SEQ ID NOS:19-36, having 1, 2, 3, 4 or 5 nucleotide variations. Preferably, the differences are present in the first and/or last 5 nucleotides, and at least the centre 10-12 nucleotides are 100% complementary to a predicted transcript of a region of the target gene.

The first, second and third effector sequence may each comprise a sequence selected from any 10 or more contiguous nucleotides within a sequence from the group consisting of SEQ ID NOS: 19-36, or alternatively, each effector sequence may also be a variant of SEQ ID NOS:19-36, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 19-36. When there are multiple effector sequences, they may represent a combination of the 3 types described above.

Furthermore, in the long hairpin structure or the multiple hairpin structure the ddRNAi agent may include additional effector sequences and corresponding complementary sequences according to one of the following formula:

Long hairpin;

[effector sequence]$_{1-10}$[effector complement sequence]$_{1-10}$

Multiple Hairpin:

[effector sequence–effector complement sequence]$_{1-10}$

Preferably, in the long hairpin formula, the number of effector sequences is equal to the number of effector complement sequences. Typically, there are 2, 3, 4 or 5 effector sequences, and accordingly, 2, 3, 4 or 5 effector complement sequences respectively.

When the ddRNAi agent does contain more than one effector sequence, the effector sequences may be the same or different. For example, if a ddRNAi agent has 3 effector sequences, 2 effector sequences may have the same sequence, while 1 is different. Alternatively, all 3 effector sequences may be different. Preferably, the effector sequences are any 10 or more and preferably any 17 or more contiguous nucleotides within a sequence selected from the group consisting of SEQ ID NOS:19-36, or variants thereof which have 1, 2, 3, 4 or 5 nucleotide variations. Preferably, the differences are present in the first and/or last 5 nucleotides, and at least the centre 10-12 nucleotides are 100% complementary to a predicted transcript of a region of the target gene.

When targeting a single region of a target sequence that has naturally occurring variants, or single nucleotide polymorphisms, it is preferably that at least one effector sequence is chosen from any 10 or more and preferably any 17 or more contiguous nucleotides within a sequence selected from the group consisting of SEQ ID NOS:19-36, whereas other effector sequences are variants of that chosen sequence. For example, a first effector sequence may comprise 20 nucleotides of SEQ ID NO: 21; the second effector sequence should therefore be a variant of SEQ ID NO:21.

Hairpin Structures

In the above embodiments, the effector sequence hybridises with its corresponding effector complement sequence to form a hairpin structure. At the end of the hairpin, two or more unbound nucleotides form the 'hinge' or 'loop'. In one embodiment, the unbound nucleotides are part of the effector sequence and the effector complement, such that only a portion of the at least 17 nucleotides of the effector sequence will form a duplex with its corresponding complementary sequence. For example, when the effector sequence and its complement are both 20 nucleotides long, 18 of the nucleotides may base pair to form a double stranded region, leaving a total of 4 nucleotides to form a single stranded loop between and joining the effector sequence and its effector complement sequence.

In an alternative embodiment, an additional sequence that is non-complementary to itself, the target sequence, the effector sequence or the effector complement may be included in the ddRNAi. As such, in yet another embodiment of the invention, the ddRNAi agent further includes a sequence of 2 to 100 unpaired nucleotides capable of forming a loop, more preferably, 2 to 10 unpaired nucleotides. In a preferred embodiment the loop includes the nucleotide sequence AA, UU, UUA, UUAG, UUACAA, CAAGAGA or $N_1AAN_2$, where $N_1$ and $N_2$ are any of C, G, U and A and may be the same or different. Otherwise, specific loop sequences include ACUGUGAAGCA-GAUGGGU, which may be partially or completely derived from the miRNA when the ddRNAi agent is expressed as part of a miRNA structure. In these loops, not all of the loop sequence has to remain non-annealed. In a loop of, for example, 18 nucleotides, the first and last 3 nucleotides for example may anneal with each other, leaving the intervening 15 nucleotides non-annealed.

There may be one or more loops depending on the ddRNAi agent structure. When a ddRNAi agent has a structure based on formula [effector sequence]$_{1-10}$ [effector complement sequence]$_{1-10}$ additional non-self-complementary sequence to give rise to a single loop structure is contained between the last effector sequence and the effector complement sequence of that last effector sequence, as illustrated in FIG. 10. In this embodiment, there is therefore provided a DNA-directed RNA interference (ddRNAi) agent for inhibiting expression of one or more target sequences in a pain-associated gene, preferably a PKCγ gene and/or DAO gene, the ddRNAi agent comprising, in a 5' to 3' direction, at least:
- a first effector sequence of at least 17 nucleotides in length;
- a second effector sequence of at least 17 nucleotides in length;
- a sequence of 2 to 100 non-self-complementary nucleotides;
- a second effector complement sequence wherein the second effector complement sequence is substantially complementary to the second effector sequence; and
- a first effector complement sequence wherein the first effector complement sequence is substantially complementary to the first effector sequence and wherein each effector sequence is substantially complementary to a predicted transcript of a region of the target gene.

Figure 1E:
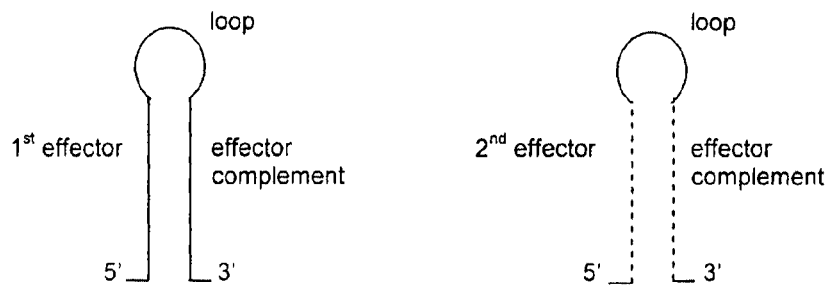
Figure 1F:
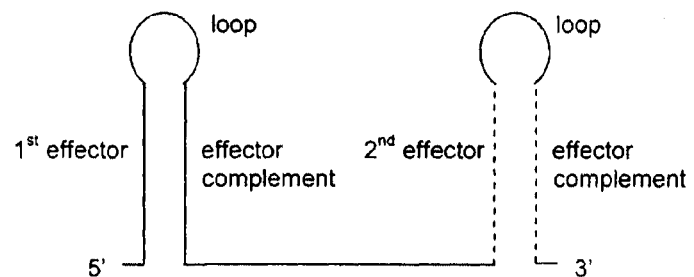
Figure 1G:
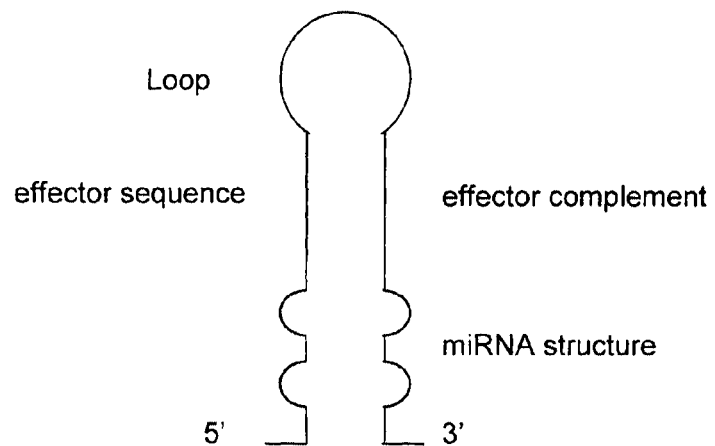

When the ddRNAi agent has a multiple hairpin structure based on formula [effector sequence-effector complement sequence]$_{1-10}$ additional non-self-complementary sequence is contained between each effector sequence and its complementary sequence to give rise to a loop structure, as illustrated in FIGS. 1E and F (depending on the type of expression cassette used to express it—see later in the specification). In this embodiment, there is provided a DNA-directed RNA interference (ddRNAi) agent for inhibiting expression of one or more target sequences in a pain-associated gene, preferably a PKCγ gene, the ddRNAi agent comprising, in a 5' to 3' direction, at least:
- a first effector sequence of at least 17 nucleotides in length;
- a sequence of 2 to 100 non-self-complementary nucleotides;
- a first effector complement sequence wherein the first effector complement sequence is substantially complementary to the first effector sequence;
- a second effector sequence of at least 17 nucleotides in length;
- a sequence of 2 to 100 non-self-complementary nucleotides; and
- a second effector complement sequence wherein the second effector complement sequence is substantially complementary to the second effector sequence and wherein each effector sequence is substantially complementary to a predicted transcript of a region of the target gene.

In this embodiment where there are more than two effector and complementary sequences, and therefore more than two hairpin structures, the length of additional non-self-complementary sequence that forms each loop structure does not have to be the same. For example, one loop structure may have 5 nucleotides, while another loop structure may have 9 nucleotides.

2 Strand ddRNAi Agents

As will be appreciated by one skilled in the art, it is not necessary that the entire ddRNAi agent is expressed as one sequence. For example, in one embodiment of the invention, the first effector sequence may be generated (e.g., transcribed by one DNA sequence), and the first effector complement sequence may be generated (e.g., transcribed from a separate DNA sequence). Optionally, a loop sequence may be attached to either transcript or part of the loop attached to the 3' end of one transcript and the 5' end of the other transcript, and that loop sequence may be derived from or partially derived from a miRNA when the effector or effector complement sequence is expressed as part of a structure. Within the cell, the two transcripts then form the ddRNAi agent by hybridising through annealing between the first effector sequences and its complement.

In Vitro Expressed ddRNAi Agents of Chemically Synthesised siRNA

While it is envisaged that effective treatment of chronic pain will require ddRNAi agents to be expressed in vivo from ddRNAi constructs (as will be outlined below), there may be circumstances where it is desirable to administer ddRNAi agents that are expressed in vitro or to administer siRNAs that are chemically synthesised, thereby functioning as more of a transient therapy. Acute pain for example may benefit from a short term treatment with siRNAs that do not integrate and replicate in the cells.

The ddRNAi agents of the invention may therefore be expressed in vitro and then delivered to target cells. Alternatively, siRNAs may be chemically synthesised and then delivered to the target cells. In light of this, in another aspect of the invention, there is provided a small interfering RNAi agent (siRNA agent) for inhibiting expression of one or more target sequences in a pain-associated gene, the siRNA comprising
- a first effector sequence of at least 17 nucleotides in length; and
- a first effector complement sequence wherein the first effector complement sequence is substantially complementary to the first effector sequence;

and wherein the effector sequence is substantially complementary to a predicted transcript of a region of the target gene.

Similarly to the ddRNAi agents described above, the siRNA agent may also include more than one effector sequence for multiple targeting, be that multiple targets in a single gene such as PKCγ or DAO, or multiple targets in more than one gene, such as PKCγ and DAO. The effector sequences preferably target the PKCγ gene and/or DAO, and most preferably, are selected from any 10 or more and preferably any 17 or more contiguous nucleotides within a sequence from the group consisting of SEQ ID NOS: 19-36.

Considerable flexibility is possible in the design of siRNAs. Typically siRNAs consist of dsRNA molecules with 5'-phosphate and 3'-hydroxyl residues, strand lengths can vary from 20-29 nucleotides and may optionally be designed to include 2 nucleotide 3' overhangs. In some embodiments each strand can be synthesised as N19-27TT (where TT can be deoxyribonucleotides). siRNAs can be readily designed based on regions of SEQ ID NOS: 19-36 as described above and can be used therapeutically as single sequences or in any combinations. Alternatively siRNA agents can consist of single RNA molecules containing effector and effector complement sequences similar or identical to those expressed from ddRNAi expression cassettes. These sequences can be based on SEQ ID NOS: 19-36 and can be used therapeutically as single sequences or in any combination. The siRNAs can be chemically synthesized with appropriately protected ribonucleoside phosphoramidites and a conventional synthesizer and thus are widely available commercially and able to be designed and synthesised according to routine methods in the art. In preferred embodiments, the siRNAs have the sequences of any 10 or more contiguous nucleotides within a sequence from one or more of SEQ ID NOS:19-36.

A number of transfection reagents have been used for delivering siRNA into different cell lines. Lipofectamine 2000 and Oligofectamine are routinely used for siRNA delivery. Naked siRNAs have also been delivered by hydrodynamic transfection methods. Other delivery methods would be known by the skilled person.

Expression Cassettes and miRNA Backbones

The ddRNAi agents of the invention are expressed from DNA expression cassettes (ddRNAi expression cassette). The expression cassettes comprise the regulatory sequences required for expression, such as the promoter, together with the DNA sequence that encodes the ddRNAi agent itself. In embodiments in which the ddRNAi agent is expressed as part of a miRNA structure, the expression cassette also includes the DNA sequence that encodes for that miRNA structure.

As will be explained further on, ddRNAi expressed cassettes are themselves part of a DNA vector, referred to herein as 'ddRNAi constructs'.

ddRNAi expression cassettes comprise (in no particular order):
  one of more promoter sequences
  one or more DNA sequences that encode for one or more effector sequences
  one or more DNA sequences that encode for one or more effector complement sequences;
and optionally
  one or more DNA sequences that encode for loop sequences
  one or more terminator sequences; and
  one or more enhancer sequences.

The first promoter sequence and last terminator sequence may be derived from the vector in to which the expression cassette is cloned.

In one embodiment, there is provided a DNA-directed RNA interference (ddRNAi) expression cassette for expressing a ddRNAi agent, wherein the ddRNAi agent inhibits expression of one or more target sequences in a pain-associated gene, the ddRNAi expression cassette comprising, in a 5' to 3' direction:
  a promoter sequence
  a DNA sequence that encodes for a first effector sequence
  a DNA sequence that encodes for a first effector complement sequence; and
  optionally a terminator sequence.

The DNA sequence that encodes for the first effector sequence is preferably a DNA that encodes for 10 or more, preferably 17 or more, contiguous nucleotides within a sequence from any one of SEQ ID NOS: 19-36. In a particularly preferred embodiment, the first effector sequence comprise any 10 or more, preferably any 17 or more, contiguous nucleotides within sequences able to inhibit the expression of a target gene region by at least 70%.

Preferably, in this embodiment, the first effector sequence is selected from SEQ ID NOS: 19-36, more preferably SEQ ID NOS: 19-26, and most preferably SEQ ID NOS: 21-23.

Alternatively, as outlined above in relation to the ddRNAi agent itself, the sequence that encodes for the effector sequence may encode an effector sequence that varies by 1, 2, 3, 4 or 5 nucleotides from SEQ ID NOS: 19-36 without effecting the ability of the sequence encoded to base pair with the target sequence and inhibit expression of the target sequence.

The skilled person would appreciate that a DNA sequence encoding any given RNA sequence is the same sequence as the RNA but having thymine (T) bases instead of uracil (U) bases. The ddRNAi expression cassettes encoding ddRNAi agents having more than one effector sequence in a long hairpin structure comprise, in a 5' to 3' direction:
  a promoter sequence;
  a DNA sequence that encodes for a first effector sequence;
  a DNA sequence that encodes for a second effector sequence;
  optionally a sequence that encodes for sequence capable of forming a loop;
  a DNA sequence that encodes for a second effector complement sequence;
  a DNA sequence that encodes for a first effector complement sequence; and
  optionally a terminator sequence.

Preferably the DNA sequences encode first and second effector sequence selected from any 10 or more and preferably any 17 or more contiguous nucleotides within a sequence from the group consisting of SEQ ID. NOS: 19-36. Preferably, the first and second effector sequence is selected from SEQ ID NOS: 21-23. Alternatively, the DNA sequences encode for an effector sequence that varies from SEQ ID NOS: 19-36 by 1, 2, 3, 4 or 5 nucleotides without affecting the ability of the effector sequence encoded to base pair with the target sequence and inhibit expression of the target sequence.

When the ddRNAi agent has more than one effector sequence and a multiple hairpin structure based on formula [effector sequence-effector complement sequence]$_{1-10}$ expression of each [effector sequence-effector complement sequence] pair may be controlled by a single promoter, or alternatively by a separate promoter. When separate promoters are contemplated, the ddRNAi expression cassette comprises, in a 5' to 3' direction:
  a promoter sequence
  a DNA sequence that encodes for a first effector sequence
  a DNA sequence that encodes for a first effector complement sequence;
  optionally a terminator sequence;
  a promoter sequence;
  a DNA sequence that encodes for a second effector sequence;
  a DNA sequence that encodes for a second effector complement sequence; and
  optionally a terminator sequence.

In this embodiment, multiple ddRNAi agents are produced from the one expression cassette, as each effector/effector complement is expressed as a single hairpin structure.

When a single promoter is contemplated, the ddRNAi expression cassette comprises, in a 5' to 3' direction:
  a promoter sequence
  a DNA sequence that encodes for a first effector sequence a DNA sequence that encodes for an effector complement sequence to the first effector sequence;

a DNA sequence that encodes for a second effector sequence;

a DNA sequence that encodes for an effector complement sequence to the second effector sequence; and optionally a terminator sequence.

Similarly to the above embodiments, the DNA sequences preferably encode first and second effector sequence selected from any 10 or more and preferably any 17 or more contiguous nucleotides within a sequence from the group consisting of SEQ ID NOS:19-36, or, effector sequences that vary in sequence from SEQ ID NOS: 19-36 by 1, 2, 3, 4 or 5 nucleotides. Preferably, the first and second effector sequence is selected from SEQ ID NOS: 19-36, more preferably SEQ ID NOS: 19-26, and most preferably SEQ ID NOS: 21-23.

Any of the abovementioned ddRNAi agents can be expressed in a miRNA structure from an expression cassette.

Processing of shRNAs expressed from ddRNAi expression, cassettes and constructs can be imprecise. The expression of the ddRNAi within and as part of an RNA structure like a miRNA, which is a natural substrate for RNAi processing pathways, is one way to minimise this. McBride of al. (2008) designed "artificial miRNA" constructs which expressed sequences from the base and loop of endogenous miRNAs; these showed reduced toxicity suggesting more precise processing of expressed shRNAs. Wu et al. (2011) showed that mismatched duplexes (containing mismatches in the passenger strand) sometimes showed increased silencing activity, due possibly to their greater structural resemblance to endogenous miRNAs. Similarly Gu of al. (2012) showed the introduction of bulges adjacent to loop sequences in shRNA molecules can result in increased precision of dicer processing.

In embodiments where the effector and effector complement are expressed as a miRNA structure, the ddRNAi expression cassette further includes sequence that encodes for the miRNA structure referred to herein as "miRNA encoding sequence" or "ME sequence". This is the DNA sequence contained within a ddRNAi expression cassette that encodes for RNA which, once expressed as miRNA sequence, folds in to a miRNA structure. The effector sequence and the effector complement therefore are expressed as part of or within that miRNA structure. As will be appreciated from the Figures illustrating a ddRNAi agent expressed in a miRNA structure, and as detailed earlier in the specification, the ME sequences will be located upstream and downstream of the effector sequence and the effector complement sequence as required. Using an expression cassette that expresses a ddRNAi agent with a single effector-effector complement pair as an example, there is provided a DNA-directed RNA interference (ddRNAi) expression cassette for expressing a ddRNAi agent within and as part of a miRNA structure, wherein the ddRNAi agent inhibits expression of one or more target sequences in an pain-associated gene, the ddRNAi cassette comprising, in a 5' to 3' direction:

a promoter sequence a first ME sequence a DNA sequence that encodes for a first effector sequence optionally a sequence that encodes for sequence capable of forming a loop a DNA sequence that encodes for a first effector complement sequence;

a second ME sequence; and optionally a terminator sequence.

In other words, the RNA sequence expressed from this ddRNAi expression cassette is capable of forming a structure similar to an endogenous miRNA.

The optional sequence that encodes for sequence capable of forming a loop may also be ME sequence or partial ME sequence. For example, if a particular miRNA structure is being utilised as the structure in which the ddRNAi agent is expressed within and as part of, all or part of the loop sequence of the ddRNAi agent may come from the same miRNA. In alternative embodiments, the all or part of the loop sequence may come from a different miRNA than the miRNA structure encoded by the ME sequences, but nonetheless, is still miRNA derived or originating sequence.

The ddRNAi expression cassette may alternatively be described by reference to the total length of the ddRNAi agent expressed, which is a product of the total length of sequence between the promoter and terminator. For example, when the length of the effector sequence in a single effector ddRNAi consists of 17, 18, 19, 20, 21, 22, 23, 24, 25, 26, 27, 28, 29, or 30 nucleotides, the ddRNAi expression cassette will have a length of 34 to 60 nucleotides between the promoter and terminator. This length may further include 2 to 100 nucleotides of "loop" or "hinge" sequence, giving a length of between 36 to 160 nucleotides. For ddRNAi agents having multiple effector sequences, where each effector sequence consists of 17, 18, 19, 20, 21, 22, 23, 24, 25, 26, 27, 28, 29, or nucleotides, the overall length is increased proportionally.

The presence of ME sequence for encoding the miRNA structure/s will also add to overall length.

One useful way of designing ddRNAi expression cassettes of the invention is to assume Dicer cuts every 22 nucleotides (also referred to as 22 nt phasing), and processes from the base of the shRNA. The DNA sequences that encode effector sequences can therefore be designed to encode any 10 or more, and preferably any 17 or more contiguous nucleotides within a sequence from the group consisting of SEQ ID NOS:19-36, together with appropriate spacers and other sequence requirements for the appropriate promoter.

Agents targeting different sites of mRNA are suitable for shRNA construction, because they can avoid the influence of secondary structures of mRNA, and thus perform their functions independently.

When a U6 promoter is used, it is preferable that the DNA sequence operably linked to the promoter starts with a guanine (G) base; when a H1 promoter is used, it is preferable that the DNA sequence operably linked to the promoter starts with an adenine (A) base. The effector encoding sequence can therefore be modified accordingly.

The use of miRNA-derived sequences to drive expression of shRNAs is particularly advantageous when using pol II promoters. Transcriptional initiation sites for pol II promoters are frequently imprecise. Since dicer processing of an shRNA is largely dependent on the structure of the shRNA, processing will not be greatly effected by slight variations in transcriptional start sites in most instances. The use of miRNA derived sequences therefore permits greater flexibility in designing ddRNAi constructs that utilise pol II promoters.

In some instances it may be advantageous to increase the length of shRNAs. One way to accomplish this is to extend the length of the effector sequence in an shRNA to maximise its complementarity to the target sequence, in either a 5' or 3' direction, and also extend the length of the effector complement to maximise base pairing within the stem of the shRNA. For example an shRNA based on SEQ ID NO: 21 could be readily extended in a 5' or 3' direction to target additional sequences adjacent to those in SEQ ID NO:3 to produce an shRNA with a 30 nucleotide stem. The effector sequence could share substantial homology to the target as defined elsewhere in this specification.

In some instances it may be desirable to avoid the DNA sequence TTTT within effector, effector complement or loop sequences since these can act as transcriptional terminators in expression cassette and constructs which use Pol III promoters such as U6 or H1. shRNA design should also take in to account that U6 termination is expected to add a UU to the 3' end to the shRNA. When designing long hairpin RNAs, it is sometimes advantageous to modify the precise choice of effector sequences (either using sequences from, or adjacent to SEQ ID NOS: 19-36) to maximise the likelihood that Dicer processed effector sequences will include a 5'U or A, thereby encouraging incorporation into AGO2.

The choice of whether to control expression of each [effector sequence-effector complement sequence] pair depends on a number of factors. A single promoter may be utilised to minimise interference between promoters. A ddRNAi expression cassette or construct with only a single promoter is also smaller in size, which can be important in some cases for the stability of the construct, both during production (eg replication in E. coli) and delivery. In addition, the use of a single promoter avoids the possibility of any homologous recombination between promoters.

In circumstances where a degree of regulation of expression of each effector sequence or complement is required though, it is advantageous to design a ddRNAi construct having multiple promoters, whereby expression of each [effector sequence–effector complement sequence] pair is controlled by a separate promoter. In circumstances where the effector sequences are of a different sequence, the nature of the sequence may mean one sequence is expressed to higher expression levels. When it is desired to ensure more equal expression levels of each effector sequence, the more highly expressed effector sequence can be paired with a weaker promoter and vice versa. Moreover, more efficient expression may be achieved as the length of any one sequence to be transcribed is shorter. When multiple promoters are used, it is preferable that not all of the promoters are the same to minimise the risk of any homologous recombination between them. In the case of 2 promoters, each is preferably different. In the case of 3 promoters, at least 2 and optionally all 3 are different from one another.

The DNA sequence encoding the effector sequence is operably linked to the promoter sequence. A sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous.

A "promoter" or "promoter sequence" or "promoter element" is generally a DNA regulatory region capable of binding RNA polymerase in a cell and initiating transcription of a polynucleotide or polypeptide coding sequence such as mRNA or any kind of RNA transcribed by any class of any RNA polymerase. The promoter and terminator may be taken from different genes, but are typically matched to each other; that is, the promoter and terminator elements are taken from the same gene in which they occur naturally. Promoters also may or may not be modified using molecular techniques, or otherwise, e.g., through modification of regulatory elements, to attain weaker levels of transcription.

The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe the ddRNAi agents preferably are constitutive promoters, such as the promoters for ubiquitin, CMV, β-actin, histone H4, EF-1alfa or pgk genes controlled by RNA polymerase II, or promoter elements controlled by RNA polymerase I. In other embodiments, a Pol II promoter such as CMV, SV40, U1, hAAT, β-actin or a hybrid Pol II promoter is employed. In other embodiments, promoter elements controlled by RNA polymerase III are used, such as the U6 promoters (e.g. U6-1, U6-8, U6-9), H1 promoter, 7SL promoter, the human Y promoters (hY1, hY3, hY4 (see Maraia, et al., (1994)) and hY5 (see Maraia, et al., (1994)), the human MRP-7-2 promoter, Adenovirus VA1 promoter, human tRNA promoters, the 5S ribosomal RNA promoters, as well as functional hybrids and combinations of any of these promoters. Variants of these promoters may also be utilised, wherein the promoter is modified to decrease or increase its activity. For example, if a strong promoter causes too much expression of the sequence operably linked to it, it can be modified to decrease its activity.

When a U6 promoter is used, it is preferable that the DNA sequence operably linked to the promoter starts with a guanine (G) base; when a H1 promoter is used, it is preferable that the DNA sequence operably linked to the promoter starts with an adenine (A) base. The sequences of the nucleic acids may therefore favour the use of one promoter over another.

Alternatively in some embodiments it may be optimal to select promoters that allow for inducible expression of the multiple ddRNAi agents expressed from the ddRNAi expression cassette and construct. A number of systems for inducible expression using such promoters are known in the art, including but not limited to the tetracycline responsive system and the lac operator-repressor system (see WO 03/022052 A1 Publication; and U.S. Patent Publication 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., brain). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

In the case of controlling pain neuronal-specific promoters such as Thy1 and H1xb9 (Wang et al, 2011) can be used to drive expression of ddRNAi constructs.

As noted above, enhancer elements are optionally included in the ddRNAi expression cassettes and constructs of the invention. One preferred enhancer element is derived from the promoter of the homeobox Hb9 gene which promotes expression in motor neurones in mouse spinal cord (Peviani et al, 2012).

When the ddRNAi expression cassette or construct contains more than one terminator sequence or element, the terminator sequences or elements may be the same, or different, or there may be a combination of termination elements represented only once and termination elements represented two times or more within any cassette. Whatever terminator sequences or elements are used they should be selected to ensure that they work appropriately with the liver-specific promoter used. In instances where Pol I, Pol II or Pol III promoters are used, appropriate terminator sequences should be employed. Termination elements useful in the present invention include the U1 termination sequence (U1 box), the synthetic polyA terminator, and the so called minimal PolyA terminator. Transcriptional pause sites, such as MAZ1 and MAZ2, (See Ashfield et al EMBO J. 1994 Vol 13 No 23 5656 pp and Yonaha and Proudfoot EMBO J. 2000 Jul. 17; 19(14):3770-7) may be inserted upstream of the polyA terminators to assist in coupling of transcription termination and polyadenylation. For Pol III promoters, the sequences TTTT, TTTTT or TTTTTT are commonly used as terminators. In these instances transcripts are typically terminated by the sequence UU.

ddRNAi Constructs

A challenge in developing any therapeutic is efficient and uniform transduction of all pain-associated neurones in the spinal cord with the ddRNAi agent of the invention is required to provide an effective gene therapy for chronic pain. Moreover, for effective in vivo alleviation of pain, the ddRNAi construct of the invention has to be able to be transfected into primary cells, stem cells, and non-dividing cells. In the absence of cell division, the ddRNAi constructs that express the ddRNAi agents cannot be efficiently introduced into the nucleus, where the DNA is transcribed. To overcome this limitation, the ddRNAi expression cassettes of the invention are introduced into a delivery vector to generate ddRNAi constructs.

ddRNAi expressed cassettes are themselves part of a DNA vector, referred to herein as 'ddRNAi constructs'. When the vector backbone of the construct is compatible with a delivery system, such as a viral delivery system, the ddRNAi expression constructs within the vector backbone are also delivery constructs. A particularly preferred delivery construct is a viral vector. In this regard, there is provided use of a viral vector, like an adeno-associated virus (MV), adenovirus (Ad) or lentivirus (LV) to deliver an expression construct that produces the therapeutic ddRNAi agent from within the cell.

As noted earlier, the vector backbone may serve the dual purpose of being an expression vector as well as a delivery vector. Generation of the construct can be accomplished using any suitable genetic engineering techniques well known in the art, including without limitation, the standard techniques of PCR, oligonucleotide synthesis, DNA synthesis, restriction endonuclease digestion, ligation, transformation, plasmid purification, and DNA sequencing. The construct preferably comprises, for example, sequences necessary to package the ddRNAi construct into viral particles and/or sequences that allow integration of the ddRNAi construct into the target cell genome. The viral construct also may contain genes that allow for replication and propagation of virus, though in preferred embodiments such genes will be supplied in trans. Additionally, the ddRNAi construct may contain genes or genetic sequences from the genome of any known organism incorporated in native form or modified. For example, the preferred viral construct comprises sequences useful for replication of the construct in bacteria.

The viral vector backbone may be selected from lentiviral (LV), adenoviral (Adv), adeno-associated viral (AAV) and herpes simplex virus (HSV) vectors. Non-integrating viral vectors may be used for transient expression in dividing cells of ddRNAi agents of the invention or for longer term stable expression in non-dividing cells. Integrating viral vectors, such as lentiviral vectors, mediate stable, long term expression in both dividing and non-dividing cells. Lentiviral vectors have been shown to be effective in gene therapy in the spinal cord, and therefore make lentivirus an ideal vehicle for this application.

LV vectors offer many advantages for therapeutic delivery of ddRNAi constructs to cells. They are non-replicative vectors that can infect a wide range of cell types including neuronal cells and can infect both dividing and non-dividing cells. LV genomes integrate into host chromosomes where they can specify long-term expression of transgenes, including ddRNAi constructs. A particular advantage of lentiviruses is their low propensity to insert near and activate expression of cellular oncogenes when compared to retroviral vectors, which are carcinogenic. Another advantage of third generation LV vectors is their biological safety, they have been designed in such a way to make reconstitution of infectious viral particles impossible.

LV vectors typically contain sequences necessary for viral encapsulation (psi sequences) and proviral integration (long terminal repeats, typically in a self-inactivating form) and other sequences (eg flap and WPRE sequences) that increase proviral integration frequency and transgene expression. LV vectors can optionally contain selectable marker genes (eg puromycin resistance genes) and reporter genes (eg GFP) for various experimental purposes. LV vectors can be packaged into infectious viral particles in packaging cell lines that express factors required in trans to produce infectious particles, such as RNA polymerase, gag and envelope proteins. Expression of these can be driven by stably integrated transgenes or more commonly using transient expression systems. LV particles can be pseudotyped, by expressing heterologous envelope proteins, such as the envelope G glycoprotein from Vesicular Stomatitis Virus (VSV-G), which allows packaged particles to infect virtually any mammalian cell type. LV particles can be purified to high titres making them a very effective delivery vehicle for gene therapy.

A preferred type of lentiviral vector is based on Equine Infectious Anaemia Virus (EIAV).

AAV vectors are non-pathogenic and less immunogenic compared with other viral vectors. The ability of AAV vectors to infect both dividing and non-dividing cells, and to direct long-term gene expression in these tissues makes it an ideal vehicle for gene therapy. Moreover, AAV has a variety of pseudotypes with different tissue tropisms. A preferred AAV vector is the double stranded AAV pseudotype 8 (dsAAV8).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order to produce the proteins needed to replicate and package the AAV-based heterologous construct into nascent virion, the rep and cap proteins must be provided in trans. The helper functions normally provided by co-infection with the helper virus, such as adenovirus or herpesvirus, can also be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as ddRNAi vectors.

The expression of the ddRNAi agents of the invention following viral delivery will be durable, potentially up to the life of a patient, from a single administration of the drug. Accordingly, in another aspect of the invention, there is provided a ddRNAi construct comprising a viral vector into which a ddRNAi expression cassette according to the invention is inserted. Preferably the expression cassette encodes for multiple RNAi agents, as either long hairpin structures or multiple hairpin structures. In one embodiment, the viral vector is an MV vector. In a preferred embodiment, the effector sequences and the effector complement sequences of the ddRNAi agents are expressed within a miRNA structure.

After generation of the viral based ddRNAi construct, the construct is packaged into viral particles. Any method known in the art may be used to produce infectious viral particles whose genome comprises a copy of the viral ddRNAi construct. One method utilizes packaging cells that stably express in trans the viral proteins that are required for the incorporation of the viral ddRNAi construct into viral particles, as well as other sequences necessary or preferred for a particular viral delivery system (for example, sequences needed for replication, structural proteins and viral assembly) and either viral-derived or artificial ligands for tissue entry. Following transfection of the viral ddRNAi construct into packaging cells, the packaging cells then replicate viral sequences, express viral proteins and package the ddRNAi expression constructs into infectious viral particles. The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with one or more constructs to achieve efficient production of functional particles. One of the constructs is the viral based ddRNAi construct; the other construct comprises nucleic acids encoding the proteins necessary to allow the cells to produce functional virus as well as other helper functions.

The packaging cell line or replication and packaging construct may not express envelope gene products. In these embodiments, the gene encoding the envelope gene can be provided on a separate construct that is co-transfected with the viral based ddRNAi construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells). In addition, genetically-modified ligands can be used for cell-specific targeting.

After production in a packaging cell line, the viral particles containing the ddRNAi expression cassettes are purified and quantified (titred). Purification strategies include density gradient centrifugation, or, preferably, column chromatographic methods.

Alternatively, minicircles such as those described in US20040214329 may be used to deliver the ddRNAi expression cassettes. Minicircles provide for persistently high levels of nucleic acid transcription, and are characterised by being devoid of expression-silencing bacterial sequences.

Methods

Administration of ddRNAi agents, ddRNAi constructs of siRNA agents of the invention inhibits expression of genes expressed in a pain-transmitting neuron. Accordingly, in another aspect of the invention, there is provided a method of treating pain in an individual comprising the administration of a therapeutically effective amount of a ddRNAi construct to a patient in need of treatment, wherein the ddRNAi agent inhibits expression of one or more target sequences in a pain-associated gene, preferably a PKCγ gene. The ddRNAi agent to be administered to the patient may be one or more of:

ddRNAi agent comprising a first effector sequence; and a first effector complement sequence; wherein the effector sequence is substantially complementary to a predicted transcript of a region of the target gene ddRNAi agent comprising, in a 5' to 3' direction, a first effector sequence; a second effector sequence; a second effector complement sequence; and a first effector complement sequence, wherein each effector sequence is substantially complementary to a predicted transcript of a region of the target gene a ddRNAi agent comprising, in a 5' to 3' direction, a first effector sequence; a second effector sequence; a third effector sequence; a third effector complement sequence; a second effector complement sequence; and a first effector complement sequence wherein each effector sequence is substantially complementary to a predicted transcript of a region of the target gene a ddRNAi agent comprising, in a 5' to 3' direction, a first effector sequence; a first effector complement sequence; a second effector sequence; and a second effector complement sequence wherein each effector sequence is substantially complementary to a predicted transcript of a region of the target gene a ddRNAi agent comprising, in a 5' to 3' direction, a first effector sequence; a first effector complement sequence; a second effector sequence; a second effector complement sequence; a third effector sequence; and a third effector complement sequence; wherein each effector sequence is substantially complementary to a predicted transcript of a region of the target gene a ddRNAi agent comprising, in a 5' to 3' direction, a first effector sequence; a second effector sequence; a sequence of 2 to 100 non-self-complementary nucleotides; a second effector complement sequence; and a first effector complement sequence wherein each effector sequence is substantially complementary to a predicted transcript of a region of the target gene a ddRNAi agent comprising, in a 5' to 3' direction, a first effector sequence; a sequence of 2 to 100 non-self-complementary nucleotides; a first effector complement sequence; a second effector sequence; a sequence of 2 to 100 non-self-complementary nucleotides; and a second effector complement sequence wherein each effector sequence is substantially complementary to a predicted transcript of a region of the target gene any of the abovementioned ddRNAi agents expressed within and as part of a miRNA structure wherein each effector complement sequence is substantially complementary to its corresponding effector sequence.

As would be understood by one skilled in the art, and as illustrated in the Figures, any particular effector sequence may be swapped in position with its complement in the agent. In particular forms of each of the embodiments described above, each effector sequence is at least 17 nucleotides in length selected from the group consisting of any 10 or more and preferably any 17 or more contiguous nucleotides within a sequence from any one of SEQ ID NOS: 19-36. The effector sequences may all be the same, or may all be different, or may be a combination eg 2 effector sequences of at least 10 contiguous nucleotides of SEQ ID NO:21 and 1 effector sequence of at least 10 contiguous nucleotides of (for example) SEQ ID NO: 22.

Preferably, the effector sequence is selected from the group consisting of any contiguous 11, 12, 13, 14, 15 or 16 nucleotides within any one of SEQ ID NOS: 19-36, and most preferably 17 or more contiguous nucleotides within any one of SEQ ID NOS: 19-36. Typically, the effector complement will be about the same length, or about the same length (ie ±15% nucleotide length, or 1 to 3 nucleotides different depending on the overall length) as its corresponding effector sequence.

Each of these ddRNAi agents may be administered via a ddRNAi expression cassette in a ddRNAi construct, as described in the earlier sections of the specification. Multiple targeting may be achieved by delivering two or more ddRNAi expression cassettes or constructs each capable of expressing a single ddRNAi agent, or alternatively, by delivering one or more ddRNAi expression cassettes or constructs each capable of expressing more than one ddRNAi agent.

In alternative embodiments, each of the effector sequences may be 100% complementary to a predicted transcript of a region of the target gene, or may only vary by 1, 2, 3, 4 or 5 nucleotides.

The method of treating pain can optionally include a preliminary step of identifying an individual having pain requiring treatment.

For longer term or stable provision of the ddRNAi agents of the invention, the ddRNAi agent is provided via a ddRNAi construct of the invention ie in vivo expression of the ddRNAi agent from a ddRNAi expression cassette inserted into a suitable vector delivered to the cell. The ddRNAi expression cassette comprises:

one or more promoter sequences one or more DNA sequences selected from the group consisting of sequences that encode for any 10 or more contiguous nucleotides within a sequence from SEQ ID NOS: 19-36;

one or more DNA sequences that encode for one or more effector complement sequences;

and optionally one or more DNA sequences that encode for loop sequences;

one or more terminator sequences; and one or more enhancer sequences.

As outlined earlier in the specification, these components of the ddRNAi expression cassette may have different 5' to 3' arrangements, all of which are suitable for use in the methods of the invention. The expression cassette preferably also includes DNA sequences that encode sequence capable of forming a miRNA structure.

Preferably, the target pain-associated gene is the protein kinase C γ gene (PKCγ). Accordingly, in one embodiment of the invention, the ddRNAi agent inhibits expression of one or more target sequences in the PKCγ gene. The DNA sequence that encodes for the first effector sequence is preferably selected from the ddRNAi effector encoding sequences of any 10 or more contiguous nucleotides within a sequence from SEQ ID NOS: 19-26 listed in column of Table 2. Alternatively, as detailed earlier, the sequence that encodes for the effector sequence may vary from SEQ ID NOS: 19-26 by 1, 2, 3, 4 or 5 nucleotides without effecting the ability of the sequence encoded to base pair with the target sequence and inhibit expression of the pain-associated gene target sequence.

Typically, each effector sequence forms a double stranded region with the corresponding effector complement sequence.

In an alternative embodiment, the target pain-associated gene is D-amino acid oxidase (DAO) gene. In an alternative embodiment, the method of treating pain in an individual comprises the administration of a therapeutically effective amount of a ddRNAi construct that encodes a ddRNAi agent having more than one effector sequence, such as those listed above.

In an alternative embodiment, a ddRNAi agent or siRNA agent of the invention produced in vitro may be administered.

The pain to be treated is preferably chronic pain. By "chronic" it is meant that the pain is long-lasting or persistent. There are two types of chronic pain—nociceptive and neuropathic. Nociceptive pain is caused by damage to body tissue and usually described as a sharp, aching, or throbbing pain. This kind of pain can be due to benign pathology; or by tumors or cancer cells that are growing larger and crowding other body parts near the cancer site. Nociceptive pain may also be caused by cancer spreading to the bones, muscles, or joints, or that causes the blockage of an organ or blood vessels.

In one embodiment, there is providing a method of treating pain in a subject with cancer comprising the administration of a therapeutically effective amount of a ddRNAi construct of the invention to the subject. The patient with cancer may also be receiving other treatments for the cancer itself, such that the ddRNAi construct administered is an adjunct therapy.

When treating chronic pain, it is preferable that the ddRNAi construct is administered and either stably maintained or integrated in to the target cell to ensure longer term expression of the ddRNAi agent. As detailed above, this can be achieved with the use of a ddRNAi construct having a viral vector backbone. In accordance with this, there is provided a method of treating chronic pain in an individual comprising the administration of a therapeutically effective amount of a ddRNAi construct of the invention to a patient in need of treatment.

Treatment of chronic pain is aimed at reducing the transmission of the pain by interfering with genes expressing neurotransmitters. There is therefore provided a method of reducing the pain in an individual, comprising administering to the individual a ddRNAi constructs of the invention to target a gene, preferably the PKCγ gene, in a localised region of the spinal cord.

Neuropathic pain occurs when there is actual nerve damage. Nerves connect the spinal cord to the rest of the body and allow the brain to communicate with the skin, muscles and internal organs. Nutritional imbalance, alcoholism, toxins, infections or auto-immunity can all damage this pathway and cause pain. Neuropathic pain can also be caused by a cancer tumor pressing on a nerve or a group of nerves (although cancer pain can be nociceptive or neuropathic). People often describe this pain as a burning or heavy sensation, or numbness along the path of the affected nerve.

Alternatively, treatment of acute pain may not require long term treatment, and it may in fact be preferred to rely on the transient presence of a ddRNAi agent or siRNA agent as opposed to long term expression of ddRNAi agents from integrated or stably maintained ddRNAi constructs. By "acute" it is meant that the pain has a rapid onset, and/or a short duration. In accordance with this embodiment of the invention, there is provided a method of treating acute pain in an individual comprising the administration of a therapeutically effective amount of a ddRNAi agent to a patient in need of treatment, for inhibiting expression of one or more target sequences in a pain-associated gene, the ddRNAi agent comprising at least:
  a first effector sequence of at least 17 nucleotides in length selected from any 10 or more contiguous nucleotides within a sequence from the group consisting of SEQ ID NOS: 19-26; and
  a first effector complement sequence wherein the first effector complement sequence is substantially complementary to the first effector sequence;
wherein the effector sequence is substantially complementary to a predicted transcript of a region of the pain-associated gene, wherein the pain-associated gene is PKCγ. In this embodiment, the ddRNAi agent of the invention is produced in vitro or chemically synthesised and provided to the cell.

Preferably, the pain associated target gene is the PKCγ gene. Accordingly, in one embodiment of the invention, the ddRNAi agent inhibits expression of one or more target sequences in a PKCγ gene. The first effector sequence is preferably selected from any 10 or more and preferably any 17 or more contiguous nucleotides within a sequence from the effector sequences SEQ ID NOS: 19-26 listed in Table 2, preferably SEQ ID NOS: 21-23. Alternatively, the effector sequence may vary from SEQ ID NOS: 19-26 by 1, 2, 3, 4 or 5 nucleotides without affecting the ability of the effector sequence to base pair with the target sequence and inhibit expression of the PKCγ gene.

In an alternative embodiment, an siRNA agent may be administered. Preferably the siRNA agents, similarly to the ddRNAi agent, targets the PKCγ gene, and may have a sequence selected from any 10 or more and preferably any 17 or more contiguous nucleotides within a sequence from the group consisting of SEQ ID NOS: 19-26, or may vary from SEQ ID NOS: 19-26 by 1, 2, 3, 4 or 5 nucleotides without affecting the ability of the effector sequence to base pair with the target sequence and inhibit expression of the PKCγ gene.

Alternatively, if seeking to target the DAO gene, the effector sequences of a ddRNAi agent or siRNA agent are selected from SEQ ID NOS: 27-36.

Administration of a ddRNAi agent or siRNA agent of the invention to an individual can also prevent acute or chronic pain, minimize the severity or frequency of acute or chronic pain, or inhibit acute or chronic pain from becoming more intense.

In another embodiment, the invention provides a method for increasing the sensitivity of a subject in need of pain relief, or rendering a subject in need of pain relief sensitive to, treatment with other pain relievers, such as opiates including morphine. Tolerance to the analgesic effects of morphine for example can develop fairly rapidly in patients. The method involves administering a ddRNAi agent, ddRNAi expression cassette or ddRNAi expression construct or composition of the invention to a subject who is no longer responsive to other pain relief due to resistance or tolerance of the analgesic effects.

Administration of a ddRNAi agent, ddRNAi expression cassette or ddRNAi expression construct or composition of the invention can also slow down the development of tolerance to a pain reliever in a subject receiving that pain reliever.

In another aspect of the invention, there is provided the use of the ddRNAi constructs, ddRNAi agents and siRNA agents of the invention in the preparation of medicaments for treatment of pain, preferably chronic pain.

In another aspect of the invention, there is provided the use of the ddRNAi constructs, ddRNAi agents or siRNA agents of the invention in the preparation of medicaments for treatment of acute or chronic pain, prevention of acute or chronic pain, the reduction of the severity or frequency of acute or chronic pain, the inhibition of acute or chronic pain becoming more intense, or increasing or restoring a subject's sensitivity to other pain relievers, particularly opiates such as morphine. Preferably, the medicament is for chronic pain.

In a further aspect of the invention there is provided ddRNAi constructs, ddRNAi agents or siRNA agents for treating acute or chronic pain, preventing acute or chronic pain, reducing the severity or frequency of acute or chronic pain, or inhibiting acute or chronic pain from becoming more intense. Preferably, the pain is chronic pain.

In a further aspect of the invention there is provided a composition comprising ddRNAi constructs, ddRNAi agents or siRNA agents as an active ingredient for treating acute or chronic pain, preventing acute or chronic pain, reducing the severity or frequency of acute or chronic pain, inhibiting acute or chronic pain from becoming more intense or increasing or restoring a subject's sensitivity to other pain relievers, particularly opiates such as morphine. Preferably, the pain is chronic pain.

The one or more effector sequences' of the ddRNAi constructs, ddRNAi agents or siRNA agents used in the methods of the invention comprise any 10 or more, preferably any 17 or more, contiguous nucleotides within sequences able to inhibit the expression of the pain associated target gene region by at least 70%. Preferably the one or more effector sequence is selected from SEQ ID NOS:

19-36, more preferably SEQ ID NOS: 19-26, and most preferably SEQ ID NOS: 21-23.

In each of the embodiments described above, ddRNAi constructs, ddRNAi agents or siRNA agents can be used in combination with other known treatments to treat or prevent the pain conditions discussed herein. For example, the described molecules can be used in combination with one or more known therapeutic agents to treat pain or other conditions which respond to the modulation of PKCγ or DAO expression. Such agents include, but not limited to pregabalin, hydromorphone, narcotics, codeine, hydrocodone, acetominophen, nonsteroidal anti-inflammatory drugs (NSAIDS), COX-2 inhibitors, duloxetine, propoxyphene, caffeine, flexeril, levetiracetam, meloxicam, morphine, morphine sulphate, naproxen, gabapentin, oxycontin, paroxetine and other selective serotinin reuptake inhibitors (SSRI), oxycodone, nabumetone, methocarbamol, quetiapine, metaxalone, carisoprodol, carbamazepine, tramadol, diazepam and tizanidine.

Pharmaceutical Compositions

The ddRNAi agents, the siRNA agents or the vectors comprising ddRNAi expression cassettes of the invention can be formulated into pharmaceutical compositions by combination with appropriate, pharmaceutically acceptable carriers or diluents. Accordingly, there is provided a pharmaceutical composition comprising a ddRNAi agent, a ddRNAi expression cassette, a ddRNAi construct or a siRNA agent of the invention and a pharmaceutically acceptable carrier or diluent.

In pharmaceutical dosage forms, the agents or the vectors comprising the ddRNAi expression cassettes may be administered alone or in association or combination with other pharmaceutically active compounds. Those with skill in the art will appreciate readily that dose levels for agents or vectors comprising the ddRNAi expression cassettes will vary as a function of the nature of the delivery vehicle, the relative ease of transduction of the target cells, the expression level of the RNAi agents in the target cells and the like.

The ddRNAi agents, the siRNA agents or the vectors comprising ddRNAi expression cassettes of the invention can be formulated into preparations for injection or administration by dissolving, suspending or emulsifying them in an aqueous or non aqueous solvent, such as oils, synthetic aliphatic acid glycerides, esters of higher aliphatic acids or propylene glycol; and if desired, with conventional additives such as solubilisers, isotonic agents, suspending agents, emulsifying agents, stabilizers and preservatives.

Pharmaceutically acceptable carriers or diluents contemplated by the invention include any diluents, carriers, excipients, and stabilizers that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as plasma albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The pharmaceutical composition may be prepared for various routes and types of administration. In general the formulations are prepared by uniformly and intimately bringing into association the active ingredient with liquid carriers or finely divided solid carriers or both, and if necessary, shaping the product. Formulation may be conducted by mixing at ambient temperature at the appropriate pH, and at the desired degree of purity, with physiologically acceptable carriers, i.e., carriers that are non-toxic to recipients at the dosages and concentrations employed.

The one or more effector sequences of the ddRNAi constructs, ddRNAi agents or siRNA agents used in the compositions of the invention comprise any 10 or more, preferably any 17 or more, contiguous nucleotides within sequences able to inhibit the expression of the pain associated target gene region by at least 70%. Preferably the one or more effector sequence is selected from SEQ ID NOS: 19-36, more preferably SEQ ID NOS: 19-26, and most preferably SEQ ID NOS: 21-23.

In another embodiment there is provided a kit or article of manufacture including an RNAi agent or pharmaceutical composition as described above.

In other embodiments there is provided a kit for use in a therapeutic application mentioned above, the kit including:
a container holding a RNAi agent or pharmaceutical composition;
a label or package insert with instructions for use.

In certain embodiments the kit may contain one or more further active principles or ingredients for treatment or prevention of a pain or for treating or preventing a pain-related complication described above, or a condition or disease associated with PKCγ expression.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds an RNAi agent or pharmaceutical composition which is effective for treating the condition and may have a sterile access port (for example the container may be an intravenous solution bag or a vial having a stopper pierceable by a hypodermic injection needle). The label or package insert indicates that the RNAi agent or pharmaceutical composition is used for treating the condition of choice. In one embodiment, the label or package insert includes instructions for use and indicates that the RNAi agent or pharmaceutical composition can be used to treat or prevent pain or to treat or prevent a complication stemming from pain.

The kit may comprise (a) an RNAi agent or pharmaceutical composition; and (b) a second container with a second active principle or ingredient contained therein. The kit in this embodiment of the invention may further comprise a package insert indicating that the RNAi agent or pharmaceutical composition and other active principle can be used to treat or prevent a disorder or treat or prevent a complication stemming from pain. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments an RNAi agent or pharmaceutical composition may be provided in the form of a device, disposable or reusable, including a receptacle for holding the RNAi agent or pharmaceutical composition. In one embodiment, the device is a syringe. The device may hold 1-2 mL of the RNAi agent or pharmaceutical composition. The RNAi agent or pharmaceutical composition may be provided in the device in a state that is ready for use or in a state requiring mixing or addition of further components.

The invention is now described with reference to the following non-limiting examples.

EXAMPLES

1. PKCγ Construct Design and Creation for In Vitro Silencing ddRNAi constructs expressing shRNAs targeting PKCγ were designed, using the criteria described above, to recognise target sequences in PKCγ mRNA that were conserved between human and the pre-clinical test species rat and macaque (BLTPKC1, BLTPKC2, BLTPKC5 and BLTPKC7), some constructs (BLTPKC3, BLTPKC4, BLTPKC6 and BLTPKC8) also target conserved sequences in dog. ddRNAi constructs were cloned into a lentiviral vector by Sigma Aldrich (St Louis, Mo.) and packaged lentiviral particles were also prepared from these by Sigma Aldrich.

Briefly sequences encoding the shRNAs were cloned into the lentiviral vector PLKO.1-puro that uses the U6 promoter to drive shRNA expression; the vector carries a puromycin resistance gene to permit selection of transformed cells and contains all sequences necessary for packaging as viral particles and integrating into mammalian genomes. Lentiviral particles were prepared and packaged using HEK293T cells and appropriate packaging vectors (Sigma Aldrich), resulting in particles which were pseudotyped with an envelope G glycoprotein from Vesicular Stomatitis Virus (VSV-G) at titres of $1.0 \times 10^6$ TU/ml. Lentiviral preps were prepared from 8 ddRNAi constructs (expressing effector sequences SEQ ID NOS: 19-26); maps of such constructs and the sequences of shRNAs are shown in FIG. 2.

2. In Vitro Silencing of PKCγ

Rat C6 cells were infected with serial dilutions of lentiviral particles and transformed cells selected with puromycin (8 μg/ml). Cultures containing 20-50 transformed colonies were expanded and RNA isolated from these using an RNAqueous®-4PCR Kit (Applied Biosystems). PKCγ mRNA levels in these cultures were determined using qRT-PCR assays—parallel assays for GAPDH mRNA levels were used as internal controls. cDNAs were prepared using a High Capacity RNA-to-cDNA Kit (Applied Biosystems) and qRT PCR assays used commercial kits (Applied Biosystems) according to the manufacturer's protocol. Results from these experiments are shown in FIG. 3.

These data showed that the constructs BLTPKC3 and BLTPKC4 strongly silenced rat PKCγ expression, BLTPKC 5 gave moderate silencing, BLT PKC 6 and 7 gave little if any silencing and BLT PKC8 had no effect. These results illustrate that selecting appropriate target sequences is not routine. Despite all of these targets being seemingly suitable target sequences on paper, particularly given the high conservation between species, some effector sequences work much more effectively to silence the target. It is therefore not predictable which sequences are able to be silenced by mere visual inspection of the sequence itself, let alone to what extent they may be silenced, and if that would be sufficient for the purposes of the invention.

3. DAO Construct Design and Creation for In Vitro Silencing ddRNAi constructs expressing shRNAs targeting DAO were designed to recognise target sequences in rat and human DAO mRNAs. DNA constructs and packaged lentiviral particles were prepared by Sigma Aldrich as described above. Packaged lentiviral particles were prepared for 5 ddRNAi constructs targeting rat DAO mRNA (expressing effector sequences SEQ ID NOS: 27, 29, 31, 33 and 35) and 5 sequences targeting homologous regions of human DAO mRNA (expressing effector sequences SEQ ID NOS: 28, 30, 32, 34 and 36); sequences of shRNAs and predicted effector sequences are shown in FIG. 4.

4. In Vitro Silencing of DAO

Rat C6 cells will be infected with serial dilutions of lentiviral particles and transformed cells selected with puromycin (8 μg/ml). Cultures containing 20-50 transformed colonies will be expanded and RNA isolated from these using an RNAqueous®-4PCR Kit (Applied Biosystems). DAO mRNA levels in these cultures will be determined using qRTPCR assays—parallel assays for rat GAPDH mRNA levels will be used as internal controls. cDNAs will be prepared using a High Capacity RNA-to-cDNA Kit (Applied Biosystems) and qRT PCR assays will use commercial kits (Applied Biosystems) according to the manufacturer's protocol, and constructs showing strong silencing selected.

5. PKCγ Construct Design and Creation for In Vivo Silencing

To test for pain relief in rats, two ddRNAi constructs and two controls were prepared for cloning into a lentiviral vector. The constructs were synthesised in vitro by GenScript Corp. The two active constructs were based on targeting SEQ ID NO: 3 of PKCγ with an effector sequence of SEQ ID NO: 21, and targeting SEQ ID NO: 4 of PKCγ with an effector sequence of 22. They were designated BOPKC3 (which expresses a single effector sequence, SEQ ID NO: 21) and BOPKC3&4 (which expresses two effector sequences, SEQ ID NO: 21 and SEQ ID NO:22)

The two control constructs were designed to express randomised shRNAs based on BOPKC3 and BOPKC3&4 and are designated BOPKC3cont and BOPKC3&4cont and listed as SEQ ID NOS:47 and SEQ ID NOS:48 respectively. Maps of the constructs and sequences of the predicted shRNAs and effector sequences once processed by Dicer are shown in FIG. 5.

6. DAO Construct Design and Creation for In Vivo Silencing

The efficacy of the constructs BOPKC3 and BOPKC3&4 in relieving neuropathic pain, will be tested in rat pain models for mechanical allodynia and thermal hyperalgesia, using test systems well known to those familiar with the art (eg Zou et al, 2011). The constructs BOPKC3cont and BOPKC3&4cont will be used as negative controls.

Briefly male Sprague-Dowley rats will be subject to chronic constriction injury (CCI), where the left sciatic nerve will be tied with ligatures. After recovery cannula will be placed intrathecally (IT) into animals and lentiviral particles (10 μl at 1×10E9 TU/ml (Transduction Units/ml)) introduced into the spinal cord (n=10 for each treatment). Mechanical allodynia will be assayed by determining von Frey paw withdrawal thresholds (PWTs) and thermal hyperalgesia will be assayed by measuring paw withdrawal thermal latency (PWTL) in treated animals. Neuropathic pain will be monitored for up to 8 weeks by determining PWTs and PWTLs at least twice a week for all test animals. Pain relief will manifest as an increase in PWT and PWTL scores in animals treated with shRNAs targeting PKCγ (BOPKC3 and BOPKC3&4) compared to animals treated with control constructs (BOPKC3cont and BOPKC3&4cont).

7. PKCγ Constructs Expressing RNAi Effectors Embedded in miRNA Derived Sequences A ddRNAi construct was designed to express RNAs mimicking the structure of endogenous miRNAs (FIG. 6A). The BLTPKC3miR construct (SEQ ID NO: 69) expresses an RNA (SEQ ID NO: 71) that targets SEQ ID NO:3 with an effector sequence of SEQ ID NO:21. The sequence and predicted structure are shown in FIG. 6B. The BLTPKC4miR construct (SEQ ID NO: 70) expresses an RNA (SEQ ID NO: 72) that targets SEQ ID NO:4 with an effector sequence of SEQ ID NO:22. The sequence and predicted structure are shown in FIG. 6C. These constructs will be tested in vitro as outlined in Examples 1 and 2 and in vivo as described in Example 5.

It should be understood that while the invention has been described in detail herein, the examples are for illustrative purposes only. Other modifications of the embodiments of the present invention that are obvious to those skilled in the art of molecular biology, pain treatment, and related disciplines are intended to be within the scope of the invention.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

REFERENCES

Celerier et al, 2004. *Neropharmacolgy* 46: 264-272.
Christoph et al., 2008. *Mol Cell Neurosci* 37:579-8
Dorn et al., 2004. *Nucleic Acids Res* 32:e49
Garraway et al., 2007. *J Pharmacol Exp Therapeut* 322: 982-8
Gu et al, 2012. *Cell* 151: 900-911.
Frank et al., 2010. *Nature*. 465:818-22
Kawasaki et al., 2008. *Nat Med* 14:331-6,
Lin et al., 2006. *J Pharmacol Exp Ther* 319:1096-1103
McBride et al, 2008. *PNAS* 105:5868-5873.
Peviani et al, 2012. *J Neurosci Methods* 205: 139-147.
Schwarz et al., 2003. *Cell* 115: 199-208
Tan et al., 2005. *Gene Ther* 12: 59-66
Vit et al., 2008. *J Neurosci* 28:4161-71
Wang et al, 2011. *Mol Neorodegener* 2: 75.
Wu et al 2011. *PLoS ONE* 6:e28580
Yonaha and Proudfoot, 2000. *EMBO J.* 19:3770-3777
Zou et al., 2011. *Human Gene Therapy* 22:465-475
Zhao et al, 2008. *Cell Mol Neurobiol* 28:581-591.
Zhao et al, 2010. *J Pharmacol Exp Therapeut* 332:248-254.

---

The invention claimed is:

1. A DNA-directed RNA interference (ddRNAi) agent for inhibiting expression of one or more target sequences in a pain associated gene, the ddRNAi agent comprising, in a 5' to 3' direction:
   an effector sequence set forth in SEQ ID NO: 23; and
   an effector complement sequence, wherein the effector complement sequence is substantially complementary to the effector sequence.

2. A ddRNAi agent according to claim 1, wherein the pain associated gene is protein kinase C-γ (PKCγ).

3. A ddRNAi agent according to claim 1, comprising, in a 5' to 3' direction:
   a first effector sequence of at least 17 nucleotides in length;
   a second effector sequence of at least 17 nucleotides in length;
   a second effector complement sequence, wherein the second effector complement sequence is substantially complementary to the second effector sequence; and
   a first effector complement sequence, wherein the first effector complement sequence is substantially complementary to the first effector sequence;
   wherein one of the first and second effector sequences is the sequence set forth in SEQ ID NO: 23 and the other effector sequence is substantially complementary to a predicted transcript of a region of the pain-associated.

4. A ddRNAi agent according to claim 1, comprising, in a 5' to 3' direction:
   a first effector sequence of at least 17 nucleotides in length;
   a first effector complement sequence, wherein the first effector complement sequence is substantially complementary to the first effector sequence;
   a second effector sequence of at least 17 nucleotides in length; and
   a second effector complement sequence, wherein the second effector complement sequence is substantially complementary to the second effector sequence;
   wherein one of the first and second effector sequences is the sequence set forth in SEQ ID NO: 23 and the other effector sequence is substantially complementary to a predicted transcript of a region of the pain-associated gene.

5. A ddRNAi agent according to claim 1, wherein the target sequence in the pain-associated gene is set forth in SEQ ID NO: 5.

6. A ddRNAi expression cassette for expressing a ddRNAi agent according to claim 1, the expression cassette comprising:

one or more promoter sequences;

one or more DNA sequences that encode for one or more effector sequences; and one or more DNA sequences that encode for one or more effector complement sequences;

and optionally:

one or more DNA sequences that encode for a loop sequence;

one or more terminator sequences; and/or one or more enhancer sequences.

7. A ddRNAi expression cassette according to claim 6 further comprising miRNA expressing sequences, and wherein the ddRNAi agent is expressed within, and as part of, a miRNA structure.

8. A ddRNAi expression construct comprising a ddRNAi expression cassette according to claim 6.

9. A method of treating or preventing pain in a subject comprising administering a therapeutically effective amount of a ddRNAi expression construct of claim 8.

10. A method of reducing severity of pain in a subject comprising administering a therapeutically effective amount of a ddRNAi expression construct of claim 8.

11. A method according to claim 9, wherein the pain is chronic pain.

12. A method according to claim 9, wherein the pain is of neuropathic origin.

13. A pharmaceutical composition comprising a ddRNAi expression construct of claim 8 and a pharmaceutically acceptable carrier or diluent.

14. A ddRNAi expression construct comprising a ddRNAi expression cassette according to claim 6.

15. A method of treating or preventing pain, or reducing severity of pain, in a subject comprising administering a therapeutically effective amount of a ddRNAi expression construct according to claim 14.

16. A method according to claim 10, wherein the pain is chronic pain.

17. A method according to claim 15, wherein the pain is chronic pain.

18. A method according to claim 10, wherein the pain is of neuropathic origin.

19. A method according to claim 15, wherein the pain is of neuropathic origin.

20. A pharmaceutical composition comprising a ddRNAi expression construct of claim 14 and a pharmaceutically acceptable carrier.

21. A DNA-directed RNA interference (ddRNAi) agent for inhibiting expression of one or more target sequences in a pain associated gene, the ddRNAi agent comprising, in a 5' to 3' direction:

an effector sequence of at least 17 nucleotides in length; and an effector complement sequence, wherein the effector complement sequence is substantially complementary to the effector sequence; and wherein the effector sequence is substantially complementary to a predicted transcript of the target sequence set forth in SEQ ID NO: 5.

22. A ddRNAi agent according to claim 21, wherein the pain-associated gene is protein kinase C-γ (PKCγ).

23. A ddRNAi expression cassette for expressing a ddRNAi agent according to claim 21, the expression cassette comprising:

one or more promoter sequences;

one or more DNA sequences that encode for one or more effector sequences; and one or more DNA sequences that encode for one or more effector complement sequences;

and optionally:

one or more DNA sequences that encode for a loop sequences;

one or more terminator sequences;

one or more enhancer sequences; and/or one or more miRNA expressing sequences, such that ddRNAi agent is expressed within, and as part of, a miRNA structure.

24. A ddRNAi expression construct comprising a ddRNAi expression cassette according to claim 23.

25. A pharmaceutical composition comprising a ddRNAi expression construct of claim 24 and a pharmaceutically acceptable carrier or diluent.

* * * * *

SEQUENCE LISTING

```
<160> NUMBER OF SEQ ID NOS: 72

<210> SEQ ID NO 1
<211> LENGTH: 20
<212> TYPE: DNA
<213> ORGANISM: Homo sapiens

<400> SEQUENCE: 1
tgcaaggggt tcctgaccaa                                                  20

<210> SEQ ID NO 2
<211> LENGTH: 20
<212> TYPE: DNA
<213> ORGANISM: Homo sapiens

<400> SEQUENCE: 2
ggcctcttct tccttcacaa                                                  20

<210> SEQ ID NO 3
<211> LENGTH: 20
<212> TYPE: DNA
<213> ORGANISM: Homo sapiens

<400> SEQUENCE: 3
gacttcagct tcctcatggt                                                  20

<210> SEQ ID NO 4
```

-continued

```
<211> LENGTH: 20
<212> TYPE: DNA
<213> ORGANISM: Homo sapiens

<400> SEQUENCE: 4
agcctcctcc agaagtttga                                               20

<210> SEQ ID NO 5
<211> LENGTH: 20
<212> TYPE: DNA
<213> ORGANISM: Homo sapiens

<400> SEQUENCE: 5
tggccgatgc tgacaactgc                                               20

<210> SEQ ID NO 6
<211> LENGTH: 20
<212> TYPE: DNA
<213> ORGANISM: Homo sapiens

<400> SEQUENCE: 6
ggagggcgag tattacaatg                                               20

<210> SEQ ID NO 7
<211> LENGTH: 20
<212> TYPE: DNA
<213> ORGANISM: Homo sapiens

<400> SEQUENCE: 7
ggtgccatgt cctttggtgt                                               20

<210> SEQ ID NO 8
<211> LENGTH: 20
<212> TYPE: DNA
<213> ORGANISM: Homo sapiens

<400> SEQUENCE: 8
gcagcctcct ccagaagttt                                               20

<210> SEQ ID NO 9
<211> LENGTH: 20
<212> TYPE: DNA
<213> ORGANISM: Rattus rattus

<400> SEQUENCE: 9
gggaactgga gcgagctaaa                                               20

<210> SEQ ID NO 10
<211> LENGTH: 20
<212> TYPE: DNA
<213> ORGANISM: Homo sapiens

<400> SEQUENCE: 10
ggaaactgga gtgaactaaa                                               20

<210> SEQ ID NO 11
<211> LENGTH: 20
<212> TYPE: DNA
<213> ORGANISM: Rattus rattus

<400> SEQUENCE: 11
ggccggggcc agatcatcca                                               20
```

```
<210> SEQ ID NO 12
<211> LENGTH: 20
<212> TYPE: DNA
<213> ORGANISM: Homo sapiens

<400> SEQUENCE: 12
ggccgggggc agatcatgaa                                              20

<210> SEQ ID NO 13
<211> LENGTH: 20
<212> TYPE: DNA
<213> ORGANISM: Rattus rattus

<400> SEQUENCE: 13
ggcgtggatg tgattatcaa                                              20

<210> SEQ ID NO 14
<211> LENGTH: 20
<212> TYPE: DNA
<213> ORGANISM: Homo sapiens

<400> SEQUENCE: 14
ggcgcagacg tgattgtcaa                                              20

<210> SEQ ID NO 15
<211> LENGTH: 20
<212> TYPE: DNA
<213> ORGANISM: Rattus rattus

<400> SEQUENCE: 15
ggctgactga gaggttaact                                              20

<210> SEQ ID NO 16
<211> LENGTH: 20
<212> TYPE: DNA
<213> ORGANISM: Homo sapiens

<400> SEQUENCE: 16
ggctgactga aaggttaact                                              20

<210> SEQ ID NO 17
<211> LENGTH: 20
<212> TYPE: DNA
<213> ORGANISM: Rattus rattus

<400> SEQUENCE: 17
gaggcggagt ggaaccagca                                              20

<210> SEQ ID NO 18
<211> LENGTH: 20
<212> TYPE: DNA
<213> ORGANISM: Homo sapiens

<400> SEQUENCE: 18
gaggcggact ggagccaaca                                              20

<210> SEQ ID NO 19
<211> LENGTH: 20
<212> TYPE: RNA
<213> ORGANISM: Homo sapiens

<400> SEQUENCE: 19
uuggucagga accccuugca                                              20
```

```
<210> SEQ ID NO 20
<211> LENGTH: 20
<212> TYPE: RNA
<213> ORGANISM: Homo sapiens

<400> SEQUENCE: 20
uugugaagga agaagaggcc                                              20

<210> SEQ ID NO 21
<211> LENGTH: 20
<212> TYPE: RNA
<213> ORGANISM: Homo sapiens

<400> SEQUENCE: 21
accaugagga agcugaaguc                                              20

<210> SEQ ID NO 22
<211> LENGTH: 20
<212> TYPE: RNA
<213> ORGANISM: Homo sapiens

<400> SEQUENCE: 22
ucaaacuucu ggaggaggcu                                              20

<210> SEQ ID NO 23
<211> LENGTH: 20
<212> TYPE: RNA
<213> ORGANISM: Homo sapiens

<400> SEQUENCE: 23
gcaguuguca gcaucggcca                                              20

<210> SEQ ID NO 24
<211> LENGTH: 20
<212> TYPE: RNA
<213> ORGANISM: Homo sapiens

<400> SEQUENCE: 24
cauuguaaua cucgcccucc                                              20

<210> SEQ ID NO 25
<211> LENGTH: 20
<212> TYPE: RNA
<213> ORGANISM: Homo sapiens

<400> SEQUENCE: 25
acaccaaagg acauggcacc                                              20

<210> SEQ ID NO 26
<211> LENGTH: 20
<212> TYPE: RNA
<213> ORGANISM: Homo sapiens

<400> SEQUENCE: 26
aaacuucugg aggaggcugc                                              20

<210> SEQ ID NO 27
<211> LENGTH: 20
<212> TYPE: RNA
<213> ORGANISM: Rattus rattus

<400> SEQUENCE: 27
uuuagcucgc uccaguuccc                                              20
```

<210> SEQ ID NO 28
<211> LENGTH: 20
<212> TYPE: RNA
<213> ORGANISM: Homo sapiens

<400> SEQUENCE: 28
uuuaguucac uccaguuucc					20

<210> SEQ ID NO 29
<211> LENGTH: 20
<212> TYPE: RNA
<213> ORGANISM: Rattus rattus

<400> SEQUENCE: 29
uggaugaucu ggccccggcc					20

<210> SEQ ID NO 30
<211> LENGTH: 20
<212> TYPE: RNA
<213> ORGANISM: Homo sapiens

<400> SEQUENCE: 30
uucaugaucu gcccccggcc					20

<210> SEQ ID NO 31
<211> LENGTH: 20
<212> TYPE: RNA
<213> ORGANISM: Rattus rattus

<400> SEQUENCE: 31
uugauaauca cauccacgcc					20

<210> SEQ ID NO 32
<211> LENGTH: 20
<212> TYPE: RNA
<213> ORGANISM: Homo sapiens

<400> SEQUENCE: 32
uugacaauca cgucugcgcc					20

<210> SEQ ID NO 33
<211> LENGTH: 20
<212> TYPE: RNA
<213> ORGANISM: Rattus rattus

<400> SEQUENCE: 33
aguuaaccuc ucagucagcc					20

<210> SEQ ID NO 34
<211> LENGTH: 20
<212> TYPE: RNA
<213> ORGANISM: Homo sapiens

<400> SEQUENCE: 34
aguuaaccuu ucagucagcc					20

<210> SEQ ID NO 35
<211> LENGTH: 20
<212> TYPE: RNA
<213> ORGANISM: Rattus rattus

<400> SEQUENCE: 35

```
ugcugguucc acuccgccuc                                            20

<210> SEQ ID NO 36
<211> LENGTH: 20
<212> TYPE: RNA
<213> ORGANISM: Homo sapiens

<400> SEQUENCE: 36
uguuggcucc aguccgccuc                                            20

<210> SEQ ID NO 37
<211> LENGTH: 3143
<212> TYPE: DNA
<213> ORGANISM: Homo sapiens

<400> SEQUENCE: 37
cggagctgga gctcccaccg ccgccgcccg tgcctccggc tgccggcgcc cctgcctttg   60
gctcttcctc cccactcgcc cgctccccct ggcggagccg gcgcgcccgg ggtgccgctc  120
cctgcctggc gcgctccgca cctggaggtg ccttgcccct ctcctgccca cctcggaatt  180
tccctgtggc tcctttgatc cttcgagtct ccagctcctc tcccttccac ctgtttcccc  240
caagaaaggc aggatcctgg tccctgctac gtttctgggg ccatggctgg tctgggcccc  300
ggcgtaggcg attcagaggg gggacccccgg cccctgtttt gcagaaaggg ggccctgagg  360
cagaaggtgg tccacgaagt caagagccac aagttcaccg ctcgcttctt caagcagccc  420
accttctgca gccactgcac cgacttcatc tggggtatcg aaagcagggg cctgcaatgt  480
caagtctgca gctttgtggt tcatcgacga tgccacgaat ttgtgacctt cgagtgtcca  540
ggcgctggga agggccccca gacggacgac ccccggaaca acacaagtt ccgcctgcat   600 agctacagca gccccacctt ctgcgaccac tgtggctccc tcctctacgg gcttgtgcac  660
cagggcatga aatgctcctg ctgcgagatg aacgtgcacc ggcgctgtgt gcgtagcgtg  720 ccctcccctgt gcggtgtgga ccacaccgag cgccgcgggc gcctgcagct ggagatccgg  780
gctcccacag cagatgagat ccacgtaact gttggcgagg cccgtaacct aattcctatg  840
gaccccaatg tctctctga tccctatgtg aaactgaagc tcatcccaga ccctcggaac   900
ctgacgaaac agaagacccg aacggtgaaa gccacgctaa accctgtgtg aatgagacc   960 tttgtgttca acctgaagcc aggggatgtg gagcgccggc tcagcgtgga ggtgtgggac 1020
tgggaccgga cctcccgcaa cgacttcatg ggggccatgt cctttggcgt ctcggagctg 1080
ctcaaggcgc ccgtggatgg ctggtacaag ttactgaacc aggaggaggg cgagtattac 1140
aatgtgccgg tggccgatgc tgacaactgc agcctcctcc agaagtttga ggcttgtaac 1200
taccccctgg aattgtatga gcgggtgcgg atgggcccct cttcctctcc catcccctcc 1260
ccttccccta gtcccaccga ccccaagcgc tgcttcttcg gggcgagtcc aggacgcctg 1320
cacatctccg acttcagctt cctcatggtt ctaggaaaag gcagttttgg aaggtgatg  1380 ctggccgagc cagggcgctc tgatgagctc tacgccatca gatcttgaa aaaggacgtg  1440 atcgtccagg acgacgatgt ggactgcacg ctggtggaga acgtgtgct ggcgctgggg  1500 ggccggggtc ctggcggccg gccccacttc ctcacccagc tccactccac cttccagacc 1560
ccggaccgcc tgtatttcgt gatggagtac gtcaccgggg gagacttgat gtaccacatt 1620
caacagctgg gcaagtttaa ggagcccat gcagcgttct acgcggcaga aatcgctatc  1680
ggcctcttct tccttcacaa tcagggcatc atctacaggg acctgaagct ggacaatgtg 1740
atgctggatg ctgagggaca catcaagatc actgactttg gcatgtgtaa ggagaacgtc 1800
```

| | |
|---|---|
| ttccccggga cgacaacccg caccttctgc gggaccccgg actacatagc cccggagatc | 1860 |
| attgcctacc agccctatgg gaagtctgtc gattggtggt cctttggagt tctgctgtat | 1920 |
| gagatgttgg caggacagcc tcccttcgat ggggaggacg aggaggagct gtttcaggcc | 1980 |
| atcatggaac aaactgtcac ctaccccaag tcgctttccc gggaagccgt ggccatctgc | 2040 |
| aaggggttcc tgaccaagca cccagggaag cgcctgggct cagggcctga tggggaacct | 2100 |
| accatccgtg cacatggctt tttccgctgg attgactggg agcggctgga acgattggag | 2160 |
| atcccgcctc ctttcagacc ccgcccgtgt ggccgcagcg gcgagaactt tgacaagttc | 2220 |
| ttcacgcggg cggcgccagc gctgacccct ccagaccgcc tagtcctggc cagcatcgac | 2280 |
| caggccgatt ccagggcttc acctacgtg aaccccgact tcgtgcaccc ggatgcccgc | 2340 |
| agccccacca gcccagtgcc tgtgcccgtc atgtaatctc acccgccgcc actaggtgtc | 2400 |
| cccaacgtcc cctccgccgt gccggcggca gccccacttc accccaact tcaccacccc | 2460 |
| ctgtcccatt ctagatcctg caccccagca ttccagctct gccccgcgg gttctagacg | 2520 |
| cccctcccaa gcgttcctgg ccttctgaac tccatacagc ctctacagcc gtcccgcgtt | 2580 |
| caagacttga gcggagcccg atattctccc tgaccttagc gttctggact ctgccccaat | 2640 |
| cgggtccaga gaccacacca ctaaccatcc ccaactccat ggggttcgag actccatctt | 2700 |
| ggtagttctg tgcctccccc cagacccccgc ccctggggaa atagcctcac ggggttggct | 2760 |
| gttccagact caggttccag aacagccctc ggcctccgag gctccccgcc tccactctag | 2820 |
| ttctagatga gtgggaggcg tgccccccctc ctccagtacg tcccgctgct gtgctctggg | 2880 |
| gatttctggg atatatggag gattctttcc ccagaggctc ccaatcagct tttgttctag | 2940 |
| acttccccat cccgaagcca tcacttctcc ccgcagcccg cctgccgtgc atggctcctg | 3000 |
| tctggctcgg acccacccca actctcccca gtgcctgcca ctctctggga ctctcctcct | 3060 |
| cccctcctct tccccttagcc tctcccaccc ggccacagct gctggagaat aaatttggga | 3120 |
| tgctgatgaa aaaaaaaaaa aaa | 3143 |

<210> SEQ ID NO 38
<211> LENGTH: 3113
<212> TYPE: DNA
<213> ORGANISM: Rattus rattus

<400> SEQUENCE: 38

| | |
|---|---|
| cctagatgcc ccagtcttct actgctctga ccccacccgc tttctcccgg ctcggtacag | 60 |
| ctggtgccgg ggggtgctgc tttctgccct gcgctgcgca ccgttagtgc cctgcccctg | 120 |
| tccttccgat ctcagagtct gcggagtgcc cctatcgccg tccacctgtt tcctcagaaa | 180 |
| aaaggccagc tcgtgatccc tgctgcgttc ctggggccat gcgggtctg ggtcctggcg | 240 |
| ggggcgactc agaagggga ccccgacccc tgttttgcag aaaggggcg ctgaggcaga | 300 |
| aggtggtcca cgaggtgaag agccacaagt tcaccgctcg tttcttcaag cagccaacct | 360 |
| tctgcagtca ctgtaccgac ttcatctggg gcattggaaa gcagggcctg caatgtcaag | 420 |
| tctgcagctt tgtggttcac cgccgatgcc acgaatttgt gaccttcgag tgtccaggag | 480 |
| ctggaaaggg ccccccagacg gacgaccctc gcaacaagca caagttccgt ctgcacagct | 540 |
| acagcagtcc caccttctgc gaccactgtg gttccctcct ctacgggctg gtgcaccagg | 600 |
| gcatgaaatg ttcctgttgc gaaatgaatg tgcaccgacg ctgtgtgcgc agcgtgccct | 660 |
| cccctttgcgg cgtggaccat acagagcgcc gtggacgtct gcaactggaa atccgggctc | 720 |

| | |
|---|---|
| ccacatcaga tgagatccat attactgtgg gtgaggcccg gaacctcatt cctatggacc | 780 |
| ccaatggcct gtctgatccc tatgtgaaac tgaagctcat cccggaccct cggaacctga | 840 |
| caaaacagaa gacaaagacc gtgaaagcca cactgaatcc cgtgtggaac gagaccttcg | 900 |
| tgttcaacct gaagccgggg gatgtggagc gccggctcag tgtggaggtg tgggattggg | 960 |
| ataggacatc ccgaaatgac ttcatgggtg ccatgtcctt tggtgtctca gagctactca | 1020 |
| aggctcctgt ggatggatgg tacaagttac tgaaccagga ggagggcgag tattacaatg | 1080 |
| taccggtggc cgatgctgac aactgcagcc tcctccagaa gtttgaggcc tgtaattacc | 1140 |
| ccttggaatt gtatgagaga gtgcggatgg gcccctcttc ctctcccatt ccttctccat | 1200 |
| cccccagtcc cacggactcc aagagatgct tcttcggtgc cagcccagga cgcctgcata | 1260 |
| tctctgactt cagcttcctc atggttctag gaaaggcag ttttgggaag gtgatgctgg | 1320 |
| cagagcgcag aggatccgat gaactctatg ccatcaagat actgaaaaaa gacgtcattg | 1380 |
| tccaggatga tgatgtagac tgcacccttg tggagaagcg tgtgctggca ttggaggcc | 1440 |
| gaggtcctgg aggccggcca cactttctca cacaacttca ttccaccttt cagactccgg | 1500 |
| accgcctgta ttttgtgatg gagtacgtca ctgggggcga tttaatgtac cacattcagc | 1560 |
| aactgggcaa gtttaaggag ccccacgcag cattctatgc cgcggaaatc gccataggcc | 1620 |
| tcttcttcct tcacaaccag ggcatcatct acagggacct caagttggat aatgtgatgc | 1680 |
| tggatgctga aggacacatc aagatcacag acttcggcat gtgtaaagag aatgtcttcc | 1740 |
| ctgggtccac aacccgcacc ttctgtggga ccccagacta catagcacct gagatcattg | 1800 |
| cctatcagcc ctatgggaag tctgtcgact ggtggtcctt tggagtcctg ctgtatgaga | 1860 |
| tgttggcagg acagccaccc tttgatgggg aagatgagga ggagctgttt caagccatca | 1920 |
| tggaacaaac tgtcacctat cccaagtcac tttcccggga agctgtggcc atctgcaagg | 1980 |
| ggttcctgac caagcaccca ggaaagcgcc tgggctcagg ccagatggg aacccacca | 2040 |
| tccgggctca tggcttttc cgttggatcg attgggagag gttggagaga ctggaaattg | 2100 |
| cgcctccttt tagaccacgt ccgtgtggcc gcagcggcga aaactttgac aagttcttca | 2160 |
| cgcgggcagc gccagccttg accccgccag accgcttggt cctagccagc atcgaccaag | 2220 |
| ctgatttcca gggctttact tatgtgaacc cggacttcgt gcacccagat gcccgcagcc | 2280 |
| ccacaagccc tgtgcctgtg cccgtcatgt aatctcatct gctgccgcta ggtgttccca | 2340 |
| gtgctccctc cgccaagttg gctgtaactc ccatccaccc ccatcccgc ctctagtccg | 2400 |
| aattttaggt ctcttaaacc acccaacctt ctggcctctt tcacgcgccc caagtgggtt | 2460 |
| ctagacgctg ttccccagca ttgctggcat tttaaacttc aaacagtctc tagggccttt | 2520 |
| ctgtgttcta ggttcgttgt gctgagccct ggttttccc cacccccaac atctggatgc | 2580 |
| tgttccaact cttcccagaa accccactcc gtgtggggtt ctagactcta tcttggtagt | 2640 |
| tttatgcctt ctctctccct agaccacgtt gggagaaata gtctcatgag attgcctgct | 2700 |
| ccagactaag attccagatc agctctctgc atccttcaag gcccctccta cctccacttc | 2760 |
| agttgtagaa ttaagtggga ggctgggctc cgtgttccag gccacctccc ttccatgttc | 2820 |
| tgggattcc tggcatgcac ggaggattct ctccccgact tttctcagtc agcttttgtt | 2880 |
| ctagatttgt tccagaaccc ttcactgctc acctgccccg tgcatggctc cagccttggt | 2940 |
| cggaatcaca cacacacaca cacacacaca cacacacaca cacacacaca cacacacacc | 3000 |
| ccttgtcctc cgcagtgcct gccactttct gggactttct catccccac gcccttcctt | 3060 |
| tatcctctcc cacccagaca cagctgctgg agaataaatt tggagctctc gag | 3113 |

<210> SEQ ID NO 39
<211> LENGTH: 2228
<212> TYPE: DNA
<213> ORGANISM: Canis familiaris

<400> SEQUENCE: 39

| | | | | | |
|---|---|---|---|---|---|
| cgctccccct | ggcggagccg | gcgcgccccg | gggtgcggct | ccctgccctg | cactccgcgc | 60 |
| ctggaggtgc | ctcgcccctc | tccttccctc | ctcgcaatct | ccccgtggct | cagggctctc | 120 |
| ccgagtctcg | agtctccggc | tcctcgtcct | tccacctgtt | tccccagaa | aggcaggatc | 180 |
| ctggtccctg | caacgttcct | ggggccatgg | caggcctggg | ccccggcgga | ggcgattcag | 240 |
| agggggggacc | ccggcccctg | ttttgcagaa | agggggctct | gaggcagaag | gtggtccacg | 300 |
| aagtcaagag | tcacaagttc | accgcccgct | tcttcaagca | gccaaccttc | tgcagccact | 360 |
| gcaccgactt | catctggggc | attggaaaac | agggcctgca | atgtcaagtc | tgcagctttg | 420 |
| tggttcatcg | acgatgccac | gaatttgtga | ccttcgagtg | tccaggcgct | gggaagggcc | 480 |
| cccagacgga | tgaccccgc | aacaagcata | agttccgtct | acacagctac | agcagcccca | 540 |
| ccttttgcga | ccactgtggc | tccctgctct | acgggctggt | gcaccagggc | atgaaatgct | 600 |
| cctgctgcga | gatgaacgtg | caccgacgct | gtgtgcgcag | tgtgccttct | ctgtgcgggg | 660 |
| tggaccacac | cgagcgccgt | gggcgcctgc | agctggaaat | ccgagcacct | actgcagatg | 720 |
| aaattcatgt | cacagttggc | gaggcccgta | acctcatccc | aatggatccc | aatggtctgt | 780 |
| ctgatcccta | tgtgaagctg | aagctcatcc | cagaccctcg | gaacttgaca | aagcagaaga | 840 |
| cccggacggt | gaaagccacg | ctaaaccctg | tgggaacgag | accttcagac | agagatggag | 900 |
| ggcgctcaga | agaggagacg | caaacccaaa | gagacacaga | gacagagtgc | agggggtgga | 960 |
| gtgtaagcag | gggggtggtg | ggtgggtaca | agttactgaa | ccaggaggag | ggcgagtatt | 1020 |
| acaatgtgcc | tgtggctgat | gctgacaact | gcagcctcct | ccagaagttt | gagcgggtgc | 1080 |
| ggatgggtcc | ttcttcctct | cccatcccct | ctccatcccc | tagtcccacc | gactccaagc | 1140 |
| gctgtttctt | tgggacaagc | cccgacgtc | tgcacatctc | tgacttcagc | ttcctcatgg | 1200 |
| ttctaggaaa | aggcagtttt | gggaaggtga | tgctggctga | gcgcagggc | tcagatgagc | 1260 |
| tctacgccat | caagatcctg | aagaaggatg | tgattgtcca | ggatgacgat | gtggactgca | 1320 |
| ccctggtgga | gaagcgagtg | ctggccctgg | ggggccgagg | cccgggaggc | cggcccact | 1380 |
| ttctcaccca | actgcactcc | actttccaga | ccccggatcg | cctgtatttt | gtgatggagt | 1440 |
| atgtcaccgg | aggcgacttg | atgtaccaca | ttcagcagtt | gggcaaattt | aaggagcctc | 1500 |
| atgcagcgtt | ctacgctgcc | gaaatcgcca | tcgggctctt | cttcctgcac | aatcagggca | 1560 |
| tcatctaccg | ggacttgaag | ctagacaacg | tgatgcttga | tgccgaagga | cacatcaaaa | 1620 |
| tcactgactt | tggcatgtgt | aaggaaaacg | tctttcccgg | aaccacaacc | cgcactttct | 1680 |
| gcggaccc | agactacata | gcccctgaga | tcatcgccta | ccagcccat | gggaagtctg | 1740 |
| ttgattggtg | gtcctttggg | gttctgctgt | atgagatgct | ggcgggacag | ccccttttg | 1800 |
| atggggagga | tgaggaagag | ctcttttcagg | ccatcatgga | acaaacagtc | acttaccccca | 1860 |
| agtcgctttc | ccgggaagct | gtggcgatct | gcaagggggtt | cctaaccaag | cacccagcga | 1920 |
| agcgcctggg | ctcggggcca | gacggggagc | ctgccatccg | tgctcacggc | tttttccgct | 1980 |
| ggatggactg | ggagcgcttg | gagcgactgg | agatcgcgcc | tccgttcaga | ccccgccgt | 2040 |
| gtggacgcag | cggcgagaac | ttcgacaaat | tcttcacgcg | ggctgcgcca | gcgctgaccc | 2100 |

| | |
|---|---|
| cgccagaccg cctagttttg gccagcatcg accaggcgga tttccaaggc ttcacctacg | 2160 |
| tgaacccgga tttcgtgcac ccggacgccc gcagcccat cagcccaccg gctgtgcccg | 2220 |
| tcatgtaa | 2228 |

<210> SEQ ID NO 40
<211> LENGTH: 3177
<212> TYPE: DNA
<213> ORGANISM: Macaque

<400> SEQUENCE: 40

| | |
|---|---|
| acatttcagc aggtgccgga gctggagctc ccaccgccgc cgcccgtgcc tccggctccc | 60 |
| ggcgccgtgc ctttggctct cctccccac tcgcccgctc ccctggcgg agccggcgca | 120 |
| cccgggggtg ccgctccctg cctggcgcgc ttcgcacctg gaggtgcctt gcccctctcc | 180 |
| tacccacctc ggaatttccc tgtggctcct ttgatccttc gagtctccgg ctcctttccc | 240 |
| ttccacctgt ttcccccaag aaaggcagga tcctggtccc tgctacgtgt ctggggccat | 300 |
| ggctggtctg ggcccggcg gaggcgattc agaggggga ccccggcccc tgttttgcag | 360 |
| aaaggggct ctgaggcaga aggtggtcca cgaagtcaag agccacaagt tcaccgctcg | 420 |
| cttcttcaag cagcccacct tctgcagcca ctgcaccgac ttcatctggg gtatcggaaa | 480 |
| gcaaggcctg caatgtcaag tctgcagctt tgtggttcat cgacgatgcc acgaatttgt | 540 |
| gaccttcgag tgtccaggcg ctgggaaggg cccccagacg gacgaccccc ggaacaagca | 600 |
| caagttccgc ctgcatagct acagcagccc taccttctgc gaccactgtg gctccctcct | 660 |
| gtacgggctt gtgcaccagg gcatgaaatg ctcctgctgt gagatgaacg tgcaccggcg | 720 |
| ctgtgtgcgt agcgtgcccct ccctgtgcgg tgtggaccac accgagcgcc gcgggcgcct | 780 |
| gcagctggag atccgggctc ccactgcaga tgagatccac ataacggttg gcgaggcccg | 840 |
| taaccttatt cctatggacc ccaatggtct ctctgatccc tatgtgaaac tgaagctcat | 900 |
| cccagaccct cggaacctga cgaaacagaa aacccgaaca gtgaaagcca cgctaaatcc | 960 |
| tgtgtggaat gagaccttg tgttcaacct gaagcctggg gatgtggagc gccggctcag | 1020 |
| cgtggaggtg tgggactggg accgacctc ccgcaacgac ttcatgggtg ccatgtcctt | 1080 |
| tggcgtctca gagctgctca aggcgccagt ggatggctgg tacaagttac tgaaccagga | 1140 |
| ggagggcgag tattacaatg tgccggtggc cgatgctgac aactgcagcc tcctccagaa | 1200 |
| gtttgaggct tgtaactacc ccctggaatt gtatgagcgg gtgcggatgg gcccctcttc | 1260 |
| ctctcccatc ccctccccett ccccctagtcc caccgacccc aagcgctgct tcttcggggc | 1320 |
| aagcccagga cgtctgcaca tctccgactt cagcttcctc atggttctag aaaaggcag | 1380 |
| ttttgggaag gtgatgctgg ccgagcgcag aggctctgat gagctctacg ccatcaaaat | 1440 |
| cctgaaaaag gacgtgatcg tccaggatga cgacgtggac tgcacgctgg tggagaaacg | 1500 |
| cgtgctggcg ctgggggcc ggggtcctgg cggtcggccc cacttcctca cccaactcca | 1560 |
| ctccaccttc cagaccccgg accgcctgta tttcgtgatg gagtacgtca ccggggagag | 1620 |
| cttgatgtac cacattcaac agctgggcaa gtttaaggag ccccatgcag cgttctacgc | 1680 |
| agcagaaatc gccatcggcc tcttcttcct tcacaatcag gcatcatct acagggacct | 1740 |
| gaagctggac aatgtggtgc tggatgctga gggactcatc aagatcactg acttcggcat | 1800 |
| gtgtaaggag aacgtcttcc ccgggacgac aaccccgcacc ttctgcggga ccccggacta | 1860 |
| catagccccg gagatcattg cctaccagcc ctatgggaag tctgtcgatt ggtggtcctt | 1920 |
| tggagttctg ctgtatgaga tgttggcagg acagcctccc ttcgatgggg aggacgaaga | 1980 |

-continued

```
ggagctgttt caggccatca tggaacaaac tgtcacctac cccaagtcgc tttcccggga    2040
agccgtggcc atctgcaagg ggttcctgac caagcaccca gggaagcgcc tgggctcagg    2100
gcctgatggg gaacctacca tccgtgcaca tggcttttc cgctggattg actgggaacg     2160 gctgaacga ttggagatcc cgcctccttt cagaccccgc ccgtgtggcc gcagcggcga     2220
gaactttgac aagttcttca cgcgggcggc gccagcgctg acccctccag accgcctagt    2280
cctggccagc atcgaccagg ccgatttcca gggctttacc tacgtgaacc ccgacttcgt    2340
gcatccggat gcccgcagcc ccaccagccc agtgcctgtg cccgtcatgt aatctcaccc    2400
gccgccacta ggtgtctcca cgccccctc cgccgtgctg gcggcagccc cacttcacc      2460 ccccacttca acacctcctg ccccattcta gatcctgcac cccagcattc cggctctgcc    2520
cgcgcgggtt cgagacgccc ctcccgagcg ttcctggcct tctaaactcc atacagcctc    2580
tacagccgtc ccgcgttcaa gacttgagcg gagcccgata ttctccccga ccttagcatt    2640
ctggactctg ccccaatcgg gtccagagac accaccacac cactaaccat ccccaactcc    2700
atggggttcg agactccatc ttggtagttc tatgcctccc ccagaccccc gcccctgggg    2760
aaatagcctc acggggttgg ctgttccaga ctcaggttcc agaacaaccc tcagcctccg    2820
aggcccgccc cccaccgcct ccactccagt tctagatgag tgggaggcat gcccccctcc    2880
tccagtacgt cccgctgctg tgctctgggg atttctggga tatatggagg attcttcccc    2940
cagcggctcc caatcagctt tgttctaga cttccccatc ccgaagccat cactgctccc     3000
cgcagcctgc ctgccgtgca tggctcctgt ctggctcgga cccacccaa ccctccccag     3060 tgcctgccac tctctgggac tctcctcctc ccctcctctt cccttagcct ctcccacccc    3120
gccacagctg ctggagaata aatttgggat gctgatgctg aaaaaaaaaa aaaaaaa      3177
```

<210> SEQ ID NO 41
<211> LENGTH: 1626
<212> TYPE: DNA
<213> ORGANISM: Homo sapiens

<400> SEQUENCE: 41

```
actttgaccc tgcactccag tccgggctgg cggacagagg gctggaaaca agacgctcca     60
gaatcaggag cttcccctca ggaaatagca tcctgtgtcc ccgcactgca gttgtctggt    120
ctctccagca gtttggtact tccggctgct gcaatgcgtg tggtggtgat tggagcagga    180
gtcatcgggc tgtccaccgc cctctgcatc catgagcgct accactcagt cctgcagcca    240
ctggacataa aggtctacgc ggaccgcttc accccactca ccaccaccga cgtggctgcc    300
ggcctctggc agccctacct ttctgacccc aacaacccac aggaggcgga ctggagccaa    360
cagacctttg actatctcct gagccatgtc cattctccca acgctgaaaa cctgggcctg    420
ttcctaatct cgggctacaa cctcttccat gaagccattc cggacccttc ctggaaggac    480
acagttctgg gatttcggaa gctgaccccc agagagctgg atatgttccc agattacggc    540
tatggctggt ccacacaag cctaattctg gagggaaaga actatctaca gtggctgact    600
gaaaggttaa ctgagagggg agtgaagttc ttccagcgga agtggagtc ttttgaggag    660 gtggcaagag aaggcgcaga cgtgattgtc aactgcactg ggtatgggc tggggcgcta    720 caacgagacc cctgctgca gccaggccgg gggcagatca tgaaggtgga cgcccttgg     780 atgaagcact tcattctcac ccatgaccca gagagaggct ctacaattc ccgtacatc     840 atcccaggga cccagacagt tactcttgga ggcatcttcc agttgggaaa ctggagtgaa    900
```

| | |
|---|---|
| ctaaacaata tccaggacca caacaccatt tgggaaggct gctgcagact ggagcccaca | 960 |
| ctgaagaatg caagaattat tggtgaacga actggcttcc ggccagtacg cccccagatt | 1020 |
| cggctagaaa gagaacagct tcgcactgga ccttcaaaca cagaggtcat ccacaactat | 1080 |
| ggccatggag gctacgggct caccatccac tggggatgtg ccctggaggc agccaagctc | 1140 |
| tttgggagaa tcctggaaga aagaaattg tccagaatgc caccatccca cctctgaaga | 1200 |
| ctccagtgac tgctgcctcc ccccacaaga actcccttct cccctcagcc aatgaatcaa | 1260 |
| tgtgctcctt cataagccat tgcttctccc tcacttcttt cctcaaagaa gcatgaggtg | 1320 |
| agagaaagcc acaaagtcag tgcctggaga agggttcagc ccaacatggg gcccctctca | 1380 |
| tcactgaaat ccctctacct tctctgggtc tggcattata agaacagct gaggctgtca | 1440 |
| ttccatgagt cttcagaaga aaggacagct cagaaaatca agaggccaa ctgcccagag | 1500 |
| ccacagaaaa tggaggataa ttgaggctaa gtaacctgat acaagttgt actaacatat | 1560 |
| taaaggttct gaaagtcct gcagcaaaga caactaaaaa aaaaaaaaa aaaaaaaaa | 1620 |
| aaaaaa | 1626 |

<210> SEQ ID NO 42
<211> LENGTH: 1646
<212> TYPE: DNA
<213> ORGANISM: Rattus rattus

<400> SEQUENCE: 42

| | |
|---|---|
| caacgcagcc cagaatcagg agcaatcctg ctggagacag gttcctgcac ccccaggcca | 60 |
| ttttctcta gacacttggc accagcggct ggggtgatgc gcgtggccgt gattggagcg | 120 |
| ggagtcatcg gactgtctac agccctctgc attcatgaac gttaccaccc agcccaacct | 180 |
| ctgcacatga gatctatgc ggatcgcttc acgccgttca ctaccagcga tgtggctgcg | 240 |
| ggactctggc agccttatct ctctgacccc agcaacccgc aggaggcgga gtggaaccag | 300 |
| caaactttcg atcaccttca gagctgcctc cattctccaa acgctgagaa atgggcttg | 360 |
| gccctaatct caggctacaa cctcttccga gacgaagtcc cggacccttt ctggaaaagc | 420 |
| acagttctgg gattccggaa gctgaccccc agcgagttgg acatgttccc tgattatagc | 480 |
| tatggctggt tcaacacgag cctccttctt gaggggaaga gctacctatc atggctgact | 540 |
| gagaggttaa ctgagagggg agtgaagttc atccatcgga aggtggcatc tttcgaagag | 600 |
| gtggtgagag gaggcgtgga tgtgattatc aactgcaccg gggtgtgggc cggggctctg | 660 |
| caagcagacg cctccctgca gccaggccgg ggccagatca tccaggtgga ggccccttgg | 720 |
| ataaagcact tcatcctcac ccatgatccc agccttggca tctacaactc tccatacatc | 780 |
| atcccaggtt ccaagacagt tacactcgga ggtgtattcc agctggggaa ctggagcgag | 840 |
| ctaaacagcg tccatgacca caacaccatt tggaagagct gctgtcaact ggagcccacc | 900 |
| ctgaagaatg caagaatcat gggtgaactc actggcttcc ggccagtccg acctcaggtc | 960 |
| cggctagaaa gagaacgcct tcgctttgga tcttcaagtg cagaggtcat ccataactat | 1020 |
| ggtcatggag gttacgggct cacgattcac tggggttgtg caatggaggc agccaacctc | 1080 |
| tttgggaaaa ttctagaaga aagaacttg tccaggatgc ctccatccca cctctgagga | 1140 |
| ctctggtgaa taccacttgc cccaagacga catcccaacc ccttcagcca gttgacacca | 1200 |
| tccttgatga ttccctcccc cagccccagc ccctcctcca gcacccccctt ggcaaaggcc | 1260 |
| tgaagggagg aaatcctgct gttccctctc tgcctagtcc ttccagggca gtgatgctgg | 1320 |
| ttggttctaa ccaaggctgc atgagacagg cgagatctac aaccatgatg caattcttct | 1380 |

```
cacgctgcaa cgactgtact aaggctggtc ctactgggtg gcagggtctg tgttcagtct    1440
gatagagtag tctggaatct tttgcttaga actctgatga acggttcacg acactatcca    1500
tgtctatttg tagtgatgga gtgatgggag gagagggagg aagaagagga ggaggggag    1560 ggggaggagg gggaggaggg ggaggaggag gagggctccc tcttcagcac tctgctggtc    1620
aacatcatta aagcactgaa tatcca                                         1646
```

<210> SEQ ID NO 43
<211> LENGTH: 1411
<212> TYPE: DNA
<213> ORGANISM: Canis familiaris

<400> SEQUENCE: 43

```
atgcgtgtgg tagtgatcgg agcgggcgtc attgggctgt ccaccgccct ctgcatccac     60
gagcgctacc agtcagtcct gccatcgctg gatgtgaggg tctacgcaga ccgcttcacc    120
ccgctcacca ccactgacgt ggctgctggc ctctgtcaag cctacctctc ggaccccagc    180
aacccacagg aggcgcattg gaaccagcag accttcgact atcttctgag ccacatccat    240
tctcccaacg ctgcgagcat gggcctggcc ctaatctcag gctacaacct cttccatgaa    300
actattccgg atccttcctg gaaggacgca gttctgggat ttcggaggct gacccgtaga    360
gagctggaca tgttccccaa ttacagctat ggctggttca acacaagcct gattgtggag    420
gggaggaggt atctcgagtg gctgactaaa aggttaactg agagggagt gaaattcttc    480 cagcagaagg tggagtcttt cgaggagatg gcaagaggag gtgccgacgt gattatcaac    540
tgcaccgggg tgtgggctgg ggcattgcaa ccagatccct gctgaagcc aggtcgggga    600 cagatcatta aggtggatgc cccttggatg aagcacttca ttatcaccca tgacctagcg    660
aaaggcatct accagacccc atacatcatc ccagggatcc agacagtgac tctgggaggc    720
atctttcagc tggggaactg gagtgaggca acaacatcc aggaccacaa cactatctgg    780
gaaagctgct gtagcctgga gcccacactg aaggatgcaa aaattgttgc tgaatttact    840
ggtctccggc cagttcgccc ccagattcgg ctagaaaggg aacagcttcg ctttggatct    900
tcaaacacag aggtcatcca aactatggc catggaggct acgggctcac catccactgg    960
ggctgtgcta tggaggcagc caagctattt gggaaagtcc tagaagaaag gaagttgctc   1020
aggatgccgc caccccacct ctgaaaacac cacctcccca gaactcccc gctcccctca   1080 gccaagcaat caatatacccc ccctctaagc tatcacttac ccttcacatc agccctggct   1140
cctttctgca agaagcacaa gatgagaggg aaatgacaag atccattccc agaggcgagt   1200
ctggccctac ctgggggctca ctttgatcac tggggtctct ccactcactc tgggcctgac   1260
tgtatgaaga acagatgtag gctgttatat tctaagtcct cagaaaggaa agctcagaaa   1320
atcaaaggag caaggagaaa attggagata actgaggtta ggtaacttga ggacaaatta   1380
cactaacata ttaaaggttc tgaaaaggtg a                                    1411
```

<210> SEQ ID NO 44
<211> LENGTH: 1660
<212> TYPE: DNA
<213> ORGANISM: Macaque

<400> SEQUENCE: 44

```
agaatcagga gcttcccctc aggaaatagc atcctgtgtc cccgcacggc agttatctgg     60
tctctccagc agtttggtac ttccggctgg taccatgcgt gtggtggtga tcggagcggg    120
```

-continued

```
agtcatcggg ctgtccaccg ccctctgcat ccatgagcgc taccactcag tgctgcagcc    180
actggacata aaggtctacg cggaccgctt caccccactc accaccactg acgtagctgc    240
cggcttctgg cagccctacc tttctgaccc cagcaaccca aaggaggcgg actggagcca    300 acagacttt gaccatctcc tgagccacat ccattctccc aatgctgaaa aactgggcct    360
gttcctaatc tcaggctaca acctcttcca tgaagccatt ccgaacccett cctggaagga    420 cacagttctg ggatttcgga agctgacccc cagagagctg gatatattcc cagattacag    480
ctatggctgg ttccatacaa gcctaattct ggagggaaag aactatctac agtggctgac    540
tgaaaggtta actgagaggg gagtgaagtt cttccagcgg aaggtggagt cttttgagga    600
ggtggcaaga gaaggcgcag atgtgattgt caactgcact ggggtatggg ctggggtgct    660
gcaaccagac cccctgctgc agccaggccg ggggcagatc attaaggtgg atgccccttg    720
gataaagcat ttcattctca cccatgagcc agagagcggc atctacaatt ccccgtacat    780
catcccaggg acccagacag ttactcttgg aggcatcttc cagctgggaa actggaatga    840
gctaaacaat atccaggacc acaacaccat ttgggaaggc tgctgcagac tggagcccac    900
tctgaagaat gcaagaattg ttgatgaacg aactggcttc cggccagtac gccccaagat    960
tcggctagaa agagaacagc ttcgcgttgg accttcaaac acagaggtca tccacaacta    1020
tggccatgga ggctatgggc tcaccatcca ctggggatgt gctctggagg cagccaagct    1080 cttttgggaga atcctggaag aaaagaagtt gtccaaaatg ccaccatccc acctctgaag    1140
actccagtga ctgctgcttc ccccacaaga actcccttct ccctcagcc aacaaatcaa    1200 tgtgctcctt cataagccat tgcttatccc tcacttctttt cctcaaagaa gcatgaggtg    1260
agagaaagcc ataaagtcag tgcctggaga agggttcagc ccaacatggg gccectctca    1320 tcaccgaaat ccctctacct tctctggatc tggcattata aagaacagct ggggggctgtt    1380 attccatgag tcttcagaag aaaggacagc tcagaaactc aaagaggcca actgcccaga    1440
gccacagaaa attgaggata attgagacta agtaacatga ttacaagttg tactaacata    1500
ttaaaggttc tgaaaagtcc tgcagcaaag gcaactatct gatgttgttt aacccagtgc    1560
ttgctaaacc tatctggctg tggaacactt ttgcccagag cacccatgaa tgccatgaaa    1620
caaatttgag aaaacgctaa aaaaaaaaaa aaaaaaaaa    1660
```

<210> SEQ ID NO 45
<211> LENGTH: 351
<212> TYPE: DNA
<213> ORGANISM: Artificial Sequence
<220> FEATURE:
<223> OTHER INFORMATION: BOPKC3 - DNA construct

<400> SEQUENCE: 45

```
gcggccgcga attcagatct gggcaggaag agggcctatt tcccatgatt ccttcatatt     60
tgcatatacg atacaaggct gttagagaga taattagaat taatttgact gtaaacacaa    120
agatattagt acaaaatacg tgacgtagaa agtaataatt tcttgggtag tttgcagttt    180
taaaattatg ttttaaaatg gactatcata tgcttaccgt aacttgaaag tatttcgatt    240
tcttggcttt atatatcttg tggaaaggac gaaacaccgg cttcagcttc tcatggttc    300 caagagagaa ccatgaggaa gctgaagtct tttttgtcga cgaattaatt c            351
```

<210> SEQ ID NO 46
<211> LENGTH: 755
<212> TYPE: DNA
<213> ORGANISM: Artificial Sequence

```
<220> FEATURE:
<223> OTHER INFORMATION: BOPKC3&4 - DNA construct

<400> SEQUENCE: 46
gcggccgcga attcagatct gggcaggaag agggcctatt cccatgatt  ccttcatatt     60
tgcatatacg atacaaggct gttagagaga taattgaaat taatttgact gtaaacacaa    120
agatattagt acaaaatacg tgacgtagaa agtaataatt tcttgggtag tttgcagttt    180
taaaattatg ttttaaaatg gactatcata tgcttaccgt aacttgaaag tatttcgatt    240
tcttggcttt atatatcttg tggaaaggac gaaacaccgg cttcagcttc ctcatggttc    300
caagagagaa ccatgaggaa gctgaagtct ttttttacat caggttgttt ttctgttttt    360
acatcaggtt gttttttctgt ttggtttttt ttttacacca cgtttatacg ccgctcgagt    420
agggcggtgc ggctcaggct ctgccccgcc tccggggcta tttgcatacg accatttcca    480
gtaattccca gcagccaccg tagctatatt tggtagaaca acgagcactt tctcaactcc    540
agtcaataac tacgttagtt gcattacaca ttgggctaat ataaatagag gttaaatctc    600
taggtcattt aagagaagtc ggcctatgtg tacagacatt tgttccaggg gctttaaata    660
gctggtggtg gaactcaata ttcggcctcc tccagaagtt tgaggcaaga gacctcaaac    720
ttctggagga ggcttttttg tcgacgaatt aattc                               755

<210> SEQ ID NO 47
<211> LENGTH: 351
<212> TYPE: DNA
<213> ORGANISM: Artificial Sequence
<220> FEATURE:
<223> OTHER INFORMATION: BOPKC3cont - DNA construct

<400> SEQUENCE: 47
gcggccgcga attcagatct gggcaggaag agggcctatt cccatgatt  ccttcatatt     60
tgcatatacg atacaaggct gttagagaga taattgaaat taatttgact gtaaacacaa    120
agatattagt acaaaatacg tgacgtagaa agtaataatt tcttgggtag tttgcagttt    180
taaaattatg ttttaaaatg gactatcata tgcttaccgt aacttgaaag tatttcgatt    240
tcttggcttt atatatcttg tggaaaggac gaaacaccgg atttcgcttc gctaccttcg    300
caagagacga aggtagcgaa gcgaaattct ttttttgtcga cgaattaatt c             351

<210> SEQ ID NO 48
<211> LENGTH: 755
<212> TYPE: DNA
<213> ORGANISM: Artificial Sequence
<220> FEATURE:
<223> OTHER INFORMATION: BOPKC3&4cont - DNA construct

<400> SEQUENCE: 48
gcggccgcga attcagatct gggcaggaag agggcctatt cccatgatt  ccttcatatt     60
tgcatatacg atacaaggct gttagagaga taattagaat taatttgact gtaaacacaa    120
agatattagt acaaaatacg tgacgtagaa agtaataatt tcttgggtag tttgcagttt    180
taaaattatg ttttaaaatg gactatcata tgcttaccgt aacttgaaag tatttcgatt    240
tcttggcttt atatatcttg tggaaaggac gaaacaccgg atttcgcttc gctaccttcg    300
caagagacga aggtagcgaa gcgaaattct tttttacat  caggttgttt ttctgttttt    360
acatcaggtt gttttctgt ttggtttttt ttttacacca cgtttatacg ccgctcgagt    420
agggcggtgc ggctcaggct ctgccccgcc tccggggcta tttgcatacg accatttcca    480
```

```
gtaattccca gcagccaccg tagctatatt tggtagaaca acgagcactt tctcaactcc    540
agtcaataac tacgttagtt gcattacaca ttgggctaat ataaatagag gttaaatctc    600
taggtcattt aagagaagtc ggcctatgtg tacagacatt tgttccaggg gctttaaata    660
gctggtggtg gaactcaata ttcgggagcc tatggtccac tatgccaaga gagcatagtg    720
gaccataggc tccttttttg tcgacgaatt aattc                              755

<210> SEQ ID NO 49
<211> LENGTH: 53
<212> TYPE: RNA
<213> ORGANISM: Homo sapiens

<400> SEQUENCE: 49
ggcaaggggu uccugaccaa gccaagagag cuuggucagg aaccccuugc auu           53

<210> SEQ ID NO 50
<211> LENGTH: 53
<212> TYPE: RNA
<213> ORGANISM: Homo sapiens

<400> SEQUENCE: 50
ggccucuucu uccuucacaa cccaagagag guugugaagg aagaagaggc cuu           53

<210> SEQ ID NO 51
<211> LENGTH: 53
<212> TYPE: RNA
<213> ORGANISM: Homo sapiens

<400> SEQUENCE: 51
ggcuucagcu uccucauggu uccaagagag aaccaugagg aagcugaagu cuu           53

<210> SEQ ID NO 52
<211> LENGTH: 52
<212> TYPE: RNA
<213> ORGANISM: Homo sapiens

<400> SEQUENCE: 52
ggccuccucc agaaguuuga ggcaagagac cucaaacuuc uggaggaggc uu            52

<210> SEQ ID NO 53
<211> LENGTH: 53
<212> TYPE: RNA
<213> ORGANISM: Homo sapiens

<400> SEQUENCE: 53
gguggccgau gcugacaacu gccaagagag caguugucag caucggccac cuu           53

<210> SEQ ID NO 54
<211> LENGTH: 52
<212> TYPE: RNA
<213> ORGANISM: Homo sapiens

<400> SEQUENCE: 54
ggggagggcg aguauuacaa ugcaagagac auuguaauac ucgcccuccu cu            52

<210> SEQ ID NO 55
<211> LENGTH: 53
<212> TYPE: RNA
<213> ORGANISM: Homo sapiens

<400> SEQUENCE: 55
ggugccaugu ccuuggugu cucaagagaa gacaccaaag gacauggcac cuu            53
```

<210> SEQ ID NO 56
<211> LENGTH: 52
<212> TYPE: RNA
<213> ORGANISM: Homo sapiens

<400> SEQUENCE: 56
ggcagccucc uccagaaguu ugcaagagac aaacuucugg aggaggcugc uu          52

<210> SEQ ID NO 57
<211> LENGTH: 53
<212> TYPE: RNA
<213> ORGANISM: Homo sapiens

<400> SEQUENCE: 57
gggaacugga gcgagcuaaa cacaagagau guuuagcucg cuccaguucc cuu         53

<210> SEQ ID NO 58
<211> LENGTH: 53
<212> TYPE: RNA
<213> ORGANISM: Homo sapiens

<400> SEQUENCE: 58
ggccggggcc agaucaucca ggcaagagac cuggaugauc uggccccggc cuu         53

<210> SEQ ID NO 59
<211> LENGTH: 53
<212> TYPE: RNA
<213> ORGANISM: Homo sapiens

<400> SEQUENCE: 59
ggcguggaug ugauuaucaa cucaagagaa guugauaauc acaccacgc cuu          53

<210> SEQ ID NO 60
<211> LENGTH: 53
<212> TYPE: RNA
<213> ORGANISM: Homo sapiens

<400> SEQUENCE: 60
ggcugacuga gagguuaacu gacaagagau caguuaaccu cucagucagc cuu         53

<210> SEQ ID NO 61
<211> LENGTH: 54
<212> TYPE: RNA
<213> ORGANISM: Homo sapiens

<400> SEQUENCE: 61
ggaggcggag uggaaccagc aaacaagaga uuugcugguu ccacuccgcc ucuu        54

<210> SEQ ID NO 62
<211> LENGTH: 53
<212> TYPE: RNA
<213> ORGANISM: Homo sapiens

<400> SEQUENCE: 62
ggaaacugga gugaacuaaa cacaagagau guuuaguuca cuccaguuuc cuu         53

<210> SEQ ID NO 63
<211> LENGTH: 53
<212> TYPE: RNA
<213> ORGANISM: Homo sapiens

<400> SEQUENCE: 63

```
ggccggggc agaucaugaa ggcaagagac cuucaugauc ugcccccggc cuu      53
```

<210> SEQ ID NO 64
<211> LENGTH: 53
<212> TYPE: RNA
<213> ORGANISM: Homo sapiens

<400> SEQUENCE: 64

```
ggcgcagacg ugauugucaa cucaagagaa guugacaauc acgucugcgc cuu      53
```

<210> SEQ ID NO 65
<211> LENGTH: 53
<212> TYPE: RNA
<213> ORGANISM: Homo sapiens

<400> SEQUENCE: 65

```
ggcugacuga aagguuaacu gacaagagau caguuaaccu uucagucagc cuu      53
```

<210> SEQ ID NO 66
<211> LENGTH: 53
<212> TYPE: RNA
<213> ORGANISM: Homo sapiens

<400> SEQUENCE: 66

```
gaggcggacu ggagccaaca gacaagagau cuguuggcuc cagucccgccu cuu     53
```

<210> SEQ ID NO 67
<211> LENGTH: 53
<212> TYPE: RNA
<213> ORGANISM: Homo sapiens

<400> SEQUENCE: 67

```
ggauuucgcu ucgcuaccuu cgcaagagac gaagguagcg aagcgaaauu cuu      53
```

<210> SEQ ID NO 68
<211> LENGTH: 52
<212> TYPE: RNA
<213> ORGANISM: Homo sapiens

<400> SEQUENCE: 68

```
gggagccuau gguccacuau gccaagagag cauaguggac cauaggcucc uu       52
```

<210> SEQ ID NO 69
<211> LENGTH: 418
<212> TYPE: DNA
<213> ORGANISM: Artificial Sequence
<220> FEATURE:
<223> OTHER INFORMATION: BLTPKC3miR - DNA construct

<400> SEQUENCE: 69

```
gcggccgcga attctagggc ggtgcggctc aggctctgcc ccgcctccgg ggctatttgc     60
atacgaccat ttccagtaat tcccagcagc caccgtagct atatttggta gaacaacgag    120
cactttctca actccagtca ataactacgt tagttgcatt acacattggg ctaatataaa    180
tagaggttaa atctctaggt catttaagag aagtcggcct atgtgtacag acatttgttc    240
cagggctttt aaatagctgg tggtggaact caatattcgg tatattgctg ttgacagtga    300
gcgagacttc agcttcctca tggtactgtg aagcagatgg gtaccatgag gaagctgaag    360
tcgcgcctac tgcctcggac ttcaagctag cggtacccttt tttgtcgacg aattaatc     418
```

<210> SEQ ID NO 70
<211> LENGTH: 418

```
<212> TYPE: DNA
<213> ORGANISM: Artificial Sequence
<220> FEATURE:
<223> OTHER INFORMATION: BLTPKC4miR - DNA construct

<400> SEQUENCE: 70
gcggccgcga attctagggc ggtgcggctc aggctctgcc ccgcctccgg ggctatttgc        60
atacgaccat ttccagtaat tcccagcagc caccgtagct atatttggta gaacaacgag       120
cactttctca actccagtca ataactacgt tagttgcatt acacattggg ctaatataaa       180
tagaggttaa atctctaggt catttaagag aagtcggcct atgtgtacag acatttgttc       240
caggggcttt aaatagctgg tggtggaact caatattcgg tatattgctg ttgacagtga       300
gcgaagcctc ctccagaagt ttgaactgtg aagcagatgg gttcaaactt ctggaggagg       360
ctgcgcctac tgcctcggac ttcaagctag cggtacctttt tttgtcgacg aattaatc       418

<210> SEQ ID NO 71
<211> LENGTH: 125
<212> TYPE: RNA
<213> ORGANISM: Homo sapiens

<400> SEQUENCE: 71
gguauauugc uguugacagu gagcgagacu ucagcuuccu caugguacug ugaagcagau        60
ggguaccaug aggaagcuga agucgcgccu acugccucgg acuucaagcu agcgguaccu       120
uuuuu                                                                 125

<210> SEQ ID NO 72
<211> LENGTH: 124
<212> TYPE: RNA
<213> ORGANISM: Homo sapiens

<400> SEQUENCE: 72
gguauauugc uguugacagu gagcgaagcc uccuccagaa guuugaacug ugaagcagau        60
ggguucaaac uucuggagga ggcugcgccu acugccucgg acuucaagcu agcgguaccu       120
uuuu                                                                  124
```